United States Patent
Deng et al.

(10) Patent No.: US 11,666,574 B2
(45) Date of Patent: Jun. 6, 2023

(54) COMBINATION THERAPY INVOLVING DIARYL MACROCYCLIC COMPOUNDS

(71) Applicant: TURNING POINT THERAPEUTICS, INC., San Diego, CA (US)

(72) Inventors: Wei Deng, San Diego, CA (US); Dayong Zhai, San Diego, CA (US); Laura Rodon, San Diego, CA (US); Brion W. Murray, San Diego, CA (US); Jingrong J. Cui, San Diego, CA (US); Nathan V. Lee, San Diego, CA (US)

(73) Assignee: Turning Point Therapeutics, Inc., San Diego, CA (US)

( * ) Notice: Subject to any disclaimer, the term of this patent is extended or adjusted under 35 U.S.C. 154(b) by 262 days.

(21) Appl. No.: 17/104,739

(22) Filed: Nov. 25, 2020

(65) Prior Publication Data

US 2021/0154198 A1    May 27, 2021

Related U.S. Application Data

(60) Provisional application No. 62/941,031, filed on Nov. 27, 2019, provisional application No. 62/941,033, filed on Nov. 27, 2019, provisional application No. 62/992,573, filed on Mar. 20, 2020.

(51) Int. Cl.
A61K 31/519    (2006.01)

(52) U.S. Cl.
CPC .................................. *A61K 31/519* (2013.01)

(58) Field of Classification Search
CPC . C07D 498/18; A61K 31/439; A61K 31/4995
See application file for complete search history.

(56) References Cited

U.S. PATENT DOCUMENTS

| | | | |
|---|---|---|---|
| 9,714,258 B2 | 7/2017 | Cui et al. | |
| 10,246,466 B2 | 4/2019 | Cui et al. | |
| 10,294,242 B2 | 5/2019 | Cui et al. | |
| 10,316,044 B2 | 6/2019 | Cui et al. | |
| 2016/0166571 A1* | 6/2016 | Janes | A61K 45/06 514/210.18 |
| 2016/0346262 A1* | 12/2016 | Fan | A61K 31/7008 |
| 2016/0346282 A1 | 12/2016 | Pachter et al. | |
| 2018/0186813 A1 | 7/2018 | Cui et al. | |
| 2018/0194777 A1 | 7/2018 | Cui et al. | |
| 2018/0325901 A1 | 11/2018 | Cui et al. | |

FOREIGN PATENT DOCUMENTS

| | | |
|---|---|---|
| WO | 2015112806 A2 | 7/2015 |
| WO | 2018140554 A1 | 8/2018 |
| WO | WO 2018/140554 * | 8/2018 ........... C07D 498/18 |

OTHER PUBLICATIONS

International Search Report and Written Opinion in International Patent Application No. PCT/US2020/062374, dated Feb. 17, 2021, 9 pages.
Berge et al. (Jan. 1977) "Pharmaceutical Salts", Journal of Pharmaceutical Sciences, 66(1):1-19.
Bromann et al. (2004) "The Interplay between Src Family Kinases and Receptor Tyrosine Kinases", Oncogene, 23(48):7957-7968.
Zhang et al. (2012) "Targeting Src Family Kinases in Anti-Cancer Therapies: Turning Promise into Triumph", Trends n Pharmacological Sciences, 33(3): 122-128(14 pages).
Golubovskaya et al. (Aug. 2003) "Simultaneous Inhibition of Focal Adhesion Kinase and Src Enhances Detachment and Apoptosis in Colon Cancer Cell Lines", Molecular Cancer Research, 1(10):755-764.
Ianevski et al. (Aug. 1, 2017) "SynergyFinder: A Web Application for Analyzing Drug Combination Dose-Response Matrix Data", Bioinformatics, 33(15):2413-2415.
Kanteti et al. (May 24, 2016) "FAK and Paxillin, Two Potential Targets in Pancreatic Cancer", Oncotarget, 7(21):31586-31601.
Kelber et al. (May 15, 2012) "KRas Induces a Src/PEAK1/ErbB2 Kinase Amplification Loop That Drives Metastatic Growth and Therapy Resistance in Pancreatic Cancer", Cancer Research, 72(10):2554-2564.
Kessler et al. (Apr. 2019) "Resistance to Src Inhibition Alters the BRAF-mutant Tumor Secretome to promote an Invasive Phenotype and Therapeutic Escape through a FAK>p130Cas>c-Jun Signaling Axis", Oncogene, 38(14):2565-2579(26 pages).
Konstantinidou et al. (Apr. 2013) "RHOA-FAK is a required Signaling Axis for the Maintenance of KRAS-driven Lung Adenocarcinomas", Cancer Discovery, 3(4)-444-457(22 pages).
Wagner et al. (Mar. 2019) "Suppression of Interferon Gene Expression Overcomes Resistance to MEK Inhibition in KRAS-Mutant Colorectal Cancer", Oncogene, 38(10):1717-1733.
Stolze et al. (Feb. 23, 2015) "Comparative Analysis of KRAS Codon 12, 13, 18, 61, and 117 Mutations using Human MCF10A Isogenic Cell Lines", Scientific Reports, Article No. 8535, 5:1-9 pages.
Nimwegen et al. (Oct. 2006) "Focal Adhesion Kinase and Protein Kinase B Cooperate to Suppress Doxorubicin-Induced Apoptosis of Breast Tumor Cells", Molecular Pharmacology, 70(4):1330-1339.
Rao et al. (Aug. 2018) "Dasatinib Sensitises KRAS-Mutant Cancer Cells to Mitogen-Activated Protein Kinase Kinase Inhibitor via Inhibition of TAZ Activity", European Journal of Cancer, 99:37-48.
Seguin et al. (Apr. 2015) "Integrins and Cancer: Regulators of Cancer Stemness, Metastasis, and Drug Resistance", Trends in Cell Biology, 25(4):234-240 (17 pages).

* cited by examiner

*Primary Examiner* — Erich A Leeser
(74) *Attorney, Agent, or Firm* — Mintz, Levin, Cohn, Ferris, Glovsky and Popeo, P.C.

(57) ABSTRACT

The present disclosure relates to methods and compositions for treating cancer with a diaryl macrocycle in combination with an inhibitor of MAPK/ERK kinase-1 and -2 (MEK1 and MEK2; MAP2K1 and MAP2K2), such as trametinib.

17 Claims, 6 Drawing Sheets

Steady-state exposure, 2h post treatment

COMBINATION THERAPY INVOLVING DIARYL MACROCYCLIC COMPOUNDS

CROSS REFERENCES TO RELATED APPLICATIONS

This application claims priority to U.S. Provisional Application No. 62/941,031, filed Nov. 27, 2019; U.S. Provisional Application No. 62/941,033, filed Nov. 27, 2019; and U.S. Provisional Application No. 62/992,573, filed Mar. 20, 2020, each of which is incorporated herein in its entirety for all purposes.

TECHNICAL FIELD

The present disclosure relates to methods and compositions for treating cancer with a diaryl macrocycle in combination with an inhibitor of MAPK/ERK kinase-1 and -2 (MEK1 and MEK2; MAP2K1 and MAP2K2), such as trametinib.

BACKGROUND

Kirsten Rat Sarcoma Viral Oncogene homolog KRAS is one of three RAS protein family members (N, H, and K-RAS) that are small membrane bound intracellular GTPase proteins. KRAS cycles between an inactive guanosine diphosphate (GDP)-bound state and an active guanosine triphosphate (GTP)-bound state. Active GTP-bound KRAS interacts with numerous effectors to stimulate multiple signaling pathways (e.g. PI3K-AKT-MTOR, RAF-MEK-ERK) to affect a range of cellular processes (e.g. survival, proliferation, cytoskeletal organization).

KRAS is one of the most frequently mutated oncogenes across a broad spectrum of human cancers (18%, Catalogue of Somatic Mutations in Cancer (COSMIC) database v90), including non-small cell lung, colorectal, pancreatic, uterine, bladder, stomach, renal, breast, skin, prostate, acute myeloid leukemia, cervical, liver acute lymphoblastic leukemia, ovarian, and brain cancers. KRAS mutations primarily occur in KRAS codons 12 and 13 but occur in codons 18, 61, 117, and 146 at low frequencies and have distinct effects on tumor cell signaling based on the codon and missense mutation (Stolze et al. Sci Rep. 2015; 5:8535).

Direct targeting of a MEK1 and MEK2 through a reversible binding in an allosteric binding pocket has been evaluated in clinical trials with investigational drugs in patients harboring KRAS mutations. In a Phase 3 clinical trial of the MEK inhibitor selumetinib in combination with docetaxel in mutant KRAS NSCLC patients, there was no benefit of the combination over docetaxel alone (Janne at al, 2017 JAMA). In a Phase 2 clinical trial comparing trametinib treatment to docetaxel in patients with mutant KRAS NSCLC was prematurely terminated because trametinib treatment response crossed the futility boundary in the interim analysis (Blumenschein et al 2015). Single agent MEK drug clinical trials and drug combinations of a MEK drug with chemotherapy has been shown to be ineffective in mutant KRAS NSCLC.

Combinations that target MAPK pathway feedback reactivation, RTK-induced PI3K pathway activation and increased apoptosis will be necessary to provide significant improvements in clinical benefit.

SRC kinase has been identified to contribute broadly to cancer treatment resistance including radiotherapy, chemotherapy, and targeted therapy (Zhang S and Yu D. *Trends Pharmacol Sci.* 2012; 33(3):122-8). SRC family kinases can promote mitogenic signaling from growth factor receptors in a number of ways, including initiation of signaling pathways required for DNA synthesis, control of receptor turnover, actin cytoskeleton rearrangements and motility, and survival (Bromann et al, *Oncogene* 2004; 23(48):7957-68). It was reported that KRAS induces a Src/PEAK1/ErbB2 kinase amplification loop that drives metastatic growth and therapy resistance in pancreatic cancer (Kelber et al, *Cancer Res.* 2012; 72(10):2554-64). The SRC inhibitor dasatinib was discovered to enhance the anti-tumor activity of MEK inhibitor through inhibition of TAZ activity and the combination of dasatinib and trametinib represents a potential strategy for the treatment of KRAS-driven cancers (Rao et al, Eur J Cancer. 2018 August; 99:37-48). FAK plays a vital role in signaling pathways mediated through integrins, RTKs, RAS, and TGF β (Kanteti et al, *Oncotarget.* 2016; 7(21):31586-601) and is also likely to suppress p53 expression to promote cell survival (Golubovskaya et al, *International Review of Cytology.* 2007; 263:103-153). Recent findings have demonstrated that integrins participate in the regulation of cancer stem-cell biology and are required for cancer progression, metastasis, and drug resistance via SRC/FAK signaling (Seguin et al, *Trends Cell Biol.* 2015; 25(4):234-40). Src has been identified as a key mediator of thyroid cancer pro-tumorigenic processes and a promising therapeutic target for thyroid cancer. However, single-agent Src inhibition promotes a more invasive phenotype through an IL-1β>FAK>p130Cas>c-Jun>MMP signaling axis, and the combined inhibition of FAK and Src has the potential to block Src inhibitor-induced phenotype switch and resistance (Kessler et al, *Oncogene.* 2019; 38:2565-2579). Compensatory upregulation of the PI3K/AKT signaling pathway is a resistance mechanism in targeting KRAS mutation, which promotes cancer cell survival. FAK through phosphorylated Y397 directly interacts with the SH2 domain of p85, the regulatory subunit of PI3K to activate the PI3K pathway and suppress doxorubicin-induced apoptosis (van Nimwegen et al, *Mol Pharmacol.* 2006; 70(4):1330-1339). Src mediated phosphorylation of FAK at Y925 creates a docking site for GRB2 which activates the small GTP protein RAS and the downstream ERK2 (MAPK) (Kanteti et al, Oncotarget. 2016; 7(21):31586-601). Paxillin is a major component of focal adhesions that form a structural link between extracellular matrix and actin cytoskeleton. In cancer cells, its function is regulated through Src and FAK mediated phosphorylation. The dual inhibition of FAK and Src inhibitor was much more effective as compared to FAK inhibition alone as evidenced with increased cell detachment, inhibition of AKT/ERK1/2 and Src, and increased apoptosis (Golubovskaya et al, *Molecular Cancer Research.* 2003; 1(10):755-764). RhoA-FAK is a required signaling axis for the maintenance of KRAS-driven lung adenocarcinomas. Pharmacologic inhibition of FAK in vivo downregulates p-AKT and does not trigger the emergence of PI3K/AKT-dependent compensatory mechanisms (Konstantinidou et al, *Cancer Discov.* 2013, 3(4):444-57). It was reported that interferon- and inflammatory-related gene sets were enriched in KRAS mutant colon cell lines exhibiting intrinsic and acquired resistance to MEK inhibition (Wagner et al, *Oncogene.* 2019, 38(10):1717-1733). JAK2 serves signal transduction for inflammatory cytokines and inhibition of JAK2 may reduce the secretion of interferon- and inflammatory-related gene sets and sensitize KRAS mutant cell lines to MEK inhibition. In preclinical studies, MEK inhibition led to autocrine activation of STAT3 through JAK and FGFR kinase activities to enable drug resistance (Lee et al, *Cancer Cell* 2014). The combination of the MEK inhibitor cobimetinib with the JAK1/2 inhibitor ruxolitinib and multitargeted kinase inhibitor ponatinib (includes FGFR inhibitory activity) exhibited enhanced efficacy in mouse xenograft tumor models (Lee et al, *Cancer Cell* 2014).

Overall, pharmacological targeting of central downstream signaling effectors of mutant activated RAS proteins has been challenging and has not yet led to successful treatments in the clinic. The combination of a SRC/FAK/JAK2 inhibitor with a MEK1/2 inhibitor, in particular trametinib, represents a novel therapeutic invention to maximize the antitumor activities and duration of response of a MEK1/2 inhibitor, in particular trametinib, for the treatment of patients with KRAS mutation.

SUMMARY

It has been discovered that the combination of a MEK inhibitor, such as trametinib, and one or more compounds that inhibit FAK, SRC and/or JAK2 provides a robust response in cancers driven by KRAS, in particular, cancers harboring one or more KRAS mutations.

In one aspect, the disclosure provides a method for treating cancer in a host animal, the method comprising the step of administering to the host animal a therapeutically effective amount of one or more compounds that inhibit FAK, SRC and/or JAK2, in combination with a therapeutically effective amount of a MEK inhibitor, such as trametinib. In some embodiments, the host animal is a human patient. In some embodiments, the host animal is a laboratory animal such as a rodent.

In another aspect, the disclosure provides a method for treating cancer in a host animal, the method comprising the step of administering to the host animal a therapeutically effective amount of a compound that inhibits FAK, SRC, and JAK2, in combination with a therapeutically effective amount of a MEK inhibitor, such as trametinib. In some embodiments, the host animal is a human patient. In some embodiments, the host animal is a laboratory animal such as a rodent.

In another aspect, the disclosure provides one of more compounds that inhibit FAK, SRC and/or JAK2, or a pharmaceutically acceptable salt thereof, for use in the treatment of cancer in a patient, in combination with a therapeutically effective amount of a MEK inhibitor, such as trametinib.

In another aspect, the disclosure provides a compound that inhibits FAK, SRC and JAK2, or a pharmaceutically acceptable salt thereof, for use in the treatment of cancer in a patient, in combination with a therapeutically effective amount of a MEK inhibitor, such as trametinib.

In another aspect, the disclosure provides use of one or more compounds that inhibit FAK, SRC and/or JAK2, or a pharmaceutically acceptable salt thereof, in the preparation of a medicament comprising a therapeutically effective amount of the compound, for treating cancer in a patient in combination with a therapeutically effective amount of a MEK inhibitor, such as trametinib.

In another aspect, the disclosure provides use of a compound that inhibits FAK, SRC and JAK2, or a pharmaceutically acceptable salt thereof, in the preparation of a medicament comprising a therapeutically effective amount of the compound, for treating cancer in a patient in combination with a therapeutically effective amount of a MEK inhibitor, such as trametinib.

In another aspect, the disclosure provides a composition comprising one or more compounds that inhibit FAK, SRC and/or JAK2, or a pharmaceutically acceptable salt thereof, in a therapeutically effective amount, for use in the treatment of cancer in a patient, in combination with a therapeutically effective amount of a MEK inhibitor, such as trametinib.

In another aspect, the disclosure provides a composition comprising a compound that inhibits FAK, SRC and JAK2, or a pharmaceutically acceptable salt thereof, in a therapeutically effective amount, for use in the treatment of cancer in a patient, in combination with a therapeutically effective amount of a MEK inhibitor, such as trametinib.

In another aspect, the disclosure provides a medicament comprising one or more compounds that inhibit FAK, SRC and/or JAK2, or a pharmaceutically acceptable salt thereof, combined with a MEK inhibitor, such as trametinib, or a pharmaceutically acceptable salt thereof, in fixed or free combination.

In another aspect, the disclosure provides a medicament comprising a compound that inhibits FAK, SRC and JAK2, or a pharmaceutically acceptable salt thereof, combined with a MEK inhibitor, such as trametinib, or a pharmaceutically acceptable salt thereof, in fixed or free combination.

In another aspect, the disclosure provides a synergistic composition of one or more compounds that inhibit FAK, SRC and/or JAK2 and a MEK inhibitor, such as trametinib, where the two components come into contact with each other at a locus.

In another aspect, the disclosure provides a synergistic composition of a compound that inhibits FAK, SRC and JAK2 and a MEK inhibitor, such as trametinib, where the two components come into contact with each other at a locus.

In another aspect, the disclosure provides a synergistic composition of one or more compounds that inhibit FAK, SRC and/or JAK2, and a MEK inhibitor, such as trametinib, where the two components come into contact with each other only in the human body.

In another aspect, the disclosure provides a synergistic composition of a compound that inhibits FAK, SRC and JAK2, and a MEK inhibitor, such as trametinib, where the two components come into contact with each other only in the human body.

In some embodiments the compound that inhibits FAK, SRC and JAK2 is of the formula I

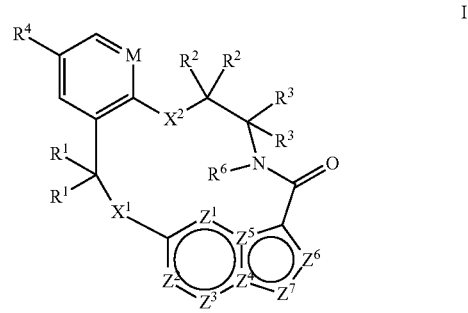

wherein

M is $CR^5$ or N;

$X^1$ and $X^2$ are independently —$C(R^7)(R^8)$—, —S—, —S(O)—, —S(O)$_2$—, —O— or —N($R^9$)—;

each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)$OR^7$ or —C(O)$NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —$OC_1$-$C_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OW;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

In some embodiments of the above aspects, the compound that inhibits FAK, SRC and JAK2 is of the formula (referred to herein as Compound 1)

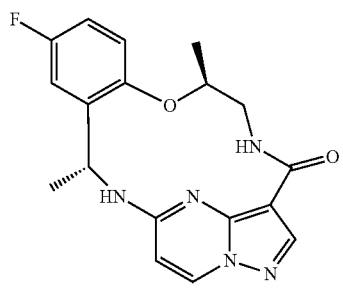 [SMILES: C[C@H]1CNC(=O)c2cnn3ccc(nc23)N[C@H](C)c2cc(F)ccc2O1]

or a pharmaceutically acceptable salt thereof.

In some embodiments of the various aspects described herein, and in particular those aspects described above, the cancer is non-small cell lung cancer mediated by a genetically altered KRAS comprising at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H; or the KRAS comprises at least one mutation that is not G12A, G12C, G12S, G12V, and Q61K.

In some embodiments of the various aspects described herein, and in particular those aspects described above, the cancer is colorectal cancer mediated by a genetically altered KRAS comprising at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I.

In some embodiments of the various aspects described herein, and in particular those aspects described above, the cancer is pancreatic cancer mediated by a genetically altered KRAS comprising at least one mutation selected from the group consisting of G12D, G12V, G12R, Q61H, G12C, and G12S.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A method of treating cancer in a patient in need of such treatment, the method comprising the step of administering to the patient a therapeutically effective amount of a compound that inhibits FAK, SRC, and JAK2, in combination with a therapeutically effective amount of trametinib.

2. A method of treating cancer in patient in need of such treatment, the method comprising the step of administering to the patient having cancer a therapeutically effective amount of a compound that inhibits FAK, SRC, and JAK2, in combination with a therapeutically effective amount of trametinib, wherein at least one genetically altered oncogenic gene has been previously identified in the patient.

3. A method of treating a cancer mediated by at least one genetically altered oncogenic gene, in patient in need of such treatment, the method comprising the step of administering to the patient having cancer a therapeutically effective amount of a compound that inhibits FAK, SRC, and JAK2, in combination with a therapeutically effective amount of trametinib.

4. A method of treating cancer in a patient comprising;
    i. identifying at least one genetically altered oncogenic gene in the patient, and
    ii. administering to the patient a therapeutically effective amount of a compound that inhibits FAK, SRC, and JAK2, in combination with a therapeutically effective amount of trametinib.

5. The method of any one of clauses 2 to 4, wherein the at least one genetically altered oncogenic gene is a genetically altered KRAS, a genetically altered NRAS, a genetically altered HRAS, a genetically altered BRAF, a genetically altered MEK, and/or a genetically altered PI3K.

6. A method of treating non-small cell lung cancer in patient in need of such treatment, the method comprising the step of administering to the patient having non-small cell lung cancer a therapeutically effective amount of a compound that inhibits FAK, SRC, and JAK2, in combination with a therapeutically effective amount of trametinib.

7. A method of treating non-small cell lung cancer in patient in need of such treatment, the method comprising the step of administering to the patient having cancer a therapeutically effective amount of a compound that inhibits FAK, SRC, and JAK2, in combination with a therapeutically effective amount of trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

8. A method of treating non-small cell lung cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient having non-small cell lung cancer a therapeutically effective amount of a compound that inhibits FAK, SRC, and JAK2, in combination with a therapeutically effective amount of trametinib.

9. A method of treating non-small cell lung cancer in a patient comprising;
    i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
    ii. administering to the patient a therapeutically effective amount of a compound that inhibits FAK, SRC, and JAK2, in combination with a therapeutically effective amount of trametinib.

10. The method of any one of clauses 7 to 9, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H; or KRAS comprises at least one mutation that is not G12A, G12C, G12S, G12V, and Q61K.

11. A method for treating colorectal cancer or pancreatic cancer in a patient in need of such treatment, the method comprising the step of administering to the patient a therapeutically effective amount of a compound that inhibits FAK, SRC, and JAK2, in combination with a therapeutically effective amount of trametinib.

12. A method of treating colorectal cancer or pancreatic cancer in patient in need of such treatment, the method comprising the step of administering to the patient having cancer a therapeutically effective amount of a compound that inhibits FAK, SRC, and JAK2, in combination with a therapeutically effective amount of trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

13. A method of treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient having colorectal cancer or pancreatic cancer a therapeutically effective amount of a compound that inhibits FAK, SRC, and JAK2, in combination with a therapeutically effective amount of trametinib.

14. A method of treating colorectal cancer or pancreatic cancer in a patient comprising;
    i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and ii. administering to the patient a therapeutically effective amount of a compound that inhibits FAK, SRC, and JAK2, in combination with a therapeutically effective amount of trametinib.

15. The method of any one of clauses 12 to 14, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

16. The method of any one of the preceding clauses, wherein the compound that inhibits FAK, SRC, and JAK2 is administered in an amount of from about 40 mg to about 200 mg.

17. The method of any one of the preceding clauses, wherein trametinib is administered in an amount of from about 0.5 mg to about 2.5 mg.

18. The method of any one of the preceding clauses, wherein the compound that inhibits FAK, SRC and JAK2 is of the formula I

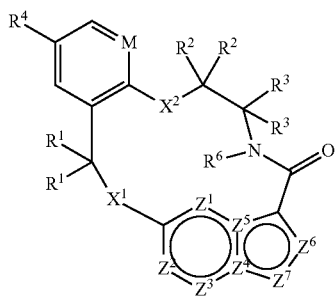

wherein

M is $CR^5$ or N;

$X^1$ and $X^2$ are independently —C($R^7$)($R^8$)—, —S—, —S(O)—, —S(O)$_2$—, —O— or —N($R^9$)—;

each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O) O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O) NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —CO$_2$$C_1$-$C_6$ alkyl, —CONH$_2$, —CONH($C_1$-$C_6$ alkyl), —CON($C_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O) O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O) NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-

$C_6$ alkyl)$_2$, —P(O)($C_1$-$C_6$ alkyl)$_2$, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OW;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —NH$_2$, —NH($C_1$-$C_6$ alkyl), —NH(phenyl), —NH(heteroaryl), —CN, or CF$_3$, and provided that at least one of $Z^1$, $Z^2$, $Z^3$, $Z^4$, $Z^5$, $Z^6$ or $Z^7$ is N or NH;

or a pharmaceutically acceptable salt thereof.

19. The method of any one of the preceding clauses, wherein the compound that inhibits FAK, SRC and JAK2 is a compound of the formula

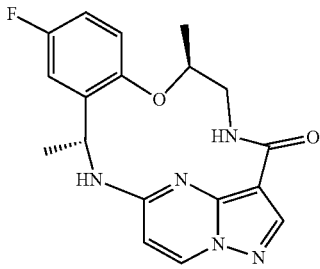 [SMILES: C[C@H]1CNC(=O)c2cnn3ccc(nc23)N[C@H](C)c2cc(F)ccc2O1]

or a pharmaceutically acceptable salt thereof.

20. The method according to any one of the preceding clauses, wherein the compound that inhibits FAK, SRC and JAK2 is administered in an amount of about 40 mg, about 80 mg, about 120 mg, or about 160 mg by once a day or twice a day.

21. The method according to any one of the preceding clauses, wherein trametinib is administered in an amount of about 1 mg or about 2 mg.

22. The method according to any one of the preceding clauses, wherein the compound that inhibits FAK, SRC and JAK2 is administered on a schedule of at least one dose of about 40 mg, about 80 mg QD, about 120 mg QD, or about 160 mg QD, followed by at least one dose of about 40 mg BID, about 80 mg BID, about 120 mg BID, or about 160 mg BID.

23. The method according to any one of the preceding clauses, wherein trametinib is administered in at least one dose of about 1 mg QD, or about 2 mg QD.

24. The method according to any one of the preceding clauses, wherein the compound that inhibits FAK, SRC and JAK2 is administered at the same time as trametinib.

25. The method according to any one of clauses 1 to 23, wherein the compound that inhibits FAK, SRC and JAK2 is administered prior to trametinib.

26. The method according to any one of clauses 1 to 23, wherein the compound that inhibits FAK, SRC and JAK2 is administered after trametinib.

27. The method according to any one of the preceding clauses, wherein the patient has not received a prior treatment.

28. The method according to any one of clauses 1 to 26, wherein the patient has received at least one prior treatment of one or more chemotherapeutic agents or immunotherapies.

29. The method according to any one of clauses 1 to 26 or 28, wherein the patient has received at least one prior treatment of one or more chemotherapeutic agents or immunotherapies, and has developed an acquired resistance to the treatment, and/or developed bypass resistance to the treatment.

30. A compound that inhibits FAK, SRC, and JAK2, or a pharmaceutically acceptable salt thereof, in combination with a therapeutically effective amount of trametinib, for use in a method of treating cancer in a patient in need of such treatment.

31. A compound that inhibits FAK, SRC, and JAK2, or a pharmaceutically acceptable salt thereof, in combination with a therapeutically effective amount of trametinib, for use in a method of treating cancer in patient in need of such treatment, wherein at least one genetically altered oncogenic gene has been previously identified in the patient, the method comprising the step of administering to the patient a therapeutically effective amount of the compound that inhibits FAK, SRC, and JAK2 in combination with trametinib.

32. A compound that inhibits FAK, SRC, and JAK2, or a pharmaceutically acceptable salt thereof, in combination with a therapeutically effective amount of trametinib, for use in a method of treating a cancer mediated by at least one genetically altered oncogenic gene, in patient in need of such treatment, the method comprising the step of administering to the patient a therapeutically effective amount of the compound that inhibits FAK, SRC, and JAK2 in combination with trametinib.

33. A compound that inhibits FAK, SRC, and JAK2, or a pharmaceutically acceptable salt thereof, in combination with a therapeutically effective amount of trametinib, for use in a method of treating cancer in a patient comprising;
  i. identifying at least one genetically altered oncogenic gene in the patient, and
  ii. administering to the patient a therapeutically effective amount of the compound that inhibits FAK, SRC, and JAK2, in combination with trametinib.

34. The compound of any one of clauses 31 to 33, wherein the at least one genetically altered oncogenic gene is a genetically altered KRAS, a genetically altered NRAS, a genetically altered HRAS, a genetically altered BRAF, a genetically altered MEK, and/or a genetically altered PI3K.

35. A compound that inhibits FAK, SRC, and JAK2, or a pharmaceutically acceptable salt thereof, in combination with a therapeutically effective amount of trametinib, for use in a method of treating non-small cell lung cancer in patient in need of such treatment, the method comprising the step of administering to the patient a therapeutically effective amount of the compound that inhibits FAK, SRC, and JAK2 in combination with trametinib.

36. A compound that inhibits FAK, SRC, and JAK2, or a pharmaceutically acceptable salt thereof, in combination with a therapeutically effective amount of trametinib, for use in a method of treating non-small cell lung cancer in patient in need of such treatment, the method comprising the step of administering to the patient a therapeutically effective amount of a compound that inhibits FAK, SRC, and JAK2 in combination with trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

37. A compound that inhibits FAK, SRC, and JAK2, or a pharmaceutically acceptable salt thereof, in combination with a therapeutically effective amount of trametinib, for use in a method of treating non-small cell lung cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient a therapeutically effective amount of a compound that inhibits FAK, SRC, and JAK2 in combination with trametinib.

38. A compound that inhibits FAK, SRC, and JAK2, or a pharmaceutically acceptable salt thereof, in combination with a therapeutically effective amount of trametinib, for use in a method of treating non-small cell lung cancer in a patient comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient a therapeutically effective amount of the compound that inhibits FAK, SRC, and JAK2 in combination with trametinib.

39. The compound of any one of clauses 36 to 38, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H; or KRAS comprises at least one mutation that is not G12A, G12C, G12S, G12V, and Q61K.

40. A compound that inhibits FAK, SRC, and JAK2, or a pharmaceutically acceptable salt thereof, in combination with a therapeutically effective amount of trametinib, for use in a method for treating colorectal cancer or pancreatic cancer in a patient in need of such treatment, the method comprising the step of administering to the patient a therapeutically effective amount of the compound that inhibits FAK, SRC, and JAK2 in combination with trametinib.

41. A compound that inhibits FAK, SRC, and JAK2, or a pharmaceutically acceptable salt thereof, in combination with a therapeutically effective amount of trametinib, for use in a method of treating colorectal cancer or pancreatic cancer in patient in need of such treatment, the method comprising the step of administering to the patient a therapeutically effective amount of the compound that inhibits FAK, SRC, and JAK2 in combination with trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

42. A compound that inhibits FAK, SRC, and JAK2, or a pharmaceutically acceptable salt thereof, in combination with a therapeutically effective amount of trametinib, for use in a method of treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient a therapeutically effective amount of a compound that inhibits FAK, SRC, and JAK2 in combination with trametinib.

43. A compound that inhibits FAK, SRC, and JAK2, or a pharmaceutically acceptable salt thereof, in combination with a therapeutically effective amount of trametinib, for use in a method of treating colorectal cancer or pancreatic cancer in a patient comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient a therapeutically effective amount of the compound that inhibits FAK, SRC, and JAK2 in combination with trametinib.

44. The compound of any one of clauses 41 to 43, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

45. The compound of any one of clauses 30 to 44, wherein the compound that inhibits FAK, SRC, and JAK2 is administered in an amount of from about 40 mg to about 200 mg.

46. The compound of any one of clauses 30 to 45, wherein trametinib is administered in an amount of from about 0.5 mg to about 2.5 mg.

47. The compound of any one of clauses 30 to 46, wherein the compound that inhibits FAK, SRC and JAK2 is of the formula I

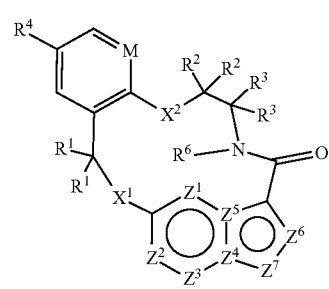

wherein
M is $CR^5$ or N;
$X^1$ and $X^2$ are independently —$C(R^7)(R^8)$—, —S—, —S(O)—, —S(O)$_2$—, —O— or —N($R^9$)—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O) O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OW;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

48. The compound of any one of clauses 30 to 47, wherein the compound that inhibits FAK, SRC and JAK2 is a compound of the formula

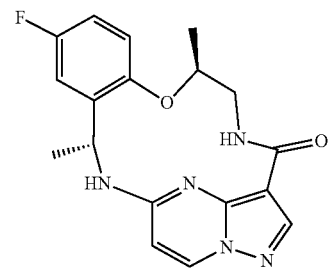

or a pharmaceutically acceptable salt thereof.

49. The compound of any one of clauses 30 to 48, wherein the compound that inhibits FAK, SRC and JAK2 is administered in an amount of about 40 mg, about 80 mg, about 120 mg, or about 160 mg.

50. The compound of any one of clauses 30 to 49, wherein trametinib is administered in an amount of about 1 mg or about 2 mg.

51. The compound of any one of clauses 30 to 50, wherein the compound that inhibits FAK, SRC and JAK2 is administered on a schedule of at least one dose of about 40 mg, about 80 mg QD, about 120 mg QD, or about 160 mg QD, followed by at least one dose of about 40 mg BID, about 80 mg BID, about 120 mg BID, or about 160 mg BID.

52. The compound of any one of clauses 30 to 51, wherein trametinib is administered in at least one dose of about 1 mg QD, or about 2 mg QD.

53. The compound of any one of clauses 30 to 52, wherein the compound that inhibits FAK, SRC and JAK2 is administered at the same time as trametinib.

54. The compound of any one of clauses 30 to 52, wherein the compound that inhibits FAK, SRC and JAK2 is administered prior to trametinib.

55. The compound of any one of clauses 30 to 52, wherein the compound that inhibits FAK, SRC and JAK2 is administered after trametinib.

56. The compound of any one of clauses 30 to 55, wherein the patient has not received a prior treatment.

57. The compound of any one of clauses 30 to 55, wherein the patient has received at least one prior treatment of one or more chemotherapeutic agents or immunotherapies.

58. The compound of any one of clauses 30 to 55 or 57, wherein the patient has received at least one prior treatment of one or more chemotherapeutic agents or immunotherapies, and has developed an acquired resistance to the treatment, and/or developed bypass resistance to the treatment.

59. Use of a compound that inhibits FAK, SRC and JAK2, or a pharmaceutically acceptable salt thereof, in the preparation of a medicament comprising a therapeutically effective amount of the compound that inhibits FAK, SRC, and JAK2, for treating cancer in a patient in combination with a therapeutically effective amount of trametinib.

60. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating cancer in a patient in combination with a therapeutically effective amount of trametinib, wherein at least one genetically altered oncogenic gene has been previously identified in the patient.

61. Use of compound that inhibits FAK, SRC, and JAK2, or a pharmaceutically acceptable salt thereof, in the preparation of a medicament comprising a therapeutically effective amount of the compound that inhibits FAK, SRC, and JAK2, for treating a cancer in a patient in combination with a therapeutically effective amount of trametinib, wherein the cancer is mediated by at least one genetically altered oncogenic gene.

62. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for use in a method of treating a cancer in a patient in combination with a therapeutically effective amount of trametinib, wherein the method comprises;
  i. identifying at least one genetically altered oncogenic gene in the patient, and
  ii. administering to the patient the medicament in combination with trametinib.

63. The use of any one of clauses 31 to 33, wherein the at least one genetically altered oncogenic gene is a genetically altered KRAS, a genetically altered NRAS, a genetically altered HRAS, a genetically altered BRAF, a genetically altered MEK, and/or a genetically altered PI3K.

64. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating non-small cell lung cancer in a patient in combination with a therapeutically effective amount of trametinib.

65. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating non-small cell lung cancer in a patient in combination with a therapeutically effective amount of trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

66. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating non-small cell lung cancer mediated by at least one genetically altered oncogenic gene selected from a genetically altered KRAS, a genetically altered NRAS, genetically altered HRAS, a genetically altered BRAF, a genetically altered MEK, or a genetically altered PI3K in a patient in combination with a therapeutically effective amount of trametinib.

67. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for use in a method of treating non-small cell lung cancer in a patient in combination with a therapeutically effective amount of trametinib, the method comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient the medicament in combination with trametinib.

68. The use of any one of clauses 65 to 67, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H; or KRAS comprises at least one mutation that is not G12A, G12C, G12S, G12V, and Q61K.

69. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating colorectal cancer or pancreatic cancer in a patient in combination with a therapeutically effective amount of trametinib.

70. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating colorectal cancer or pancreatic cancer in a patient in combination with a therapeutically effective amount of trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

71. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K in a patient in combination with a therapeutically effective amount of trametinib.

72. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for use in a method of treating colorectal cancer or pancreatic cancer in a patient in combination with a therapeutically effective amount of trametinib, the method comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient the medicament in combination with trametinib.

73. The use of any one of clauses 70 to 72, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

74. The use of any one of clauses 59 to 73, wherein the compound that inhibits FAK, SRC, and JAK2 is administered in an amount of from about 40 mg to about 200 mg.

75. The use of any one of clauses 59 to 74, wherein trametinib is administered in an amount of from about 0.5 mg to about 2.5 mg.

76. The use of any one of clauses 59 to 75, wherein the compound that inhibits FAK, SRC and JAK2 is of the formula I

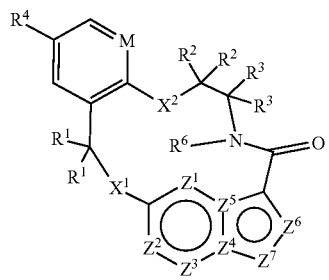

wherein
M is $CR^5$ or N;
$X^1$ and $X^2$ are independently —$C(R^7)(R^8)$—, —S—, —S(O)—, —S(O)$_2$—, —O— or —N(R$^9$)—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O) O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S (O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^7$ or —C(O)NR$^7$R$^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O) O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S (O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —CO$_2$$C_1$-$C_6$ alkyl, —CONH$_2$, —CONH($C_1$-$C_6$ alkyl), —CON($C_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O) O$C_1$-$C_6$ alkyl, —N($C_1$-$C_6$ alkyl)C(O)O$C_1$-$C_6$ alkyl, —NHS (O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OW;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

77. The use of any one of clauses 59 to 76, wherein the compound that inhibits FAK, SRC and JAK2 is a compound of the formula

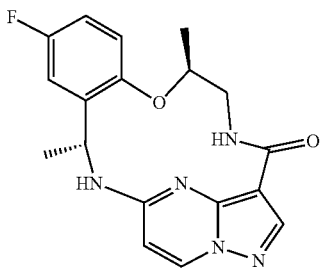 [SMILES: C[C@H]1CNC(=O)c2cnn3ccc(nc23)N[C@H](C)c2cc(F)ccc2O1]

or a pharmaceutically acceptable salt thereof.

78. The use of any one of clauses 59 to 77, wherein the compound that inhibits FAK, SRC and JAK2 is administered in an amount of about 40 mg, about 80 mg, about 120 mg, or about 160 mg.

79. The use of any one of clauses 59 to 78, wherein trametinib is administered in an amount of about 1 mg or about 2 mg.

80. The use of any one of clauses 59 to 79, wherein the compound that inhibits FAK, SRC and JAK2 is administered on a schedule of at least one dose of about 40 mg QD. about 80 mg QD, about 120 mg QD, or about 160 mg QD, followed by at least one dose of about 40 mg BID, about 80 mg BID, about 120 mg BID, or about 160 mg BID.

81. The use of any one of clauses 59 to 80, wherein trametinib is administered in at least one dose of about 1 mg QD, or about 2 mg QD.

82. The use of any one of clauses 59 to 81, wherein the compound that inhibits FAK, SRC and JAK2 is administered at the same time as trametinib.

83. The use of any one of clauses 59 to 81, wherein the compound that inhibits FAK, SRC and JAK2 is administered prior to trametinib.

84. The use of any one of clauses 59 to 81, wherein the compound that inhibits FAK, SRC and JAK2 is administered after trametinib.

85. The use of any one of clauses 59 to 84, wherein the patient has not received a prior treatment.

86. The use of any one of clauses 59 to 84, wherein the patient has received at least one prior treatment of one or more chemotherapeutic agents or immunotherapies.

87. The use of any one of clauses 59 to 84 or 86, wherein the patient has received at least one prior treatment of one or more chemotherapeutic agents or immunotherapies, and has developed an acquired resistance to the treatment, and/or developed bypass resistance to the treatment.

88. A medicament comprising a therapeutically effective amount of a compound that inhibits FAK, SRC and JAK2, or a pharmaceutically acceptable salt thereof, combined with a therapeutically effective amount of trametinib, in fixed or free combination.

89. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect on a cancer in a patient, wherein at least one genetically altered oncogenic gene has been previously identified in the patient.

90. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect on a cancer mediated by at least one genetically altered oncogenic gene.

91. The medicament of clause 89 or 90, wherein the at least one genetically altered oncogenic gene is a genetically altered KRAS, a genetically altered NRAS, a genetically altered BRAF, a genetically altered MEK, and/or a genetically altered PI3K.

92. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect for treating non-small cell lung cancer.

93. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect for treating non-small cell lung cancer in a patient, wherein at least one genetically altered oncogenic gene selected from a genetically altered KRAS, a genetically altered NRAS, a genetically altered BRAF, a genetically altered MEK, or a genetically altered PI3K has been previously identified in the patient.

94. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect for treating non-small cell lung cancer mediated by at least one genetically altered oncogenic gene selected from a genetically altered KRAS, a genetically altered NRAS, a genetically altered BRAF, a genetically altered MEK, or a genetically altered PI3K in a patient.

95. The medicament of clause 93 or 94, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R, or selected from the group consisting of G12D, G13D, and Q61H; or KRAS comprises at least one mutation that is not G12A, G12C, G12S, G12V, and Q61K.

96. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect for treating colorectal cancer or pancreatic cancer in a patient.

97. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect for treating colorectal cancer or pancreatic cancer in a patient, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

98. A medicament comprising a therapeutically effective amount of a compound that inhibits FAK, SRC, and JAK2, or a pharmaceutically acceptable salt thereof, combined with a therapeutically effective amount of trametinib, in fixed or free combination, wherein the medicament provides a synergistic effect for treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K in a patient.

99. The medicament of clause 97 or 98, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

100. The medicament of any one of clauses 88 to 99, wherein the compound that inhibits FAK, SRC, and JAK2 is provided in the medicament in an amount of from about 40 mg to about 200 mg.

101. The medicament of any one of clauses 88 to 100, wherein trametinib is provided in the medicament in an amount of from about 0.5 mg to about 2.5 mg.

102. The medicament of any one of clauses 88 to 101, wherein the compound that inhibits FAK, SRC and JAK2 is of the formula I

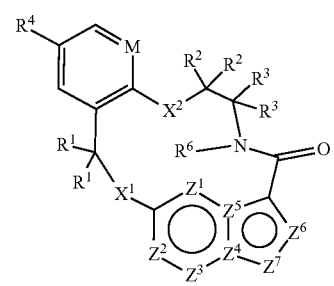

wherein
M is $CR^5$ or N;
$X^1$ and $X^2$ are independently —C($R^7$)($R^8$)—, —S—, —S(O)—, —S(O)$_2$—, —O— or —N($R^9$)—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O) O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S (O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;
each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O) O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

R$^4$ and R$^5$ are each independently H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —CO$_2$C$_1$-C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OW;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

103. The medicament of any one of clauses 88 to 102, wherein the compound that inhibits FAK, SRC and JAK2 is a compound of the formula

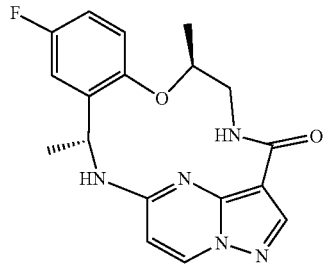

or a pharmaceutically acceptable salt thereof.

104. The medicament of any one of clauses 88 to 103, wherein the compound that inhibits FAK, SRC and JAK2 is provided in the medicament in an amount of about 40 mg, about 80 mg, about 120 mg, or about 160 mg.

105. The medicament of any one of clauses 88 to 104, wherein trametinib is provided in the medicament in an amount of about 1 mg or about 2 mg.

106. The medicament of any one of clauses 88 to 105, wherein the compound that inhibits FAK, SRC and JAK2 is provided in the medicament on a schedule of at least one dose of about 40 mg QD, about 80 mg QD, about 120 mg QD, or about 160 mg QD, followed by at least one dose of about 40 mg BID, about 80 mg BID, about 120 mg BID, or about 160 mg BID.

107. The medicament of any one of clauses 88 to 106, wherein trametinib is provided in the medicament for administration in at least one dose of about 1 mg QD, or about 2 mg QD.

108. The medicament of any one of clauses 88 to 107, wherein the compound that inhibits FAK, SRC and JAK2 is provided at the same time as trametinib.

109. The medicament of any one of clauses 88 to 107, in free combination, wherein the compound that inhibits FAK, SRC and JAK2 is provided prior to trametinib.

110. The medicament of any one of clauses 88 to 107, in free combination, wherein the compound that inhibits FAK, SRC and JAK2 is provided after trametinib.

111. The medicament of any one of clauses 88 to 110, wherein the patient has not received a prior treatment.

112. The medicament of any one of clauses 88 to 110, wherein the patient has received at least one prior treatment of one or more chemotherapeutic agents or immunotherapies.

113. The medicament of any one of clauses 88 to 110 or 112, wherein the patient has received at least one prior treatment of one or more chemotherapeutic agents or immunotherapies, and has developed an acquired resistance to the treatment, and/or developed bypass resistance to the treatment.

114. A synergistic composition of a compound that inhibits FAK, SRC and JAK2 and trametinib, where the two components come into contact with each other at a locus.

115. The synergistic composition of clause 114, wherein the compound that inhibits FAK, SRC and JAK2 is of the formula I

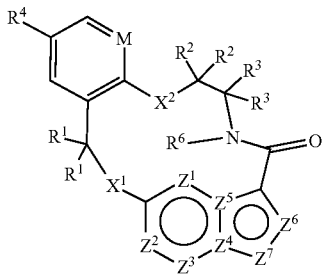

I wherein

M is CR⁵ or N;

X¹ and X² are independently —C(R⁷)(R⁸)—, —S—, —S(O)—, —S(O)₂—, —O— or —N(R⁹)—;

each R¹ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR⁷ or —C(O)NR⁷R⁸; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH₂, —NH($C_1$-$C_6$ alkyl), —N($C_1$-$C_6$ alkyl)₂, —NHC(O)$C_1$-$C_6$ alkyl, —N($C_1$-$C_6$ alkyl)C(O)$C_1$-$C_6$ alkyl, —NHC(O)NH₂, —NHC(O)NH$C_1$-$C_6$ alkyl, —N($C_1$-$C_6$ alkyl)C(O)NH₂, —N($C_1$-$C_6$ alkyl)C(O)NH$C_1$-$C_6$ alkyl, —NHC(O)N($C_1$-$C_6$ alkyl)₂, —N($C_1$-$C_6$ alkyl)C(O)N($C_1$-$C_6$ alkyl)₂, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)₂($C_1$-$C_6$ alkyl), —N($C_1$-$C_6$ alkyl)S(O)($C_1$-$C_6$ alkyl), —N($C_1$-$C_6$ alkyl)S(O)₂($C_1$-$C_6$ alkyl), —NHS(O)NH₂, NHS(O)₂NH₂, —N($C_1$-$C_6$ alkyl)S(O)NH₂, —N($C_1$-$C_6$ alkyl)S(O)₂NH₂, —NHS(O)NH($C_1$-$C_6$ alkyl), —NHS(O)₂NH($C_1$-$C_6$ alkyl), —NHS(O)N($C_1$-$C_6$ alkyl)₂, —NHS(O)₂N($C_1$-$C_6$ alkyl)₂, —N($C_1$-$C_6$ alkyl)S(O)NH($C_1$-$C_6$ alkyl), —N($C_1$-$C_6$ alkyl)S(O)₂NH($C_1$-$C_6$ alkyl), —N($C_1$-$C_6$ alkyl)S(O)N($C_1$-$C_6$ alkyl)₂, —N($C_1$-$C_6$ alkyl)S(O)₂N($C_1$-$C_6$ alkyl)₂, —CO₂H, —C(O)O$C_1$-$C_6$ alkyl, —C(O)NH₂, —C(O)NH($C_1$-$C_6$ alkyl), —C(O)N($C_1$-$C_6$ alkyl)₂, —S$C_1$-$C_6$ alkyl, —S(O)$C_1$-$C_6$ alkyl, —S(O)₂$C_1$-$C_6$ alkyl, —S(O)NH($C_1$-$C_6$ alkyl), —S(O)₂NH($C_1$-$C_6$ alkyl), —S(O)N($C_1$-$C_6$ alkyl)₂, —S(O)₂N($C_1$-$C_6$ alkyl)₂, —P($C_1$-$C_6$ alkyl)₂, —P(O)($C_1$-$C_6$ alkyl)₂, $C_3$-$C_6$ cycloalkyl, or 3- to 7-membered heterocycloalkyl;

each R² and R³ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR⁷ or —C(O)NR⁷R⁸; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH₂, —NH($C_1$-$C_6$ alkyl), —N($C_1$-$C_6$ alkyl)₂, NHC(O)$C_1$-$C_6$ alkyl, —N($C_1$-$C_6$ alkyl)C(O)$C_1$-$C_6$ alkyl, —NHC(O)NH₂, —NHC(O)NH$C_1$-$C_6$ alkyl, —N($C_1$-$C_6$ alkyl)C(O)NH₂, —N($C_1$-$C_6$ alkyl)C(O)NH$C_1$-$C_6$ alkyl, —NHC(O)N($C_1$-$C_6$ alkyl)₂, —N($C_1$-$C_6$ alkyl)C(O)N($C_1$-$C_6$ alkyl)₂, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)₂($C_1$-$C_6$ alkyl), —N($C_1$-$C_6$ alkyl)S(O)($C_1$-$C_6$ alkyl), —N($C_1$-$C_6$ alkyl)S(O)₂($C_1$-$C_6$ alkyl), —NHS(O)NH₂, NHS(O)₂NH₂, —N($C_1$-$C_6$ alkyl)S(O)NH₂, —N($C_1$-$C_6$ alkyl)S(O)₂NH₂, —NHS(O)NH($C_1$-$C_6$ alkyl), —NHS(O)₂NH($C_1$-$C_6$ alkyl), —NHS(O)N($C_1$-$C_6$ alkyl)₂, —NHS(O)₂N($C_1$-$C_6$ alkyl)₂, —N($C_1$-$C_6$ alkyl)S(O)NH($C_1$-$C_6$ alkyl), —N($C_1$-$C_6$ alkyl)S(O)₂NH($C_1$-$C_6$ alkyl), —N($C_1$-$C_6$ alkyl)S(O)N($C_1$-$C_6$ alkyl)₂, —N($C_1$-$C_6$ alkyl)S(O)₂N($C_1$-$C_6$ alkyl)₂, —CO₂H, —C(O)O$C_1$-$C_6$ alkyl, —C(O)NH₂, —C(O)NH($C_1$-$C_6$ alkyl), —C(O)N($C_1$-$C_6$ alkyl)₂, —S$C_1$-$C_6$ alkyl, —S(O)$C_1$-$C_6$ alkyl, —S(O)₂$C_1$-$C_6$ alkyl, —S(O)NH($C_1$-$C_6$ alkyl), —S(O)₂NH($C_1$-$C_6$ alkyl), —S(O)N($C_1$-$C_6$ alkyl)₂, —S(O)₂N($C_1$-$C_6$ alkyl)₂, —P($C_1$-$C_6$ alkyl)₂, —P(O)($C_1$-$C_6$ alkyl)₂, $C_3$-$C_6$ cycloalkyl, or 3- to 7-membered heterocycloalkyl;

R⁴ and R⁵ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)₂ or —CF₃;

R⁶ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH₂, —NH($C_1$-$C_6$ alkyl), —N($C_1$-$C_6$ alkyl)₂, —CO₂H, —CO₂$C_1$-$C_6$ alkyl, —CONH₂, —CONH($C_1$-$C_6$ alkyl), —CON($C_1$-$C_6$ alkyl)₂, $C_3$-$C_6$ cycloalkyl, or 3- to 7-membered heterocycloalkyl;

each R⁷ and R⁸ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH₂, —NH($C_1$-$C_6$ alkyl), —N($C_1$-$C_6$ alkyl)₂, —NHC(O)$C_1$-$C_6$ alkyl, —N($C_1$-$C_6$ alkyl)C(O)$C_1$-$C_6$ alkyl, —NHC(O)NH₂, —NHC(O)NH$C_1$-$C_6$ alkyl, —N($C_1$-$C_6$ alkyl)C(O)NH₂, —N($C_1$-$C_6$ alkyl)C(O)NH$C_1$-$C_6$ alkyl, —NHC(O)N($C_1$-$C_6$ alkyl)₂, —N($C_1$-$C_6$ alkyl)C(O)N($C_1$-$C_6$ alkyl)₂, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)₂($C_1$-$C_6$ alkyl), —N($C_1$-$C_6$ alkyl)S(O)($C_1$-$C_6$ alkyl), —N($C_1$-$C_6$ alkyl)S(O)₂($C_1$-$C_6$ alkyl), —NHS(O)NH₂, NHS(O)₂NH₂, —N($C_1$-$C_6$ alkyl)S(O)NH₂, —N($C_1$-$C_6$ alkyl)S(O)₂NH₂, —NHS(O)NH($C_1$-$C_6$ alkyl), —NHS(O)₂NH($C_1$-$C_6$ alkyl), —NHS(O)N($C_1$-$C_6$ alkyl)₂, —NHS(O)₂N($C_1$-$C_6$ alkyl)₂, —N($C_1$-$C_6$ alkyl)S(O)NH($C_1$-$C_6$ alkyl), —N($C_1$-$C_6$ alkyl)S(O)₂NH($C_1$-$C_6$ alkyl), —N($C_1$-$C_6$ alkyl)S(O)N($C_1$-$C_6$ alkyl)₂, —N($C_1$-$C_6$ alkyl)S(O)₂N($C_1$-$C_6$ alkyl)₂, —CO₂H, —C(O)O$C_1$-$C_6$ alkyl, —C(O)NH₂, —C(O)NH($C_1$-$C_6$ alkyl), —C(O)N($C_1$-$C_6$ alkyl)₂, —S$C_1$-$C_6$ alkyl, —S(O)$C_1$-$C_6$ alkyl, —S(O)₂$C_1$-$C_6$ alkyl, —S(O)NH($C_1$-$C_6$ alkyl), —S(O)₂NH($C_1$-$C_6$ alkyl), —S(O)N($C_1$-$C_6$ alkyl)₂, —S(O)₂N($C_1$-$C_6$ alkyl)₂, —P($C_1$-$C_6$ alkyl)₂, —P(O)($C_1$-$C_6$ alkyl)₂, $C_3$-$C_6$ cycloalkyl, or 3- to 7-membered heterocycloalkyl;

each R⁹ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OW;

each Z¹, Z², Z³, Z⁴, Z⁵, Z⁶ or Z⁷ is independently N, NH, or C(R¹⁰), wherein each R¹⁰ is independently H, deuterium, halogen, $C_1$-$C_6$ alkyl, —O—$C_1$-$C_6$ alkyl, —OH, —NH₂, —NH($C_1$-$C_6$ alkyl), —NH(phenyl), —NH(heteroaryl), —CN, or CF₃, and provided that at least one of Z¹, Z², Z³, Z⁴, Z⁵, Z⁶ or Z⁷ is N or NH;

or a pharmaceutically acceptable salt thereof.

116. The synergistic composition of clause 114 or 115, wherein the compound that inhibits FAK, SRC and JAK2 is a compound of the formula

[chemical structure]

or a pharmaceutically acceptable salt thereof.

117. The synergistic composition of any one of clauses 114 to 116, wherein the locus is a cancer or a cancer cell.

118. The synergistic composition of any one of clauses 114 to 117, wherein the locus is a cancer selected from non-small cell lung cancer, colorectal cancer or pancreatic cancer and pancreatic cancer.

119. The synergistic composition of clause 118, wherein the cancer is non-small cell lung cancer.

120. The synergistic composition of clause 118, wherein the cancer is colorectal cancer or pancreatic cancer.

121. The synergistic composition of any one of clauses 114 to 120, wherein the locus comprises at least one genetically altered oncogenic gene selected from a genetically altered KRAS, a genetically altered NRAS, a genetically altered HRAS, a genetically altered BRAF, a genetically altered MEK, or a genetically altered PI3K.

122. The synergistic composition of any one of clauses 114 to 121, wherein the locus comprises a genetically altered KRAS having at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12A, G12C, G12D, G12S, G12V, G13D, Q61H, and Q61K, or selected from the group consisting of G12D, G13D, and Q61H; or selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S; or KRAS comprises at least one mutation that is not G12A, G12C, G12S, G12V, and Q61K.

123. The synergistic composition of any one of clauses 114 to 122, wherein the compound that inhibits FAK, SRC, and JAK2 is provided in the composition in an amount of from about 40 mg to about 200 mg.

124. The synergistic composition of any one of clauses 114 to 123, wherein trametinib is provided in the composition in an amount of from about 0.5 mg to about 2.5 mg.

125. The synergistic composition of any one of clauses 114 to 124, wherein the compound that inhibits FAK, SRC and JAK2 is provided in the composition in an amount of about 40 mg, about 80 mg, about 120 mg, or about 160 mg.

126. The synergistic composition of any one of clauses 114 to 125, wherein trametinib is provided in the composition in an amount of about 1 mg or about 2 mg.

127. A synergistic composition of a compound that inhibits FAK, SRC and JAK2 and trametinib, where the two components come into contact with each other only in the human body.

128. The synergistic composition of clause 127, wherein the compound that inhibits FAK, SRC and JAK2 is of the formula I

[chemical structure]

wherein
M is $CR^5$ or N;
$X^1$ and $X^2$ are independently —$C(R^7)(R^8)$—, —S—, —S(O)—, —S(O)$_2$—, —O— or —N($R^9$)—;
each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —P(C₁-C₆ alkyl)₂, —P(O)(C₁-C₆ alkyl)₂, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —OC₁-C₆ alkyl, —NHC₁-C₆ alkyl, —N(C₁-C₆ alkyl)₂ or —CF₃;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —OC₁-C₆ alkyl, —NH₂, —NH(C₁-C₆ alkyl), —N(C₁-C₆ alkyl)₂, —CO₂H, —CO₂C₁-C₆ alkyl, —CONH₂, —CONH(C₁-C₆ alkyl), —CON(C₁-C₆ alkyl)₂, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —OC₁-C₆ alkyl, —NH₂, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)NH₂, —NHC(O)NHC₁-C₆ alkyl, —N(C₁-C₆ alkyl)C(O)NH₂, —N(C₁-C₆ alkyl)C(O)NHC₁-C₆ alkyl, —NHC(O)N(C₁-C₆ alkyl)₂, —N(C₁-C₆ alkyl)C(O)N(C₁-C₆ alkyl)₂, —NHC(O)OC₁-C₆ alkyl, —N(C₁-C₆ alkyl)C(O)OC₁-C₆ alkyl, —NHS(O)(C₁-C₆ alkyl), —NHS(O)₂(C₁-C₆ alkyl), —N(C₁-C₆ alkyl)S(O)(C₁-C₆ alkyl), —N(C₁-C₆ alkyl)S(O)₂(C₁-C₆ alkyl), —NHS(O)NH₂, NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —P(C₁-C₆ alkyl)₂, —P(O)(C₁-C₆ alkyl)₂, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OW;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —NH₂, —NH(C₁-C₆ alkyl), —NH(phenyl), —NH(heteroaryl), —CN, or —CF₃, and provided that at least one of $Z^1$, $Z^2$, $Z^3$, $Z^4$, $Z^5$, $Z^6$ or $Z^7$ is N or NH;

or a pharmaceutically acceptable salt thereof.

129. The synergistic composition of clause 127 or 128, wherein the compound that inhibits FAK, SRC and JAK2 is a compound of the formula

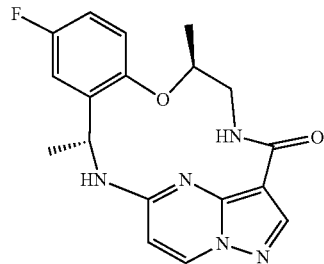

or a pharmaceutically acceptable salt thereof.

130. The synergistic composition of any one of clauses 127 to 129, wherein the human body comprises at least one genetically altered oncogenic gene selected from a genetically altered KRAS, a genetically altered NRAS, a genetically altered BRAF, a genetically altered MEK, or a genetically altered PI3K.

131. The synergistic composition of any one of clauses 127 to 130, wherein the human body comprises a genetically altered KRAS having at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12A, G12C, G12D, G12S, G12V, G13D, Q61H, and Q61K, or selected from the group consisting of G12D, G13D, and Q61H; or selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S; or KRAS comprises at least one mutation that is not G12A, G12C, G12S, G12V, and Q61K.

132. The synergistic composition of any one of clauses 127 to 131, wherein the compound that inhibits FAK, SRC, and JAK2 is provided in the composition in an amount of from about 40 mg to about 200 mg.

133. The synergistic composition of any one of clauses 127 to 132, wherein trametinib is provided in the composition in an amount of from about 0.5 mg to about 2.5 mg.

134. The synergistic composition of any one of clauses 127 to 133, wherein the compound that inhibits FAK, SRC and JAK2 is provided in the composition in an amount of about 40 mg, about 80 mg, about 120 mg, or about 160 mg.

135. The synergistic composition of any one of clauses 127 to 134, wherein trametinib is provided in the composition in an amount of about 1 mg or about 2 mg.

136. The synergistic composition of any one of clauses 127 to 135, wherein the human body has not received a prior treatment.

137. The synergistic composition of any one of clauses 127 to 135, wherein the human body has received at least one prior treatment of one or more chemotherapeutic agents or immunotherapies.

138. The synergistic composition of any one of clauses 127 to 135 or 137, wherein the host animal is a human patient in need of such treatment who has received at least one prior treatment of one or more chemotherapeutic agents or immunotherapies, and developed an acquired resistance to the treatment or developed bypass resistance to the treatment.

139. A method of treating cancer in a patient in need of such treatment, the method comprising the step of administering to the patient a therapeutically effective amount of a compound that inhibits FAK, SRC, and JAK2, in combination with a therapeutically effective amount of a MEK inhibitor, provided that the MEK inhibitor is not trametinib.

140. A method of treating cancer in patient in need of such treatment, the method comprising the step of administering to the patient having cancer a therapeutically effective amount of a compound that inhibits FAK, SRC, and JAK2, in combination with a therapeutically effective amount of a MEK inhibitor, provided that the MEK inhibitor is not trametinib, wherein at least one genetically altered oncogenic gene has been previously identified in the patient.

141. A method of treating a cancer mediated by at least one genetically altered oncogenic gene, in patient in need of such treatment, the method comprising the step of administering to the patient having cancer a therapeutically effective amount of a compound that inhibits FAK, SRC, and JAK2, in combination with a therapeutically effective amount of a MEK inhibitor, provided that the MEK inhibitor is not trametinib.

142. A method of treating cancer in a patient comprising;
  i. identifying at least one genetically altered oncogenic gene in the patient, and
  ii. administering to the patient a therapeutically effective amount of a compound that inhibits FAK, SRC, and JAK2, in combination with a therapeutically effective amount of a MEK inhibitor, provided that the MEK inhibitor is not trametinib.

143. The method of any one of clauses 140 to 142, wherein the at least one genetically altered oncogenic gene is a genetically altered KRAS, a genetically altered NRAS, a genetically altered HRAS, a genetically altered BRAF, a genetically altered MEK, and/or a genetically altered PI3K.

144. A method of treating non-small cell lung cancer in patient in need of such treatment, the method comprising the step of administering to the patient having non-small cell lung cancer a therapeutically effective amount of a compound that inhibits FAK, SRC, and JAK2, in combination with a therapeutically effective amount of a MEK inhibitor, provided that the MEK inhibitor is not trametinib.

145. A method of treating non-small cell lung cancer in patient in need of such treatment, the method comprising the step of administering to the patient having cancer a therapeutically effective amount of a compound that inhibits FAK, SRC, and JAK2, in combination with a therapeutically effective amount of a MEK inhibitor, provided that the MEK inhibitor is not trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

146. A method of treating non-small cell lung cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient having non-small cell lung cancer a therapeutically effective amount of a compound that inhibits FAK, SRC, and JAK2, in combination with a therapeutically effective amount of a MEK inhibitor, provided that the MEK inhibitor is not trametinib.

147. A method of treating non-small cell lung cancer in a patient comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient a therapeutically effective amount of a compound that inhibits FAK, SRC, and JAK2, in combination with a therapeutically effective amount of a MEK inhibitor, provided that the MEK inhibitor is not trametinib.

148. The method of any one of clauses 145 to 147, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H.

149. A method for treating colorectal cancer or pancreatic cancer in a patient in need of such treatment, the method comprising the step of administering to the patient a therapeutically effective amount of a compound that inhibits FAK, SRC, and JAK2, in combination with a therapeutically effective amount of a MEK inhibitor, provided that the MEK inhibitor is not trametinib.

150. A method of treating colorectal cancer or pancreatic cancer in patient in need of such treatment, the method comprising the step of administering to the patient having cancer a therapeutically effective amount of a compound that inhibits FAK, SRC, and JAK2, in combination with a therapeutically effective amount of a MEK inhibitor, provided that the MEK inhibitor is not trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

151. A method of treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient having colorectal cancer or pancreatic cancer a therapeutically effective amount of a compound that inhibits FAK, SRC, and JAK2, in combination with a therapeutically effective amount of a MEK inhibitor, provided that the MEK inhibitor is not trametinib.

152. A method of treating colorectal cancer or pancreatic cancer in a patient comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient a therapeutically effective amount of a compound that inhibits FAK, SRC, and JAK2, in combination with a therapeutically effective amount of a MEK inhibitor, provided that the MEK inhibitor is not trametinib.

153. The method of any one of clauses 150 to 152, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

154. The method of any one of the preceding clauses, wherein the compound that inhibits FAK, SRC, and JAK2 is administered in an amount of from about 40 mg to about 200 mg.

155. The method of any one of the preceding clauses, wherein the compound that inhibits FAK, SRC, and JAK2 is administered in an amount of about 40 mg, or about 80 mg, or about 120 mg, or about 160 mg.

156. The method of any one of the preceding clauses, wherein the compound that inhibits FAK, SRC and JAK2 is of the formula I

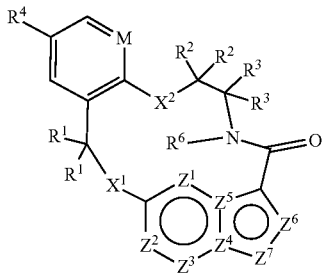

wherein
M is $CR^5$ or N;
$X^1$ and $X^2$ are independently —C($R^7$)($R^8$)—, —S—, —S(O)—, —S(O)$_2$—, —O— or —N($R^9$)—;
each $R^1$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, N($C_1$-$C_6$ alkyl)S(O)$_2$NH$_2$, —NHS(O)NH($C_1$-$C_6$ alkyl), —NHS(O)$_2$NH($C_1$-$C_6$ alkyl), NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), C(O)N($C_1$-$C_6$ alkyl)$_2$, S$C_1$-$C_6$ alkyl, —S(O)$C_1$-$C_6$ alkyl, —S(O)$_2$$C_1$-$C_6$ alkyl, S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, N($C_1$-$C_6$ alkyl)C(O)O$C_1$-$C_6$ alkyl), —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, N($C_1$-$C_6$ alkyl)S(O)NH$_2$, —N($C_1$-$C_6$ alkyl)S(O)$_2$NH$_2$, —NHS(O)NH($C_1$-$C_6$ alkyl), NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, C(O)NH$_2$, C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, CO$_2$$C_1$$C_6$ alkyl, —CONH$_2$, —CONH($C_1$-$C_6$ alkyl), —CON($C_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), NHS(O)$_2$($C_1$-$C_6$ alkyl), —N($C_1$-$C_6$ alkyl)S(O)($C_1$-$C_6$ alkyl), N($C_1$-$C_6$ alkyl)S(O)$_2$($C_1$-$C_6$ alkyl), NHS(O)NH$_2$, NHS(O)$_2$NH$_2$, —N($C_1$-$C_6$ alkyl)S(O)NH$_2$, N($C_1$-$C_6$ alkyl)S(O)$_2$NH$_2$, NHS(O)NH($C_1$-$C_6$ alkyl), —NHS(O)$_2$NH($C_1$-$C_6$ alkyl), NHS(O)N($C_1$-$C_6$ alkyl)$_2$, NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, C(O)O$C_1$-$C_6$ alkyl, —C(O)NH$_2$, —C(O)NH($C_1$-$C_6$ alkyl), —C(O)N($C_1$-$C_6$ alkyl)$_2$, S$C_1$-$C_6$ alkyl, S(O)$C_1$-$C_6$ alkyl, —S(O)$_2$$C_1$-$C_6$ alkyl, S(O)NH($C_1$-$C_6$ alkyl), —S(O)$_2$NH($C_1$-$C_6$ alkyl), S(O)N($C_1$-$C_6$ alkyl)$_2$, —S(O)$_2$N($C_1$-$C_6$ alkyl)$_2$, P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OW;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —$NH_2$, —NH($C_1$-$C_6$ alkyl), —NH(phenyl), —NH(heteroaryl), —CN, or —$CF_3$, and provided that at least one of $Z^1$, $Z^2$, $Z^3$, $Z^4$, $Z^5$, $Z^6$ or $Z^7$ is N or NH;

or a pharmaceutically acceptable salt thereof.

157. The method of any one of the preceding clauses, wherein the compound that inhibits FAK, SRC and JAK2 is a compound of the formula

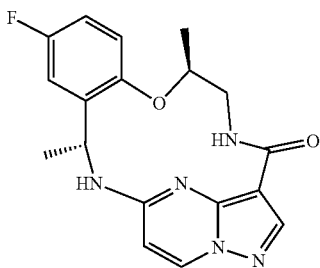 [SMILES: C[C@H]1CNC(=O)c2cnn3ccc(nc23)N[C@H](C)c2cc(F)ccc2O1]

or a pharmaceutically acceptable salt thereof.

158. The method according to any one of the preceding clauses, wherein the compound that inhibits FAK, SRC and JAK2 is administered in an amount of about 40 mg, about 80 mg, about 120 mg, or about 160 mg by once a day or twice a day.

159. The method according to any one of the preceding clauses, wherein the MEK inhibitor is pimasertib, selumetinib, cobimetinib, PD-0325901, refametinib, TAK733, MEK162, RO5126766, WX-554, RO4987655, GDC-0973, AZD8330, AZD6244, or CI-1040.

160. The method according to any one of the preceding clauses, wherein the compound that inhibits FAK, SRC and JAK2 is administered on a schedule of at least one dose of about 40 mg, about 80 mg QD, about 120 mg QD, or about 160 mg QD, followed by at least one dose of about 40 mg BID, about 80 mg BID, about 120 mg BID, or about 160 mg BID.

161. The method according to any one of the preceding clauses, wherein the MEK inhibitor is selumetinib.

162. The method according to any one of the preceding clauses, wherein the compound that inhibits FAK, SRC and JAK2 is administered at the same time as the MEK inhibitor.

163. The method according to any one of clauses 139 to 161, wherein the compound that inhibits FAK, SRC and JAK2 is administered prior to the MEK inhibitor.

164. The method according to any one of clauses 139 to 161, wherein the compound that inhibits FAK, SRC and JAK2 is administered after the MEK inhibitor.

165. The method according to any one of the preceding clauses, wherein the patient has not received a prior treatment.

166. The method according to any one of clauses 1 to 164, wherein the patient has received at least one prior treatment of one or more chemotherapeutic agents or immunotherapies.

167. The method according to any one of clauses 1 to 164 or 166, wherein the patient has received at least one prior treatment of one or more chemotherapeutic agents or immunotherapies, and has developed an acquired resistance to the treatment, and/or developed bypass resistance to the treatment.

168. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating cancer in a patient in need of such treatment.

169. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating cancer in patient in need of such treatment, wherein at least one genetically altered oncogenic gene has been previously identified in the patient, the method comprising the step of administering to the patient a therapeutically effective amount of the compound that inhibits FAK, SRC, and JAK2 in combination with a MEK inhibitor, provided that the MEK inhibitor is not trametinib.

170. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating a cancer mediated by at least one genetically altered oncogenic gene, in patient in need of such treatment, the method comprising the step of administering to the patient a therapeutically effective amount of the compound that inhibits FAK, SRC, and JAK2 in combination with a MEK inhibitor, provided that the MEK inhibitor is not trametinib.

171. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating cancer in a patient comprising;
  i. identifying at least one genetically altered oncogenic gene in the patient, and
  ii. administering to the patient a therapeutically effective amount of the compound that inhibits FAK, SRC, and JAK2, in combination with a MEK inhibitor, provided that the MEK inhibitor is not trametinib.

172. The compound of any one of clauses 169 to 171, wherein the at least one genetically altered oncogenic gene is a genetically altered KRAS, a genetically altered NRAS, a genetically altered HRAS, a genetically altered BRAF, a genetically altered MEK, and/or a genetically altered PI3K.

173. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating non-small cell lung cancer in patient in need of such treatment, the method comprising the step of administering to the patient a therapeutically effective amount of the compound that inhibits FAK, SRC, and JAK2 in combination with a MEK inhibitor, provided that the MEK inhibitor is not trametinib.

174. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating non-small cell lung cancer in patient in need of such treatment, the method comprising the step of administering to the patient a therapeutically effective amount of a compound that inhibits FAK, SRC, and JAK2 in combination with a MEK inhibitor, provided that the MEK inhibitor is not trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

175. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating non-small cell lung cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient a therapeutically effective amount of a compound that inhibits FAK, SRC, and JAK2 in combination with a MEK inhibitor, provided that the MEK inhibitor is not trametinib.

176. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating non-small cell lung cancer in a patient comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient a therapeutically effective amount of the compound that inhibits FAK, SRC, and JAK2 in combination with a MEK inhibitor, provided that the Mek inhibitor is not trametinib.

177. The compound of any one of clauses 174 to 176, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H.

178. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method for treating colorectal cancer or pancreatic cancer in a patient in need of such treatment, the method comprising the step of administering to the patient a therapeutically effective amount of the compound that inhibits FAK, SRC, and JAK2 in combination with a MEK inhibitor, provided that the MEK inhibitor is not trametinib.

179. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating colorectal cancer or pancreatic cancer in patient in need of such treatment, the method comprising the step of administering to the patient a therapeutically effective amount of the compound that inhibits FAK, SRC, and JAK2 in combination with a MEK inhibitor, provided that the MEK inhibitor is not trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

180. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K, in patient in need of such treatment, the method comprising the step of administering to the patient a therapeutically effective amount of a compound that inhibits FAK, SRC, and JAK2 in combination with a MEK inhibitor, provided that the MEK inhibitor is not trametinib.

181. A compound that inhibits FAK, SRC, and JAK2, or a pharmaceutically acceptable salt thereof, in combination with a therapeutically effective amount of a MEK inhibitor, provided that the MEK inhibitor is not trametinib, for use in a method of treating colorectal cancer or pancreatic cancer in a patient comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient a therapeutically effective amount of the compound that inhibits FAK, SRC, and JAK2 in combination with a MEK inhibitor, provided that the MEK inhibitor is not trametinib.

182. The compound of any one of clauses 179 to 181, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

183. The compound of any one of clauses 168 to 182, wherein the compound that inhibits FAK, SRC, and JAK2 is administered in an amount of from about 40 mg to about 200 mg.

184. The compound of any one of clauses 168 to 183, wherein the compound that inhibits FAK, SRC, and JAK2 is administered in an amount of about 40 mg, or about 80 mg, or about 120 mg, or about 160 mg.

185. The compound of any one of clauses 168 to 184, wherein the compound that inhibits FAK, SRC and JAK2 is of the formula I

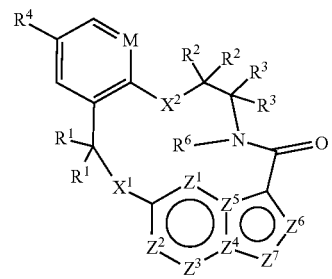

wherein
M is $CR^5$ or N;
$X^1$ and $X^2$ are independently —C($R^7$)($R^8$)—, —S—, —S(O)—, —S(O)$_2$—, —O— or —N($R^9$)—;
each $R^1$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2C_6$ alkynyl, $C_3$-$C_6$ cycloalkyl and $C_6$-$C_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), N(C$_1$-C$_6$ alkyl)S(O)$_2$(C$_1$-C$_6$ alkyl), —NHS(O)NH$_2$, NHS(O)$_2$NH$_2$, —N(C$_1$-C$_6$ alkyl)S(O)NH$_2$, N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), C(O)N(C$_1$-C$_6$ alkyl)$_2$, SC$_1$-C$_6$ alkyl, —S(O)C$_1$-C$_6$ alkyl, —S(O)$_2$C$_1$-C$_6$ alkyl, S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, C(O)NH$_2$, C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, S(O)$_2$C$_1$-C$_6$ alkyl, S(O)NH(C$_1$-C$_6$ alkyl), —S(O)$_2$NH(C$_1$-C$_6$ alkyl), —S(O)N(C$_1$-C$_6$ alkyl)$_2$, S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7 membered heterocycloalkyl;

R$^4$ and R$^5$ are each independently H, fluoro, chloro, bromo, C$_1$-C$_6$ alkyl, —OH, —CN, OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, CO$_2$C$_1$C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$C$_6$ alkenyl, C$_2$C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), NHS(O)$_2$(C$_1$-C$_6$ alkyl), —N(C$_1$-C$_6$ alkyl)S(O)(C$_1$-C$_6$ alkyl), N(C$_1$-C$_6$ alkyl)S(O)$_2$(C$_1$-C$_6$ alkyl), NHS(O)NH$_2$, NHS(O)$_2$NH$_2$, —N(C$_1$-C$_6$ alkyl)S(O)NH$_2$, N(C$_1$-C$_6$ alkyl)S(O)$_2$NH$_2$, NHS(O)NH(C$_1$-C$_6$ alkyl), —NHS(O)$_2$NH(C$_1$-C$_6$ alkyl), NHS(O)N(C$_1$-C$_6$ alkyl)$_2$, NHS(O)$_2$N(C$_1$-C$_6$ alkyl)$_2$, —N(C$_1$-C$_6$ alkyl)S(O)NH(C$_1$-C$_6$ alkyl), N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, C(O)OC$_1$-C$_6$ alkyl, —C(O)NH$_2$, —C(O)NH(C$_1$-C$_6$ alkyl), —C(O)N(C$_1$-C$_6$ alkyl)$_2$, SC$_1$-C$_6$ alkyl, S(O)C$_1$-C$_6$ alkyl, —S(O)$_2$C$_1$-C$_6$ alkyl, S(O)NH(C$_1$-C$_6$ alkyl), —S(O)$_2$NH(C$_1$-C$_6$ alkyl), S(O)N(C$_1$-C$_6$ alkyl)$_2$, —S(O)$_2$N(C$_1$-C$_6$ alkyl)$_2$, P(C$_1$-C$_6$ alkyl)$_2$, —P(O)(C$_1$-C$_6$ alkyl)$_2$, C$_3$-C$_6$ cycloalkyl, or 3- to 7-membered heterocloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OW;

each Z$^1$, Z$^2$, Z$^3$, Z$^4$, Z$^5$, Z$^6$ or Z$^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of Z$^1$, Z$^2$, Z$^3$, Z$^4$, Z$^5$, Z$^6$ or Z$^7$ is N or NH;

or a pharmaceutically acceptable salt thereof.

186. The compound of any one of clauses 168 to 185, wherein the compound that inhibits FAK, SRC and JAK2 is a compound of the formula

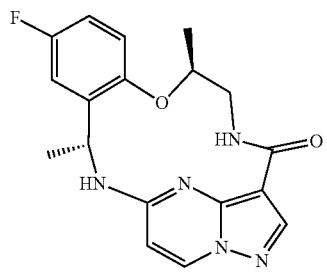

or a pharmaceutically acceptable salt thereof.

187. The compound of any one of clauses 168 to 186, wherein the compound that inhibits FAK, SRC and JAK2 is administered in an amount of about 40 mg, about 80 mg, about 120 mg, or about 160 mg.

188. The compound of any one of clauses 168 to 187, wherein the MEK inhibitor is pimasertib, selumetinib, cobimetinib, PD-0325901, refametinib, TAK733, MEK162, RO5126766, WX-554, RO4987655, GDC-0973, AZD8330, AZD6244, or CI-1040.

189. The compound of any one of clauses 168 to 188, wherein the compound that inhibits FAK, SRC and JAK2 is administered on a schedule of at least one dose of about 40 mg, about 80 mg QD, about 120 mg QD, or about 160 mg QD, followed by at least one dose of about 40 mg BID, about 80 mg BID, about 120 mg BID, or about 160 mg BID.

190. The compound of any one of clauses 168 to 189, wherein the MEK inhibitor is selumetinib.

192. The compound of any one of clauses 168 to 190, wherein the compound that inhibits FAK, SRC and JAK2 is administered at the same time as the MEK inhibitor.

193. The compound of any one of clauses 168 to 190, wherein the compound that inhibits FAK, SRC and JAK2 is administered prior to the MEK inhibitor.

194. The compound of any one of clauses 168 to 190, wherein the compound that inhibits FAK, SRC and JAK2 is administered after the MEK inhibitor.

195. The compound of any one of clauses 168 to 194, wherein the patient has not received a prior treatment.

196. The compound of any one of clauses 168 to 194, wherein the patient has received at least one prior treatment of one or more chemotherapeutic agents or immunotherapies.

197. The compound of any one of clauses 168 to 194, or 196, wherein the patient has received at least one prior treatment of one or more chemotherapeutic agents or immunotherapies, and has developed an acquired resistance to the treatment, and/or developed bypass resistance to the treatment.

198. Use of a compound that inhibits FAK, SRC and JAK2, or a pharmaceutically acceptable salt thereof, in the preparation of a medicament comprising a therapeutically effective amount of the compound that inhibits FAK, SRC, and JAK2, for treating cancer in a patient in combination with a therapeutically effective amount of a MEK inhibitor, provided that the MEK inhibitor is not trametinib.

199. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating cancer in a patient in combination with a therapeutically effective amount of a MEK inhibitor, provided that the MEK inhibitor is not trametinib, wherein at least one genetically altered oncogenic gene has been previously identified in the patient.

200. Use of compound that inhibits FAK, SRC, and JAK2, or a pharmaceutically acceptable salt thereof, in the preparation of a medicament comprising a therapeutically effective amount of the compound that inhibits FAK, SRC, and JAK2, for treating a cancer in a patient in combination with a therapeutically effective amount of a MEK inhibitor, provided that the MEK inhibitor is not trametinib, wherein the cancer is mediated by at least one genetically altered oncogenic gene.

201. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for use in a method of treating a cancer in a patient in combination with a therapeutically effective amount of a MEK inhibitor, provided that the MEK inhibitor is not trametinib, wherein the method comprises;
 i. identifying at least one genetically altered oncogenic gene in the patient, and
 ii. administering to the patient the medicament in combination with a MEK inhibitor, provided that the MEK inhibitor is not trametinib.

202. The use of any one of clauses 169 to 171, wherein the at least one genetically altered oncogenic gene is a genetically altered KRAS, a genetically altered NRAS, a genetically altered HRAS, a genetically altered BRAF, a genetically altered MEK, and/or a genetically altered PI3K.

203. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating non-small cell lung cancer in a patient in combination with a therapeutically effective amount of a MEK inhibitor, provided that the MEK inhibitor is not trametinib.

204. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating non-small cell lung cancer in a patient in combination with a therapeutically effective amount of a MEK inhibitor, provided that the MEK inhibitor is not trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

205. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating non-small cell lung cancer mediated by at least one genetically altered oncogenic gene selected from a genetically altered KRAS, a genetically altered NRAS, genetically altered HRAS, a genetically altered BRAF, a genetically altered MEK, or a genetically altered PI3K in a patient in combination with a therapeutically effective amount of a MEK inhibitor, provided that the MEK inhibitor is not trametinib.

206. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for use in a method of treating non-small cell lung cancer in a patient in combination with a therapeutically effective amount of a MEK inhibitor, provided that the MEK inhibitor is not trametinib, the method comprising;
 i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
 ii. administering to the patient the medicament in combination with a MEK inhibitor, provided that the MEK inhibitor is not trametinib.

207. The use of any one of clauses 204 to 206, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H.

208. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating colorectal cancer or pancreatic cancer in a patient in combination with a therapeutically effective amount of a MEK inhibitor, provided that the MEK inhibitor is not trametinib.

209. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating colorectal cancer or pancreatic cancer in a patient in combination with a therapeutically effective amount of a MEK inhibitor, provided that the MEK inhibitor is not trametinib, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

210. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K in a patient in combination with a therapeutically effective amount of a MEK inhibitor, provided that the MEK inhibitor is not trametinib.

211. Use of a compound that inhibits FAK, SRC, and JAK2, or a pharmaceutically acceptable salt thereof, in the preparation of a medicament comprising a therapeutically effective amount of the compound that inhibits FAK, SRC, and JAK2, for use in a method of treating colorectal cancer or pancreatic cancer in a patient in combination with a therapeutically effective amount of a MEK inhibitor, provided that the MEK inhibitor is not trametinib, the method comprising;
  i. identifying at least one genetically altered oncogenic gene selected from a genetically altered KRAS, a genetically altered NRAS, a genetically altered HRAS, a genetically altered BRAF, a genetically altered MEK, or a genetically altered PI3K in the patient, and
  ii. administering to the patient the medicament in combination with a MEK inhibitor, provided that the MEK inhibitor is not trametinib.

212. The use of any one of clauses 208 to 210, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

213. The use of any one of clauses 198 to 212, wherein the compound that inhibits FAK, SRC, and JAK2 is administered in an amount of from about 40 mg to about 200 mg.

214. The use of any one of clauses 198 to 213, wherein the compound that inhibits FAK, SRC, and JAK2 is administered in an amount of about 40 mg, or about 80 mg, or about 120 mg, or about 160 mg.

215. The use of any one of clauses 198 to 214, wherein the compound that inhibits FAK, SRC and JAK2 is of the formula I

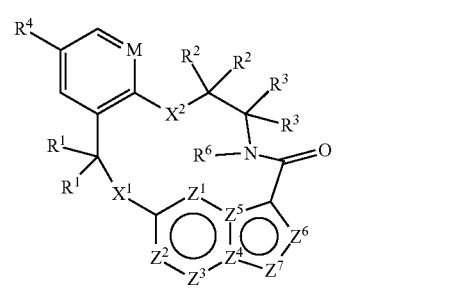

wherein
M is $CR^5$ or N;
$X^1$ and $X^2$ are independently —C($R^7$)($R^8$)—, —S—, —S(O)—, —S(O)$_2$—, —O— or —N($R^9$)—;
each $R^1$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, N($C_1$-$C_6$ alkyl)S(O)$_2$NH$_2$, —NHS(O)NH($C_1$-$C_6$ alkyl), —NHS(O)$_2$NH($C_1$-$C_6$ alkyl), NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), C(O)N($C_1$-$C_6$ alkyl)$_2$, S$C_1$-$C_6$ alkyl, —S(O)$C_1$-$C_6$ alkyl, —S(O)$_2C_1$-$C_6$ alkyl, S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;
each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, N($C_1$-$C_6$ alkyl)S(O)NH$_2$, —N($C_1$-$C_6$ alkyl)S(O)$_2$NH$_2$, —NHS(O)NH($C_1$-$C_6$ alkyl), NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)OC₁-C₆ alkyl, C(O)NH₂, C(O)NH(C₁-C₆ alkyl), —C(O)N(C₁-C₆ alkyl)₂, —SC₁-C₆ alkyl, —S(O)C₁-C₆ alkyl, S(O)₂C₁-C₆ alkyl, —S(O)NH(C₁-C₆ alkyl), —S(O)₂NH(C₁-C₆ alkyl), —S(O)N(C₁-C₆ alkyl)₂, S(O)₂N(C₁-C₆ alkyl)₂, —P(C₁-C₆ alkyl)₂, —P(O)(C₁-C₆ alkyl)₂, C₃-C₆ cycloalkyl, or 3- to 7 membered heterocycloalkyl;

R⁴ and R⁵ are each independently H, fluoro, chloro, bromo, C₁-C₆ alkyl, —OH, —CN, OC₁-C₆ alkyl, —NHC₁-C₆ alkyl, —N(C₁-C₆ alkyl)₂ or —CF₃;

R⁶ is H, C₁-C₆ alkyl or 3- to 7-membered heterocycloalkyl, wherein each hydrogen atom in C₁-C₆ alkyl or 3- to 7-membered heterocycloalkyl is independently optionally substituted by halogen, —OH, —CN, —OC₁-C₆ alkyl, —NH₂, —NH(C₁-C₆ alkyl), —N(C₁-C₆ alkyl)₂, —CO₂H, CO₂C₁C₆ alkyl, —CONH₂, —CONH(C₁-C₆ alkyl), —CON(C₁-C₆ alkyl)₂, C₃-C₆ cycloalkyl, or 3- to 7-membered heterocycloalkyl;

each R⁷ and R⁸ is independently H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl or 5- to 7-membered heteroaryl; wherein each hydrogen atom in C₁-C₆ alkyl, C₂-C₆ alkenyl, C₂C₆ alkynyl, C₃-C₆ cycloalkyl, 3- to 7-membered heterocycloalkyl, C₆-C₁₀ aryl, or 5- to 7-membered heteroaryl is independently optionally substituted by deuterium, halogen, —OH, —CN, —OC₁-C₆ alkyl, —NH₂, —NH(C₁-C₆ alkyl), —N(C₁-C₆ alkyl)₂, NHC(O)C₁-C₆ alkyl, —N(C₁-C₆ alkyl)C(O)C₁-C₆ alkyl, —NHC(O)NH₂, —NHC(O)NHC₁-C₆ alkyl, —N(C₁-C₆ alkyl)C(O)NH₂, —N(C₁-C₆ alkyl)C(O)NHC₁-C₆ alkyl, —NHC(O)N(C₁-C₆ alkyl)₂, N(C₁-C₆ alkyl)C(O)N(C₁-C₆ alkyl)₂, —NHC(O)OC₁-C₆ alkyl, —N(C₁-C₆ alkyl)C(O)OC₁-C₆ alkyl, —NHS(O)(C₁-C₆ alkyl), NHS(O)₂(C₁-C₆ alkyl), —N(C₁-C₆ alkyl)S(O)(C₁-C₆ alkyl), N(C₁-C₆ alkyl)S(O)₂(C₁-C₆ alkyl), NHS(O)NH₂, NHS(O)₂NH₂, —N(C₁-C₆ alkyl)S(O)NH₂, N(C₁-C₆ alkyl)S(O)₂NH₂, NHS(O)NH(C₁-C₆ alkyl), —NHS(O)₂NH(C₁-C₆ alkyl), NHS(O)N(C₁-C₆ alkyl)₂, NHS(O)₂N(C₁-C₆ alkyl)₂, —N(C₁-C₆ alkyl)S(O)NH(C₁-C₆ alkyl), N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, C(O)OC₁-C₆ alkyl, —C(O)NH₂, —C(O)NH(C₁-C₆ alkyl), —C(O)N(C₁-C₆ alkyl)₂, SC₁-C₆ alkyl, S(O)C₁-C₆ alkyl, —S(O)₂C₁-C₆ alkyl, S(O)NH(C₁-C₆ alkyl), —S(O)₂NH(C₁-C₆ alkyl), S(O)N(C₁-C₆ alkyl)₂, —S(O)₂N(C₁-C₆ alkyl)₂, P(C₁-C₆ alkyl)₂, —P(O)(C₁-C₆ alkyl)₂, C₃-C₆ cycloalkyl, or 3- to 7-membered heterocycloalkyl;

each R⁹ is independently H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or mono- or bicyclic heteroaryl; wherein each hydrogen atom in C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or 5- to 7-membered heteroaryl is independently optionally substituted by deuterium, halogen, C₁-C₆ alkyl, C₁-C₆ haloalkyl or —OW;

each Z¹, Z², Z³, Z⁴, Z⁵, Z⁶ or Z⁷ is independently N, NH, or C(R¹⁰), wherein each R¹⁰ is independently H, deuterium, halogen, C₁-C₆ alkyl, —O—C₁-C₆ alkyl, —OH, —NH₂, —NH(C₁-C₆ alkyl), —NH(phenyl), —NH(heteroaryl), —CN, or —CF₃, and provided that at least one of Z¹, Z², Z³, Z⁴, Z⁵, Z⁶ or Z⁷ is N or NH;

or a pharmaceutically acceptable salt thereof.

216. The use of any one of clauses 198 to 215, wherein the compound that inhibits FAK, SRC and JAK2 is a compound of the formula

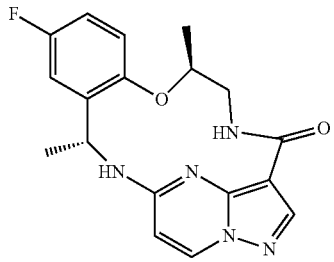 [SMILES: C[C@H]1CNC(=O)c2cnn3ccc(nc23)N[C@H](C)c2cc(F)ccc2O1]

or a pharmaceutically acceptable salt thereof.

217. The use of any one of clauses 198 to 216, wherein the compound that inhibits FAK, SRC and JAK2 is administered in an amount of about 40 mg, about 80 mg, about 120 mg, or about 160 mg.

218. The use of any one of clauses 198 to 217, wherein the MEK inhibitor is pimasertib, selumetinib, cobimetinib, PD-0325901, refametinib, TAK733, MEK162, RO5126766, WX-554, RO4987655, GDC-0973, AZD8330, AZD6244, or CI-1040.

219. The use of any one of clauses 198 to 218, wherein the compound that inhibits FAK, SRC and JAK2 is administered on a schedule of at least one dose of about 40 mg QD. about 80 mg QD, about 120 mg QD, or about 160 mg QD, followed by at least one dose of about 40 mg BID, about 80 mg BID, about 120 mg BID, or about 160 mg BID.

220. The use of any one of clauses 198 to 219, wherein the MEK inhibitor is selumetinib.

221. The use of any one of clauses 198 to 220, wherein the compound that inhibits FAK, SRC and JAK2 is administered at the same time as the MEK inhibitor.

222. The use of any one of clauses 198 to 220, wherein the compound that inhibits FAK, SRC and JAK2 is administered prior to the MEK inhibitor.

223. The use of any one of clauses 198 to 220, wherein the compound that inhibits FAK, SRC and JAK2 is administered after the MEK inhibitor.

224. The use of any one of clauses 198 to 223, wherein the patient has not received a prior treatment.

225. The use of any one of clauses 198 to 223, wherein the patient has received at least one prior treatment of one or more chemotherapeutic agents or immunotherapies.

226. The use of any one of clauses 198 to 223 or 225, wherein the patient has received at least one prior treatment of one or more chemotherapeutic agents or immunotherapies, and has developed an acquired resistance to the treatment, and/or developed bypass resistance to the treatment.

227. A medicament comprising a therapeutically effective amount of a compound that inhibits FAK, SRC and JAK2, or a pharmaceutically acceptable salt thereof, combined with a therapeutically effective amount of a MEK inhibitor, provided that the MEK inhibitor is not trametinib, in fixed or free combination.

228. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect on a cancer in a patient, wherein at least one genetically altered oncogenic gene has been previously identified in the patient.

229. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect on a cancer mediated by at least one genetically altered oncogenic gene.

230. The medicament of clause 228 or 229, wherein the at least one genetically altered oncogenic gene is a genetically altered KRAS, a genetically altered NRAS, a genetically altered BRAF, a genetically altered MEK, and/or a genetically altered PI3K.

231. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect for treating non-small cell lung cancer.

232. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect for treating non-small cell lung cancer in a patient, wherein at least one genetically altered oncogenic gene selected from a genetically altered KRAS, a genetically altered NRAS, a genetically altered BRAF, a genetically altered MEK, or a genetically altered PI3K has been previously identified in the patient.

233. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect for treating non-small cell lung cancer mediated by at least one genetically altered oncogenic gene selected from a genetically altered KRAS, a genetically altered NRAS, a genetically altered BRAF, a genetically altered MEK, or a genetically altered PI3K in a patient.

234. The medicament of clause 232 or 233, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R, or selected from the group consisting of G12D, G13D, and Q61H.

235. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect for treating colorectal cancer or pancreatic cancer in a patient.

236. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect for treating colorectal cancer or pancreatic cancer in a patient, wherein at least one genetically altered oncogenic gene selected from a genetically altered KRAS, a genetically altered NRAS, a genetically altered HRAS, a genetically altered BRAF, a genetically altered MEK, or a genetically altered PI3K has been previously identified in the patient.

237. A medicament comprising a therapeutically effective amount of a compound that inhibits FAK, SRC, and JAK2, or a pharmaceutically acceptable salt thereof, combined with a therapeutically effective amount of a MEK inhibitor, provided that the MEK inhibitor is not trametinib, in fixed or free combination, wherein the medicament provides an effect for treating colorectal cancer or pancreatic cancer mediated by at least one genetically altered oncogenic gene selected from a genetically altered KRAS, a genetically altered NRAS, a genetically altered HRAS, a genetically altered BRAF, a genetically altered MEK, or a genetically altered PI3K in a patient.

238. The medicament of clause 236 or 237, wherein the genetically altered KRAS comprises at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

239. The medicament of any one of clauses 227 to 238, wherein the compound that inhibits FAK, SRC, and JAK2 is provided in the medicament in an amount of from about 40 mg to about 200 mg.

240. The medicament of any one of clauses 227 to 239, wherein the compound that inhibits FAK, SRC, and JAK2 is provided in the medicament in an amount of about 40 mg, or about 80 mg, or about 120 mg, or about 160 mg.

241. The medicament of any one of clauses 227 to 240, wherein the compound that inhibits FAK, SRC and JAK2 is of the formula I

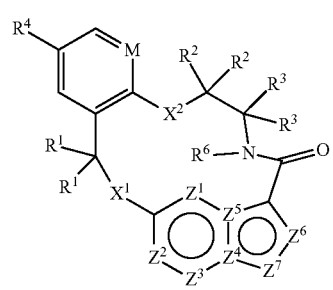

wherein

M is $CR^5$ or N;

$X^1$ and $X^2$ are independently —$C(R^7)(R^8)$—, —S—, —S(O)—, —S(O)$_2$—, —O— or —N($R^9$)—;

each $R^1$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS (O)($C_1$-$C_6$ alkyl), —NHS(O)$_2$($C_1$-$C_6$ alkyl), —N($C_1$-$C_6$ alkyl)S(O)($C_1$-$C_6$ alkyl), N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, N($C_1$-$C_6$ alkyl)S(O)$_2$NH$_2$, —NHS(O)NH($C_1$-$C_6$ alkyl), —NHS(O)$_2$NH($C_1$-$C_6$ alkyl), NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), C(O)N($C_1$-$C_6$ alkyl)$_2$, S$C_1$-$C_6$ alkyl, —S(O)$C_1$-$C_6$ alkyl, —S(O)$_2$$C_1$-$C_6$ alkyl, S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NHC$_1$-$C_6$ alkyl, —N($C_1$-$C_6$ alkyl)C(O)NH$_2$, —N($C_1$-$C_6$ alkyl)C(O)NHC$_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, N($C_1$-$C_6$ alkyl)S(O)NH$_2$, —N($C_1$-$C_6$ alkyl)S(O)$_2$NH$_2$, —NHS(O)NH($C_1$-$C_6$ alkyl), NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, C(O)NH$_2$, C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7 membered heterocycloalkyl;

$R^4$ and $R^5$ are each independently H, fluoro, chloro, bromo, $C_1$-$C_6$ alkyl, —OH, —CN, O$C_1$-$C_6$ alkyl, —NHC$_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, CO$_2$$C_1$$C_6$ alkyl, —CONH$_2$, —CONH($C_1$-$C_6$ alkyl), —CON($C_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NHC$_1$-$C_6$ alkyl, —N($C_1$-$C_6$ alkyl)C(O)NH$_2$, —N($C_1$-$C_6$ alkyl)C(O)NHC$_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS (O)($C_1$-$C_6$ alkyl), NHS(O)$_2$($C_1$-$C_6$ alkyl), —N($C_1$-$C_6$ alkyl) S(O)($C_1$-$C_6$ alkyl), N($C_1$-$C_6$ alkyl)S(O)$_2$($C_1$-$C_6$ alkyl), NHS (O)NH$_2$, NHS(O)$_2$NH$_2$, —N($C_1$-$C_6$ alkyl)S(O)NH$_2$, N($C_1$-$C_6$ alkyl)S(O)$_2$NH$_2$, NHS(O)NH($C_1$-$C_6$ alkyl), —NHS(O)$_2$NH($C_1$-$C_6$ alkyl), NHS(O)N($C_1$-$C_6$ alkyl)$_2$, NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, C(O)O$C_1$-$C_6$ alkyl, —C(O)NH$_2$, —C(O) NH($C_1$-$C_6$ alkyl), —C(O)N($C_1$-$C_6$ alkyl)$_2$, S$C_1$-$C_6$ alkyl, S(O)$C_1$-$C_6$ alkyl, —S(O)$_2$$C_1$-$C_6$ alkyl, S(O)NH($C_1$-$C_6$ alkyl), —S(O)$_2$NH($C_1$-$C_6$ alkyl), S(O)N($C_1$-$C_6$ alkyl)$_2$, —S(O)$_2$N($C_1$-$C_6$ alkyl)$_2$, P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OW;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —NH$_2$, —NH($C_1$-$C_6$ alkyl), —NH(phenyl), —NH(heteroaryl), —CN, or —CF$_3$, and provided that at least one of $Z^1$, $Z^2$, $Z^3$, $Z^4$, $Z^5$, $Z^6$ or $Z^7$ is N or NH;

or a pharmaceutically acceptable salt thereof.

242. The medicament of any one of clauses 227 to 241, wherein the compound that inhibits FAK, SRC and JAK2 is a compound of the formula

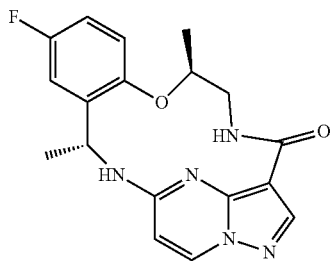 [SMILES: C[C@H]1CNC(=O)c2cnn3ccc(nc23)N[C@H](C)c2cc(F)ccc2O1]

or a pharmaceutically acceptable salt thereof.

243. The medicament of any one of clauses 227 to 242, wherein the compound that inhibits FAK, SRC and JAK2 is provided in the medicament in an amount of about 40 mg, about 80 mg, about 120 mg, or about 160 mg.

244. The medicament of any one of clauses 227 to 243, wherein the MEK inhibitor is pimasertib, selumetinib, cobimetinib, PD-0325901, refametinib, TAK733, MEK162, RO5126766, WX-554, RO4987655, GDC-0973, AZD8330, AZD6244, or CI-1040.

245. The medicament of any one of clauses 227 to 244, wherein the compound that inhibits FAK, SRC and JAK2 is provided in the medicament on a schedule of at least one dose of about 40 mg QD, about 80 mg QD, about 120 mg QD, or about 160 mg QD, followed by at least one dose of about 40 mg BID, about 80 mg BID, about 120 mg BID, or about 160 mg BID.

246. The medicament of any one of clauses 227 to 245, wherein the MEK inhibitor is selumetinib.

247. The medicament of any one of clauses 227 to 246, wherein the compound that inhibits FAK, SRC and JAK2 is provided at the same time as the MEK inhibitor.

248. The medicament of any one of clauses 227 to 246, in free combination, wherein the compound that inhibits FAK, SRC and JAK2 is provided prior to the MEK inhibitor.

249. The medicament of any one of clauses 227 to 246, in free combination, wherein the compound that inhibits FAK, SRC and JAK2 is provided after the MEK inhibitor.

250. The medicament of any one of clauses 227 to 249, wherein the patient has not received a prior treatment.

251. The medicament of any one of clauses 227 to 249, wherein the patient has received at least one prior treatment of one or more chemotherapeutic agents or immunotherapies.

252. The medicament of any one of clauses 227 to 249, or 251, wherein the patient has received at least one prior treatment of one or more chemotherapeutic agents or immunotherapies, and has developed an acquired resistance to the treatment, and/or developed bypass resistance to the treatment.

253. A composition of a compound that inhibits FAK, SRC and JAK2 and trametinib, where the two components come into contact with each other at a locus.

254. The composition of clause 253, wherein the compound that inhibits FAK, SRC and JAK2 is of the formula I

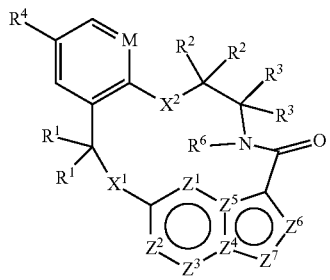

I wherein
M is $CR^5$ or N;
$X^1$ and $X^2$ are independently —$C(R^7)(R^8)$—, —S—, —S(O)—, —S(O)$_2$—, —O— or —N($R^9$)—;
each $R^1$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, N($C_1$-$C_6$ alkyl)S(O)$_2$NH$_2$, —NHS(O)NH($C_1$-$C_6$ alkyl), —NHS(O)$_2$NH($C_1$-$C_6$ alkyl), NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), C(O)N($C_1$-$C_6$ alkyl)$_2$, S$C_1$-$C_6$ alkyl, —S(O)$C_1$-$C_6$ alkyl, —S(O)$_2C_1$-$C_6$ alkyl, S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, N($C_1$-$C_6$ alkyl)S(O)NH$_2$, —N($C_1$-$C_6$ alkyl)S(O)$_2$NH$_2$, —NHS(O)NH($C_1$-$C_6$ alkyl), NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, C(O)NH$_2$, C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7 membered heterocycloalkyl;

$R^4$ and $R^5$ are each independently H, fluoro, chloro, bromo, $C_1$-$C_6$ alkyl, —OH, —CN, O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, CO$_2C_1C_6$ alkyl, —CONH$_2$, —CONH($C_1$-$C_6$ alkyl), —CON($C_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), NHS(O)$_2$($C_1$-$C_6$ alkyl), —N($C_1$-$C_6$ alkyl) S(O)($C_1$-$C_6$ alkyl), N($C_1$-$C_6$ alkyl)S(O)$_2$($C_1$-$C_6$ alkyl), NHS(O)NH$_2$, NHS(O)$_2$NH$_2$, —N($C_1$-$C_6$ alkyl)S(O)NH$_2$, N($C_1$-$C_6$ alkyl)S(O)$_2$NH$_2$, NHS(O)NH($C_1$-$C_6$ alkyl), —NHS(O)$_2$NH($C_1$-$C_6$ alkyl), NHS(O)N($C_1$-$C_6$ alkyl)$_2$, NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, C(O)O$C_1$-$C_6$ alkyl, —C(O)NH$_2$, —C(O)

NH($C_1$-$C_6$ alkyl), —C(O)N($C_1$-$C_6$ alkyl)$_2$, S$C_1$-$C_6$ alkyl, S(O)$C_1$-$C_6$ alkyl, —S(O)$_2$$C_1$-$C_6$ alkyl, S(O)NH($C_1$-$C_6$ alkyl), —S(O)$_2$NH($C_1$-$C_6$ alkyl), S(O)N($C_1$-$C_6$ alkyl)$_2$, —S(O)$_2$N($C_1$-$C_6$ alkyl)$_2$, P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OW;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —NH$_2$, —NH($C_1$-$C_6$ alkyl), —NH(phenyl), —NH(heteroaryl), —CN, or CF$_3$, and provided that at least one of $Z^1$, $Z^2$, $Z^3$, $Z^4$, $Z^5$, $Z^6$ or $Z^7$ is N or NH;

or a pharmaceutically acceptable salt thereof.

255. The composition of clause 253 or 254, wherein the compound that inhibits FAK, SRC and JAK2 is a compound of the formula

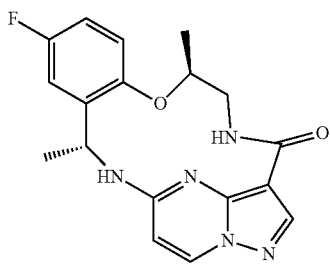 [SMILES: C[C@H]1CNC(=O)c2cnn3ccc(nc23)N[C@H](C)c2cc(F)ccc2O1]

or a pharmaceutically acceptable salt thereof.

256. The composition of any one of clauses 253 to 255, wherein the locus is a cancer or a cancer cell.

257. The composition of any one of clauses 253 to 256, wherein the locus is a cancer selected from non-small cell lung cancer, colorectal cancer or pancreatic cancer and pancreatic cancer.

258. The composition of clause 257, wherein the cancer is non-small cell lung cancer.

259. The composition of clause 257, wherein the cancer is colorectal cancer or pancreatic cancer.

260. The composition of any one of clauses 253 to 259, wherein the locus comprises at least one genetically altered oncogenic gene selected from a genetically altered KRAS, a genetically altered NRAS, a genetically altered HRAS, a genetically altered BRAF, a genetically altered MEK, or a genetically altered PI3K.

261. The composition of any one of clauses 253 to 260, wherein the locus comprises a genetically altered KRAS having at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12A, G12C, G12D, G12S, G12V, G13D, Q61H, and Q61K, or selected from the group consisting of G12D, G13D, and Q61H; or selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

262. The composition of any one of clauses 253 to 261, wherein the compound that inhibits FAK, SRC, and JAK2 is provided in the composition in an amount of from about 40 mg to about 200 mg.

263. The composition of any one of clauses 253 to 262, wherein the MEK inhibitor is pimasertib, selumetinib, cobimetinib, PD-0325901, refametinib, TAK733, MEK162, RO5126766, WX-554, RO4987655, GDC-0973, AZD8330, AZD6244, or CI-1040.

264. The composition of any one of clauses 253 to 263, wherein the compound that inhibits FAK, SRC and JAK2 is provided in the composition in an amount of about 40 mg, about 80 mg, about 120 mg, or about 160 mg.

265. The composition of any one of clauses 253 to 264, wherein the MEK inhibitor is selumetinib.

266. A composition of a compound that inhibits FAK, SRC and JAK2 and trametinib, where the two components come into contact with each other only in the human body.

267. The composition of clause 266, wherein the compound that inhibits FAK, SRC and JAK2 is of the formula I

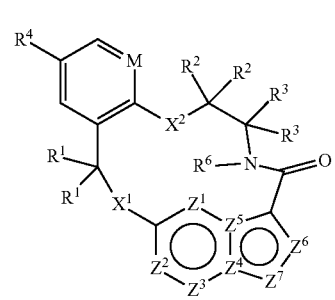

wherein
M is CR$^5$ or N;
$X^1$ and $X^2$ are independently —C($R^7$)($R^8$)—, —S—, —S(O)—, —S(O)$_2$—, —O— or —N($R^9$)—;
each $R^1$ is independently $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7$$R^8$; wherein each hydrogen atom in $C_1$-$C_6$ alkyl, $C_2$-$C_6$ alkenyl, $C_2$$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, N($C_1$-$C_6$ alkyl)S(O)$_2$NH$_2$, —NHS(O)NH($C_1$-$C_6$ alkyl), —NHS(O)$_2$NH($C_1$-$C_6$ alkyl), NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), C(O)N($C_1$-$C_6$ alkyl)$_2$, S$C_1$-$C_6$ alkyl, —S(O)$C_1$-$C_6$ alkyl, —S(O)$_2$$C_1$-$C_6$ alkyl, S(O)NH($C_1$-$C_6$ alkyl), —S(O)$_2$NH($C_1$-$C_6$ alkyl), —S(O)N($C_1$-$C_6$ alkyl)$_2$, —S(O)$_2$N(C$_1$-C$_6$ alkyl)$_2$, P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^7$ or —C(O)NR$^7$R$^8$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, NHS(O)$_2$NH$_2$, N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, C(O)NH$_2$, C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7 membered heterocycloalkyl;

R$^4$ and R$^5$ are each independently H, fluoro, chloro, bromo, C$_1$-C$_6$ alkyl, —OH, —CN, OC$_1$-C$_6$ alkyl, —NHC$_1$-C$_6$ alkyl, —N(C$_1$-C$_6$ alkyl)$_2$ or —CF$_3$;

R$^6$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, CO$_2$C$_1$C$_6$ alkyl, —CONH$_2$, —CONH(C$_1$-C$_6$ alkyl), —CON(C$_1$-C$_6$ alkyl)$_2$, C$_3$-C$_6$ cycloalkyl, or 3- to 7-membered heterocycloalkyl;

each R$^7$ and R$^8$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or 5- to 7-membered heteroaryl; wherein each hydrogen atom in C$_1$-C$_6$ alkyl, C$_2$-C$_6$ alkenyl, C$_2$C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), NHS(O)$_2$(C$_1$-C$_6$ alkyl), —N(C$_1$-C$_6$ alkyl)S(O)(C$_1$-C$_6$ alkyl), N(C$_1$-C$_6$ alkyl)S(O)$_2$(C$_1$-C$_6$ alkyl), NHS(O)NH$_2$, NHS(O)$_2$NH$_2$, —N(C$_1$-C$_6$ alkyl)S(O)NH$_2$, N(C$_1$-C$_6$ alkyl)S(O)$_2$NH$_2$, NHS(O)NH(C$_1$-C$_6$ alkyl), —NHS(O)$_2$NH(C$_1$-C$_6$ alkyl), NHS(O)N(C$_1$-C$_6$ alkyl)$_2$, NHS(O)$_2$N(C$_1$-C$_6$ alkyl)$_2$, —N(C$_1$-C$_6$ alkyl)S(O)NH(C$_1$-C$_6$ alkyl), N(C$_1$-C$_6$ alkyl)S(O)$_2$NH(C$_1$-C$_6$ alkyl)$, —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, C(O)OC$_1$-C$_6$ alkyl, —C(O)NH$_2$, —C(O)NH(C$_1$-C$_6$ alkyl), —C(O)N(C$_1$-C$_6$ alkyl)$_2$, SC$_1$-C$_6$ alkyl, S(O)C$_1$-C$_6$ alkyl, —S(O)$_2$C$_1$-C$_6$ alkyl, S(O)NH(C$_1$-C$_6$ alkyl), —S(O)$_2$NH(C$_1$-C$_6$ alkyl), S(O)N(C$_1$-C$_6$ alkyl)$_2$, —S(O)$_2$N(C$_1$-C$_6$ alkyl)$_2$, P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or 5- to 7-membered heteroaryl is independently optionally substituted by deuterium, halogen, C$_1$-C$_6$ alkyl, C$_1$-C$_6$ haloalkyl or —OW;

each $Z^1$, $Z^2$, $Z^3$, $Z^4$, $Z^5$, $Z^6$ or $Z^7$ is independently N, NH, or C(R$^{10}$), wherein each R$^{10}$ is independently H, deuterium, halogen, C$_1$-C$_6$ alkyl, —O—C$_1$-C$_6$ alkyl, —OH, —NH$_2$, —NH(C$_1$-C$_6$ alkyl), —NH(phenyl), —NH(heteroaryl), —CN, or —CF$_3$, and provided that at least one of $Z^1$, $Z^2$, $Z^3$, $Z^4$, $Z^5$, $Z^6$ or $Z^7$ is N or NH;

or a pharmaceutically acceptable salt thereof.

268. The composition of clause 266 or 267, wherein the compound that inhibits FAK, SRC and JAK2 is a compound of the formula

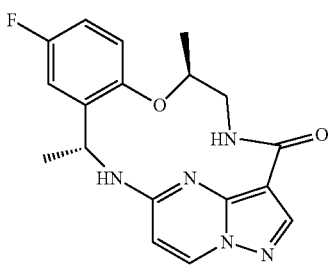 [SMILES: C[C@H]1CNC(=O)c2cnn3ccc(nc23)N[C@H](C)c2cc(F)ccc2O1]

or a pharmaceutically acceptable salt thereof.

269. The composition of any one of clauses 266 to 268, wherein the human body comprises at least one genetically altered oncogenic gene selected from a genetically altered KRAS, a genetically altered NRAS, a genetically altered BRAF, a genetically altered MEK, or a genetically altered PI3K.

270. The composition of any one of clauses 266 to 269, wherein the human body comprises a genetically altered KRAS having at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12A, G12C, G12D, G12S, G12V, G13D, Q61H, and Q61K, or selected from the group consisting of G12D, G13D, and Q61H; or selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I; or selected from the group consisting of G12D, G12V, G12R, Q61H, G12C, and G12S.

271. The composition of any one of clauses 266 to 270, wherein the compound that inhibits FAK, SRC, and JAK2 is provided in the composition in an amount of from about 40 mg to about 200 mg.

272. The composition of any one of clauses 266 to 271, wherein the MEK inhibitor is pimasertib, selumetinib, cobimetinib, PD-0325901, refametinib, TAK733, MEK162, RO5126766, WX-554, RO4987655, GDC-0973, AZD8330, AZD6244, or CI-1040.

273. The composition of any one of clauses 266 to 272, wherein the compound that inhibits FAK, SRC and JAK2 is provided in the composition in an amount of about 40 mg, about 80 mg, about 120 mg, or about 160 mg.

274. The composition of any one of clauses 266 to 273, wherein the MEK inhibitor is selumetinib.

275. The composition of any one of clauses 266 to 274, wherein the human body has not received a prior treatment.

276. The composition of any one of clauses 266 to 274, wherein the human body has received at least one prior treatment of one or more chemotherapeutic agents or immunotherapies.

277. The composition of any one of clauses 266 to 274, or 276, wherein the host animal is a human patient in need of such treatment who has received at least one prior treatment of one or more chemotherapeutic agents or immunotherapies, and developed an acquired resistance to the treatment or developed bypass resistance to the treatment.

278. The method, use, compound, composition, or medicament of any one of the preceding claims, wherein the MEK inhibitor is trametinib, selumetinib, LY3214996, RO5126766, TNO155 (SHP099), or mirdametinib, or a pharmaceutically acceptable salt thereof.

BRIEF DESCRIPTION OF THE DRAWINGS

FIG. 2b is a chart showing the body weight of mice bearing Calu-6 cell-derived xenograft tumors harboring the $KRAS^{Q61K}$ mutation when treated with: (●) Control; (▼) Compound 1 (15 mg/kg BID); (Δ) Trametinib (0.2 mg/kg QD); (▲) Compound 1 (15 mg/kg BID) plus Trametinib (0.2 mg/kg QD); (□) Trametinib (0.6 mg/kg QD); (■) Compound 1 (15 mg/kg BID) plus Trametinib (0.6 mg/kg QD). The body weight data was obtained from the same cohort of mice as in FIG. 2a.

FIG. 4b shows body weights of mice bearing HCT-116 cell-derived xenograft tumors harboring the $KRAS^{G13D}$ mutation when treated with: (●) Control; (▼) Compound 1 (15 mg/kg BID); (▲) Trametinib (0.4 mg/kg QD); (■) Compound 1 (15 mg/kg BID) plus Trametinib (0.4 mg/kg QD). The body weight data was obtained from the same cohort of mice as in FIG. 4a.

FIG. 5b is a chart showing the body weight of mice bearing mLU6045 MuPrime mouse tumors with the $KRAS^{G12D/+}$; $p53^{-/-}$ mutations when treated with: (●) Control; (▼) Compound 1 (15 mg/kg BID); ( ) Trametinib (1 mg/kg QD); (■) Compound 1 (15 mg/kg BID) plus Trametinib (1 mg/kg QD). The body weight data was obtained from the same cohort of mice as in FIG. 5a.

DETAILED DESCRIPTION

Figure 1A:
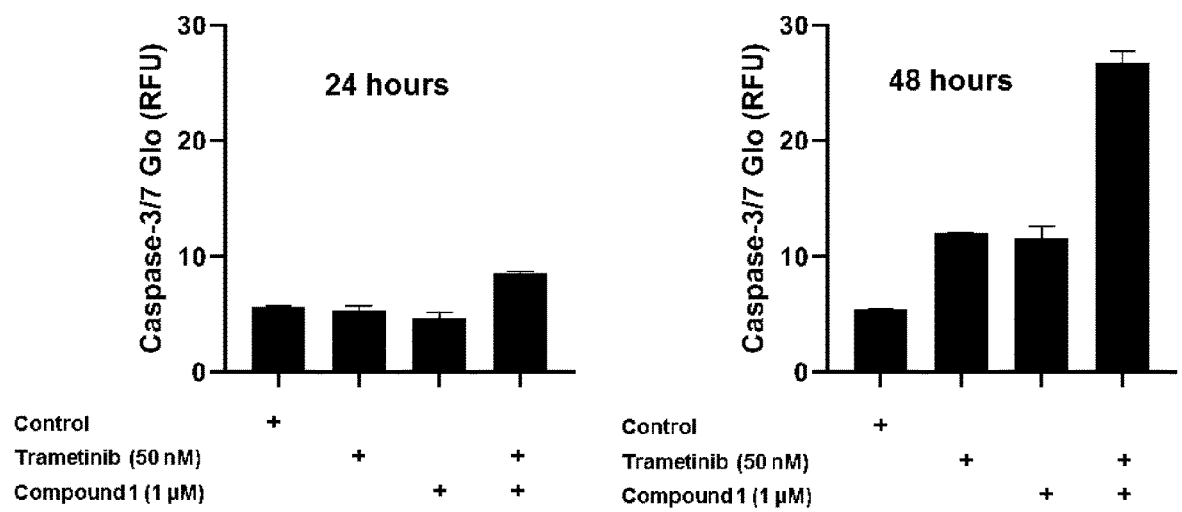
FIG. 1a shows the level of caspase-3/7 activated by Compound 1 (1 μM), trametinib (50 nM) and Compound 1 (1 μM)+trametinib (50 nM) at 24 hr and 48 hr timepoints in NCI-H358 cells with KRAS G12C mutation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, N.Y.: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

The methods described herein are used to treat a "host animal" with cancer in need of such treatment. In one embodiment, the methods described herein can be used for both human clinical medicine and veterinary applications. Thus, a "host animal" can be administered the combinations described herein, and the host animal can be human (e.g., a human patient, a.k.a. a patient) or, in the case of veterinary applications, can be a laboratory, agricultural, or domestic animal. In one aspect, the host animal can be a human, or a laboratory animal such as a rodent (e.g., mice, rats, etc.), and the like.

As used herein, the term "cancer" includes, but is not limited to, ALCL, lung cancer, such as non-small cell lung cancer (NSCLC), including adenocarcinoma, lung squamous cell carcinoma, large cell carcinoma, and large cell neuroendocrine tumors, small cell lung cancer (SCLC), neuroblastoma, inflammatory myofibroblastic tumor, adult renal cell carcinoma, pediatric renal cell carcinoma, breast cancer, such as triple negative breast cancer, triple positive breast cancer, colonic adenocarcinoma, glioblastoma, glioblastoma multiforme, thyroid cancer, such as anaplastic thyroid cancer, cholangiocarcinoma, ovarian cancer, gastric cancer, such as gastric adenocarcinoma, colorectal cancer (CRC), inflammatory myofibroblastic tumor, angiosarcoma, epithelioid hemangioendothelioma, intrahepatic cholangiocarcinoma, thyroid papillary cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, skin cancer, such as skin cutaneous melanoma, head and neck squamous cell carcinoma (HN-SCC), pediatric glioma CML, prostate cancer, ovarian serous cystadenocarcinoma, skin cutaneous melanoma, castrate-resistant prostate cancer, Hodgkin lymphoma, and serous and clear cell endometrial cancer. It will be appreciated that the term "cancer" includes both primary cancers or primary tumors and metastatic cancers or metastatic tumors. For example, metastatic NSCLC, metastatic CRC, metastatic pancreatic cancer, metastatic colorectal carcinoma, metastatic HNSCC, and the like. It will be appreciated that the term "cancer" includes cancers that involve the upregulation of certain genes or genetic mutations in certain genes that can lead to disease progression, such up-regulation of epidermal growth factor receptor.

In particular, in some embodiments of the various aspects described herein, the cancer is mediated by at least one genetically altered oncogenic gene selected from a genetically altered KRAS, a genetically altered NRAS, a genetically altered HRAS, a genetically altered BRAF, a genetically altered MEK, or a genetically altered PI3K, or such genetically altered oncogenic gene has been identified in the patient. In some embodiments of the various aspects described herein, the cancer is non-small cell lung cancer mediated by a genetically altered KRAS comprising at least one mutation selected from the group consisting of G12C, G12V, G12D, G12A, G13C, G12S, D12R, D12F, G13D, G13V, G13R, G13E, Q61H, Q61E, Q61L, and Q61R. In some embodiments of the various aspects described herein, the cancer is non-small cell lung cancer mediated by a genetically altered KRAS comprising at least one mutation selected from the group consisting of G12D, G13D, and Q61H; In some embodiments of the various aspects described herein, the cancer is non-small cell lung cancer mediated by a genetically altered KRAS comprising at least one mutation that is not G12A, G12C, G12S, G12V, or Q61K.

In some embodiments of the various aspects described herein, the cancer is colorectal cancer mediated by a genetically altered KRAS comprising at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I.

In some embodiments of the various aspects described herein, the cancer is pancreatic cancer mediated by a genetically altered KRAS comprising at least one mutation selected from the group consisting of G12D, G12V, G12R, Q61H, G12C, and G12S.

As used herein, the term "KRAS" refers to the KRAS gene, the corresponding mRNA resulting from transcription of the KRAS gene, or the protein encoded by the KRAS gene, called K-Ras, that is involved in the RAS/MAPK signaling pathway. The terms KRAS gene, K-Ras, and RAS/MAPK signaling pathway will be known and understood by one of skill in the art. It will be appreciated that KRAS mutations occur in approximately one in seven of all human metastatic cancers, and that those mutations can occur in a variety of locations in the KRAS gene coding sequence. KRAS mutations primarily occur in KRAS codons 12 and 13, and also occur in codons 18, 61, 117, and 146 at low frequencies and have distinct effects on tumor cell signaling based on the codon and missense mutation. Examples of KRAS mutations include, but are not limited to KRAS G12D, KRAS G12V, KRAS G12R, KRAS G12S, KRAS G13C, KRAS G13D, KRAS A18D, KRAS Q61H, KRAS K117N, and the like.

Chemical Definitions

As used herein "Mek inhibitor" or "MEK inhibitor" includes, but is not limited to, any compound or agent known in the art to inhibit the MAPK/ERK kinase-1 and -2 gene or inhibit the protein encoded by the MAPK/ERK kinase-1 and -2 gene (MEK1 and MEK2; MAP2K1 and MAP2K2). Exemplary Mek inhibitors for use in connection with the methods and compositions described herein include, but are not limited to, trametinib, pimasertib (AST03026); selumetinib (AZD6244); cobimetinib; mirdametinib (PD-0325901); refametinib (RDEA119); TAK733; MEK162; RO5126766; WX-554; RO4987655; GDC-0973; AZD8330; AZD6244; and CI-1040 (PD-184352); GDC-0623; HL-085.

As used herein, the term "trametinib" refers to a compound having the formula

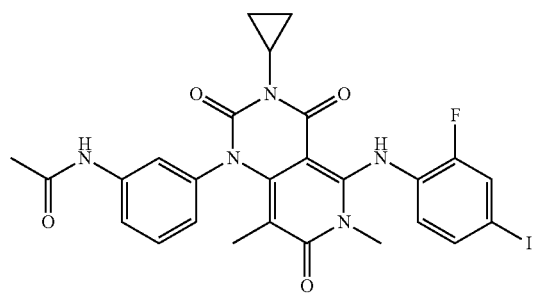 [SMILES: CC(=O)Nc1cccc(-n2c(=O)n(C3CC3)c(=O)c3c(Nc4ccc(I)cc4F)n(C)c(=O)c(C)c32)c1]

or a pharmaceutically acceptable salt thereof, which is also known as GSK1120212 or N-(3-{3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl}phenyl)acetamide. Trametinib is an orally bioavailable inhibitor of mitogen-activated protein kinase kinase (MEK MAPK/ERK kinase) with potential antineoplastic activity. Trametinib specifically binds to and inhibits MEK 1 and 2, resulting in an inhibition of growth factor-mediated cell signaling and cellular proliferation in various cancers.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_9$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (═O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C═C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. CC). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

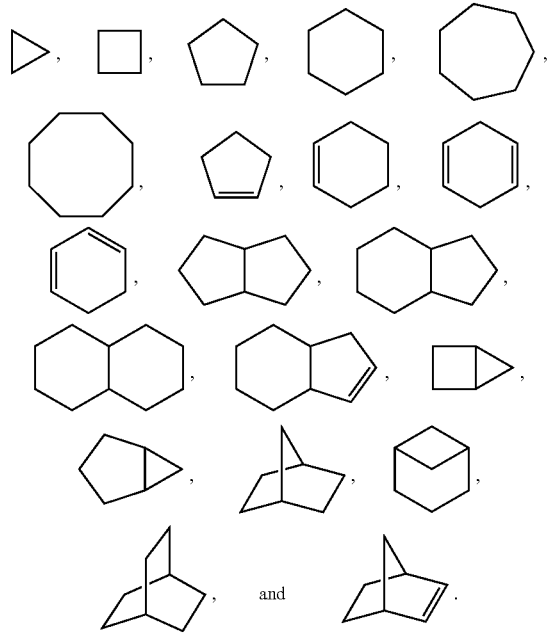

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1,2,3,4-tetrahydropyridinyl, and the like. Illustrative examples of heterocycloalkyl groups shown in graphical representations include the following entities, in the form of properly bonded moieties:

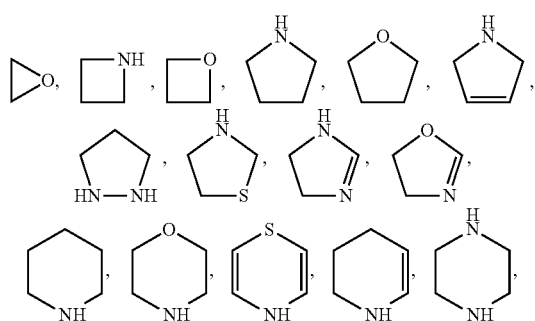

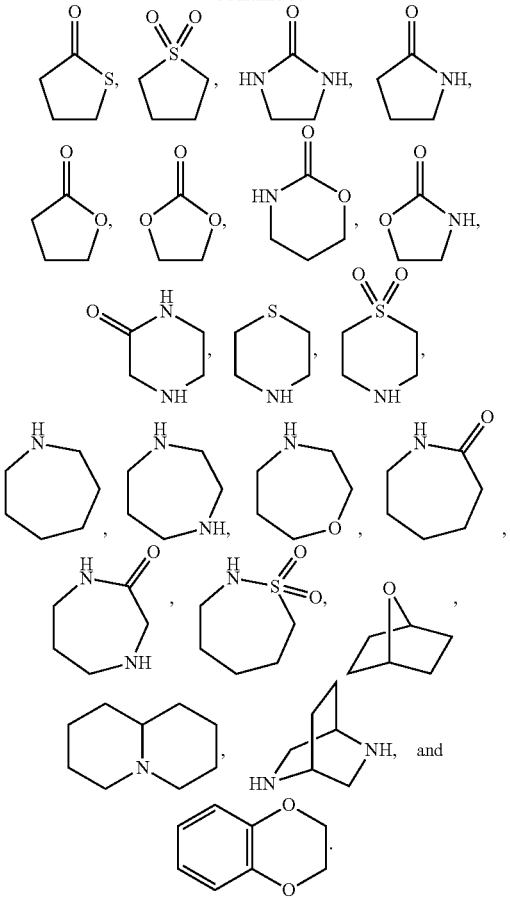

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

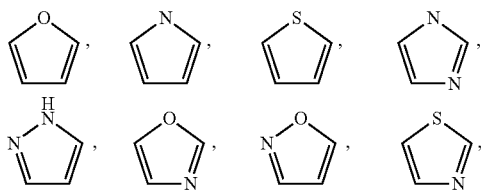

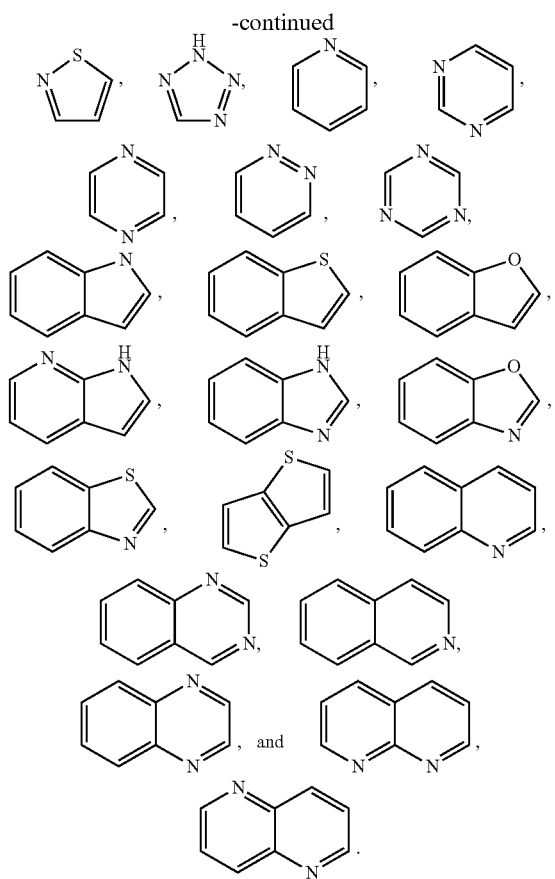

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cycl op entyl oxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol " ∿∿∿ " include both stereoisomers for the carbon atom which the symbol " ∿∿∿ " is attached, specifically both the bonds " ▬▬◣ " are " ॥॥॥॥॥ " encompassed by the meaning of " ∿∿∿ ".

For example, in some exemplary embodiments, certain compounds provided herein can be described by the formula

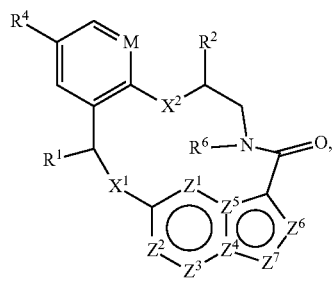

which formula will be understood to encompass compounds having all stereochemical configurations at the relevant carbon atoms, including

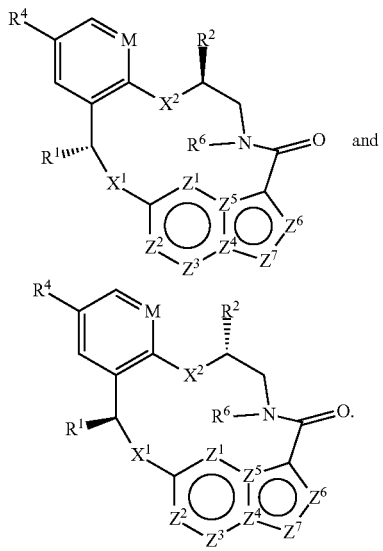

Embodiments

In some embodiments, the methods described herein relate to the treatment of cancer comprising administering to a patient in need of treatment a therapeutically effective amount of one or more compounds that inhibit FAK, SRC and/or JAK2 in combination with trametinib. In some embodiments, the methods described herein relate to the treatment of cancer comprising administering to a patient in need of treatment a therapeutically effective amount of a compound that inhibits FAK, SRC and JAK2 in combination with trametinib. It will be appreciated that an inhibitor is any substance that reduces or suppresses the activity of another substance, such as a cell surface receptor (i.e. a receptor tyrosine kinase), or a kinase (i.e. a non-receptor tyrosine kinase), or the transcription and/or translation of a gene. It will be appreciated that "a compound that inhibits FAK, SRC and JAK2" is a compound that has affinity for all three of the biological targets FAK, SRC and JAK2.

It has been discovered that certain compounds described herein have been surprisingly shown to be inhibitors of FAK, SRC and JAK2, and can be used in combination with trametinib to treat cancer in a patient in need of such treatment. In some embodiments, the combination of one or more compounds that inhibit FAK, SRC and/or JAK2 with trametinib can provide a synergistic response in a patient in need of treatment for cancer. In some embodiments, the combination of a compound that inhibits FAK, SRC and JAK2 with trametinib can provide a synergistic response in a patient in need of treatment for cancer. In some embodiments, methods for treating cancer comprising administering a combination of a therapeutically effective amount of a compound that inhibits FAK, SRC and JAK2 and a therapeutically effective amount of trametinib. In some embodiments, the compound that inhibits FAK, SRC and JAK2 and trametinib are co-formulated. In some embodiments, the compound that inhibits FAK, SRC and JAK2 and trametinib are administered at the same time. In some embodiments, the compound that inhibits FAK, SRC and JAK2 and trametinib are individually formulated, and administered at the same time. In some embodiments, the compound that inhibits FAK, SRC and JAK2 and trametinib are individually formulated, and administered in sequence. In some embodiments, the sequential administration of the compound that inhibits FAK, SRC and JAK2 and trametinib can be accomplished with the compound that inhibits FAK, SRC and JAK2 administered first, and trametinib administered second. In some embodiments, the sequential administration of the compound that inhibits FAK, SRC and JAK2 and trametinib can be accomplished with agent that inhibits KRAS G12C administered first, and the compound that inhibits FAK, SRC and JAK2 administered second.

In some embodiments, the compound that inhibits FAK, SRC and JAK2 is of the formula I

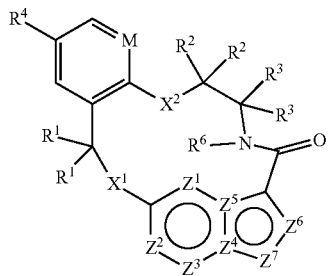

wherein

M is $CR^5$ or N;

$X^1$ and $X^2$ are independently —$C(R^7)(R^8)$—, —S—, —S(O)—, —S(O)$_2$—, —O— or —N($R^9$)—;

each $R^1$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^7$ or —C(O)N$R^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

$R^4$ and $R^5$ are each independently H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$ or —CF$_3$;

$R^6$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —CO$_2$$C_1$-$C_6$ alkyl, —CONH$_2$, —CONH($C_1$-$C_6$ alkyl), —CON($C_1$-$C_6$ alkyl)$_2$, $C_3$-$C_6$ cycloalkyl, or 3- to 7-membered heterocycloalkyl;

each $R^7$ and $R^8$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or 5- to 7-membered heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by deuterium, halogen, $C_1$-$C_6$ alkyl, $C_1$-$C_6$ haloalkyl or —OW;

each $Z^1$, $Z^2$, $Z^3$, $Z^4$, $Z^5$, $Z^6$ or $Z^7$ is independently N, NH, or C($R^{10}$), wherein each $R^{10}$ is independently H, deuterium, halogen, $C_1$-$C_6$ alkyl, —O—$C_1$-$C_6$ alkyl, —OH, —$NH_2$, —NH($C_1$-$C_6$ alkyl), —NH(phenyl), —NH(heteroaryl), —CN, or $CF_3$, and provided that at least one of $Z^1$, $Z^2$, $Z^3$, $Z^4$, $Z^5$, $Z^6$ or $Z^7$ is N or NH;

or a pharmaceutically acceptable salt thereof.

In some embodiments, $R^1$ is H or $C_1$-$C_6$ alkyl. In some embodiments, $R^1$ is H or methyl. In some embodiments, one of $R^1$ is H and the other of $R^1$ is methyl. In some embodiments, $R^2$ is H. In some embodiments, $R^2$ is $C_1$-$C_6$ alkyl. In some embodiments, one of $R^2$ is H and the other of $R^2$ is methyl. In some embodiments, $X^1$ is —$NR^9$—. In some embodiments, $R^9$ is H. In some embodiments, $X^1$ is $CHR^7$. In some embodiments, $R^7$ is H. In some embodiments, $X^2$ is —O—. In some embodiments, $R^6$ is H. In some embodiments, $R^4$ is F. In some embodiments, M is $CR^5$, and $R^5$ is H.

Macrocyclic compounds that have been shown herein to be potent small-molecule multi-target kinase inhibitors showing activity against FAK, SRC and JAK2 include, but are not limited to, (7S,13R)-11-fluoro-7,13-dimethyl-6,7,13,14-tetrahydro-1,15-ethenopyrazolo[4,3-f][1,4,8,10]benzoxatriazacyclotridecin-4(5H)-one (also herein referred to as "Compound 1"), represented by the formula

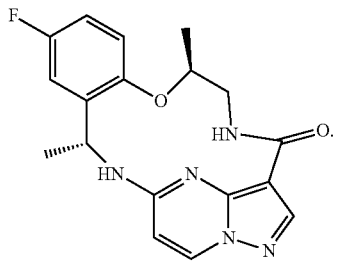

Compound 1 has properties, including anti-tumor properties, which are pharmacologically mediated through inhibition of receptor and non-receptor tyrosine kinases. Compound 1 is disclosed in International Patent Publication WO2015/112806, which is incorporated herein by reference for the preparation of Compound 1.

In some embodiments of the above aspects, the compound that inhibits FAK, SRC and JAK2 is of the formula

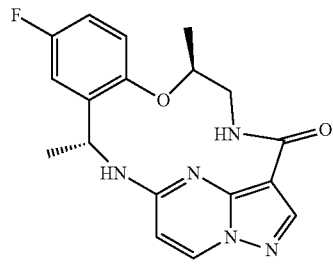 [SMILES: C[C@H]1CNC(=O)c2cnn3ccc(nc23)N[C@H](C)c2cc(F)ccc2O1]

or a pharmaceutically acceptable salt thereof.

It will be appreciated that the cancer can be any cancer that may be mediated by or associated with KRAS, or the upregulation of KRAS, including but not limited to, ALCL, NSCLC, neuroblastoma, inflammatory myofibroblastic tumor, adult renal cell carcinoma, pediatric renal cell carcinoma, breast cancer, triple negative breast, colonic adenocarcinoma, glioblastoma, glioblastoma multiforme, anaplastic thyroid cancer, cholangiocarcinoma, ovarian cancer, colorectal cancer, inflammatory myofibroblastic tumor, angiosarcoma, epithelioid hemangioendothelioma, intrahepatic cholangiocarcinoma, thyroid cancer, spitzoid neoplasms, sarcoma, astrocytoma, brain lower grade glioma, secretory breast carcinoma, mammary analogue carcinoma, acute myeloid leukemia, congenital mesoblastic nephroma, congenital fibrosarcomas, Ph-like acute lymphoblastic leukemia, thyroid carcinoma, head and neck squamous cell carcinoma, pediatric glioma CML, prostate cancer, lung squamous carcinoma, ovarian serous cystadenocarcinoma, skin cutaneous melanoma, castrate-resistant prostate cancer, Hodgkin lymphoma, serous and clear cell endometrial cancer, oral cancer, endometrial cancer, endocrine cancer, skin cancer, gastric cancer, esophageal cancer, laryngeal cancer, pancreatic cancer, colon cancer, bladder cancer, bone cancer, cervical cancer, uterine cancer, testicular cancer, rectal cancer, kidney cancer, liver cancer, stomach cancer and lung cancer.

In some embodiments of the various aspects described herein, the cancer is non-small cell lung cancer mediated by a genetically altered KRAS comprising at least one mutation selected from the group consisting of G12C, G12V, G12D, G12A, G13C, G12S, D12R, D12F, G13D, G13V, G13R, G13E, Q61H, Q61E, Q61L, and Q61R. In some embodiments of the various aspects described herein, the cancer is non-small cell lung cancer mediated by a genetically altered KRAS comprising at least one mutation selected from the group consisting of G12D, G13D, and Q61H; In some embodiments of the various aspects described herein, the cancer is non-small cell lung cancer mediated by a genetically altered KRAS comprising at least one mutation that is not G12A, G12C, G12S, G12V, or Q61K.

In some embodiments of the various aspects described herein, the cancer is colorectal cancer mediated by a genetically altered KRAS comprising at least one mutation selected from the group consisting of G12D, G12V, G13D, A146T, G12C, G12A, G12S, K117N, Q61K, G12R, M72V, S17G, K5R, D69G, G13C, G13R, Q61H, K117E, Q61L, Q61R, K117R, A146V, A146P, K147N, and R97I.

In some embodiments of the various aspects described herein, the cancer is pancreatic cancer mediated by a genetically altered KRAS comprising at least one mutation selected from the group consisting of G12D, G12V, G12R, Q61H, G12C, and G12S.

In some embodiments, the present disclosure provides methods of treating disease in a patient that has received no prior treatment. In some embodiments, the present disclosure provides methods of treating disease in a patient that has received a prior treatment with one or more therapeutic agents. In some embodiments, the patient has been previously treated with one or more chemotherapeutic agents. In still other embodiments, the patent has been previously treated with one or more chemotherapeutic agents or immunotherapies and developed an acquired resistance to the treatment. In still other embodiments, the patent has been previously treated with one or more chemotherapeutic agents or immunotherapies and developed bypass resistance to the treatment. In still other embodiments, the patent has been previously treated with one or more chemotherapeutic agents or immunotherapies and developed bypass resistance to the treatment regulated by FAK, SRC or JAK2, and/or FAK.

Other chemotherapeutic agents which the patient may be been treated with prior to treatment with one or more of the compounds or biological agents described herein include but are not limited to kinase inhibitors, adrenocorticoids and corticosteroids, alkylating agents, peptide and peptidomimetic signal transduction inhibitors, antiandrogens, antiestrogens, androgens, aclamycin and aclamycin derivatives, estrogens, antimetabolites, platinum compounds, amanitins, plant alkaloids, mitomycins, discodermolides, microtubule inhibitors, epothilones, inflammatory and proinflammatory agents, purine analogs, pyrimidine analogs, camptothecins, dolastatins, and or immunotherapies. In some embodiments, the patient has been administered a prior treatment for NSCLC, such as pembrolizumab, platinum, platinum doublet, pemetrexed, carboplatin, paclitaxel, bevacizumab, atezolizumab, abraxane, and combinations thereof. In some embodiments, the patient has been administered a prior treatment for NSCLC cancer that is the standard of care using one or more agents selected from the group consisting of pembrolizumab, platinum, platinum doublet, pemetrexed, carboplatin, paclitaxel, bevacizumab, atezolizumab, and abraxane.

In some embodiments, the patient has been administered a prior treatment for colorectal cancer, such as fluorouracil (5-FU), leucovorin, irinotecan, oxaliplatin, capecitabine, bevacizumab, cetuximab, panitumumab, ziv-aflibercept, ramucirumab, pemborlizumab, nivolumab, ipilimumab, encorafenib, binimetinib, and combinations thereof. In some embodiments, the patient has been administered a prior treatment for colorectal cancer that is the standard of care using one or more agents selected from the group consisting of FOLFOX (i.e. 5-FU+leucovorin+irinotecan)+/−bevacizumab, panitumumab or cetuximab, CAPEOX (i.e. oxaliplatin+capecitabine)+/−bevacizumab, FOLFIRI (i.e. 5-FU+leucovorin+irinotecan)+/−bevacizumab, cetuximab, panitumumab, ziv-aflibercept or ramucirumab, FOLFOXIRI (i.e. irinotecan, oxaliplatin, leucovorin, 5-FU), irinotecan+cetuximab, panitumumab, or amucirumab, pemborlizumab, nivolumab, nivolumab+ipilimumab, encorafenib, and binimetinib. In some embodiments, the patient has been administered a prior treatment for pancreatic cancer, such as fluorouracil (5-FU), leucovorin, irinotecan, liposomal irinotecan, oxaliplatin, gemcitabine, abraxane, erlotinib, capecitabine, and combinations thereof.

In some embodiments, the patient has been administered a prior treatment for pancreatic cancer that is the standard of care using one or more agents selected from the group consisting of FOLFIRINOX (i.e. 5-FU+leucovorin+irinotecan+oxaliplatin), gemcitabine+abraxane, gemcitabine+erlotinib, gemcitabine, 5-FU+liposomal irinotecan, FOLFIRI (i.e. 5-FU+leucovorin+irinotecan), FOLFOX (i.e. 5-FU, oxaliplatin, leucovorin), and capecitabine+/−oxaliplatin.

In some embodiments, the patient has been administered a prior treatment for uterine cancer (a.k.a. endometrial cancer), such as carboplatin, cisplatin, paclitaxel, docetaxel, doxorubicin, liposomal doxorubicin, trastuzumab, topotecan, bevacizumab, temsirolimus tamoxifen, fulvestrant, an aromatase inhibitor, and combinations thereof. In some embodiments, the patient has been administered a prior treatment for pancreatic cancer that is the standard of care using one or more agents selected from the group consisting of carboplatin+paclitaxel+/−trastuzumab, carboplatin or cisplatin+docetaxel, doxorubicin, or paclitaxel, liposomal doxorubicin, topotecan, bevacizumab, temsirolimus tamoxifen, fulvestrant, and an aromatase inhibitor.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 2 g daily, or about 1 mg to 50 mg daily, or about 50 to 250 mg daily, or about 250 mg to 1 g daily. An alternative exemplary dose is in the range of about from about 0.1 mg/kg to 1 g/kg, or about 0.1 mg/kg to 5 mg/kg, or about 0.1 mg/kg to 1 mg/kg, or about 0.1 mg/kg to 0.6 mg/kg. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to affect transdermal delivery.

Dosing and Administration

In some embodiments of the methods and compositions described herein, a therapeutically effective amount of one or more compounds that inhibits FAK, SRC, and/or JAK2 in combination with a therapeutically effective amount of tametinib is administered to a host animal, such as a human patient, in need of treatment for cancer. In some embodiments of the methods and compositions described herein, a therapeutically effective amount of a compound that inhibits FAK, SRC, and JAK2 in combination with a therapeutically effective amount of trametinib is administered to a host animal, such as a human patient, in need of treatment for cancer.

As used herein, the term "therapeutically effective amount" refers to that amount of active compound or pharmaceutical agent that elicits the biological or medicinal response in a patient, which includes alleviation of the symptoms of the disease or disorder being treated. In one aspect, the therapeutically effective amount is that which may treat or alleviate the disease or symptoms. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors.

In some embodiments, a therapeutically effective amount of the combination can be a synergistic combination that provides an enhanced response to treatment with the combination when compared to when the one or more compounds that inhibits FAK, SRC, and/or JAK2 and trametinib are administered individually. In some embodiments, the synergistic effect provided by the administration of a therapeutically effective amount of the combination of the one or more compounds that inhibits FAK, SRC, and/or JAK2 and trametinib is a dose response that is more than additive compared to the response of the each of the components of the combination administered individually.

In some embodiments, an exemplary dose for each compound or agent individually in the various methods and compositions described herein is in the range of about from about 0.1 mg to about 3 g, or about 0.5 mg to about 2.5 mg, or about 1 mg to about 50 mg, or about 50 to about 250 mg, or about 150 to about 500 mg, or about 150 to about 250 mg, or about 250 mg to about 1 g, or about 100 mg to about 2 g, or about 500 mg to about 2 g, or about 500 mg to about 1 g. It will be appreciated that all possible subranges within the dose ranges described above are contemplated and described herein. For example, a dose range of about 150 to about 500 mg for a compound that inhibits FAK, SRC, and JAK2 provided in the methods and compositions described herein includes doses of about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, including all possible doses and ranges as may be required based on such factors for determining a therapeutically effective amount as described herein. In some embodiments, the compound that inhibits FAK, SRC, and JAK2, in particular Compound 1, provided in the methods and compositions described herein can be dosed at about 40 mg, about 80 mg, about '120 mg, or about 160 mg.

In some embodiments, trametinib can be administered in an amount of from about 0.3 mg daily to about 2.5 mg daily, or about 0.5 mg to about 2.5 mg, or about 1 mg to about 2 mg. In some embodiments, trametinib can be administered in an amount of about 0.5 mg, or about 2.0 mg.

In some embodiments, an exemplary dose for each compound or agent individually in the various methods and compositions described herein is in the range of about from about 0.1 mg to about 3 g daily, or about 1 mg to about 50 mg daily, or about 50 to about 250 mg daily, or about 150 to about 500 mg daily, or about 150 to about 250 mg daily, or about 250 mg to about 1 g daily, or about 100 mg to about 2 g daily, or about 500 mg to about 2 g daily, or about 500 mg to about 1 g daily. It will be appreciated that all possible subranges within the daily dose ranges described above are contemplated and described herein. For example, a dose range of about 150 to about 500 mg daily for a compound that inhibits FAK, SRC, and JAK2 provided in the methods and compositions described herein includes doses of about 150 mg daily, about 160 mg daily, about 170 mg daily, about 180 mg daily, about 190 mg daily, about 200 mg daily, about 210 mg daily, about 220 mg daily, about 230 mg daily, about 240 mg daily, and about 250 mg daily, about 260 mg daily, about 270 mg daily, about 280 mg daily, about 290 mg daily, about 300 mg daily, about 310 mg daily, about 320 mg daily, about 330 mg daily, about 340 mg daily, about 350 mg daily, about 360 mg daily, about 370 mg daily, about 380 mg daily, about 390 mg daily, about 400 mg daily, about 410 mg daily, about 420 mg daily, about 430 mg daily, about 440 mg daily, about 450 mg daily, about 460 mg daily, about 470 mg daily, about 480 mg daily, about 490 mg daily, about 500 mg daily, including all possible doses and ranges as may be required based on such factors for determining a therapeutically effective amount as described herein. In some embodiments, the compound that inhibits FAK, SRC, and JAK2, in particular Compound 1, provided in the methods and compositions described herein can be dosed at about 40 mg daily, about 80 mg daily, about '120 mg daily, or about 160 mg daily.

In some embodiments, trametinib can be administered in an amount of from about 0.3 mg daily to about 2.5 mg daily, or about 0.5 mg daily to about 2.5 mg daily, or about 1 mg daily to about 2 mg daily. In some embodiments, trametinib can be administered in an amount of about 0.5 mg daily, or about 2.0 mg daily.

In some embodiments, an alternative exemplary dose for each compound or agent individually in the various methods and compositions described herein is in the range of about from about 0.001 mg/kg to about 1 g/kg, or about 0.05 mg/kg to about 50 mg/kg, or about 0.05 mg/kg to about 25 mg/kg, or about 1.0 mg/kg to about 10 mg/kg, or about 1.0 mg/kg to about 5 mg/kg, or about 0.1 mg/kg to about 5 mg/kg, or about 0.1 mg/kg to about 1 mg/kg, or about 0.1 mg/kg to about 0.6 mg/kg. It will be appreciated that all possible subranges within the dose ranges described above are contemplated and described herein. For example, a dose range of about 1.0 mg/kg to about 10 mg/kg for a compound that inhibits FAK, SRC, and JAK2, in particular Compound 1, provided in the methods and compositions described herein includes doses of about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, and about 10.0 mg/kg, including all possible doses and ranges as may be required based on such factors for determining a therapeutically effective amount as described herein.

In some embodiments, a MEK inhibitor such as trametinib can be administered in an amount of from about 0.004 mg/kg to about 0.2 mg/kg, or about 0.006 mg/kg to about 0.1 mg/kg.

In some embodiments, an alternative exemplary dose for each compound or agent individually in the various methods and compositions described herein is in the range of about from about 0.1 mg/kg to about 1 g/kg daily, or about 0.5 mg/kg to about 50 mg/kg daily, or about 0.5 mg/kg to about 25 mg/kg daily, or about 1.0 mg/kg to about 10 mg/kg daily, or about 1.0 mg/kg to about 5 mg/kg daily, or about 0.1 mg/kg to about 5 mg/kg daily, or about 0.1 mg/kg to about 1 mg/kg daily, or about 0.1 mg/kg to about 0.6 mg/kg daily. It will be appreciated that all possible subranges within the dose ranges described above are contemplated and described herein. For example, a dose range of about 1.0 mg/kg to about 10 mg/kg daily for a compound that inhibits FAK, SRC, and JAK2, in particular Compound 1, provided in the methods and compositions described herein includes doses of about 1.0 mg/kg daily, about 2.0 mg/kg daily, about 3.0 mg/kg daily, about 4.0 mg/kg daily, about 5.0 mg/kg daily, about 6.0 mg/kg daily, about 7.0 mg/kg daily, about 8.0 mg/kg daily, about 9.0 mg/kg daily, and about 10.0 mg/kg daily, including all possible doses and ranges as may be required based on such factors for determining a therapeutically effective amount as described herein.

In some embodiments, a MEK inhibitor such as trametinib can be administered in an amount of from about 0.004 mg/kg daily to about 0.2 mg/kg daily, or about 0.006 mg/kg daily to about 0.1 mg/kg daily.

It will be appreciated that various dosing schedules for administration of each compound or agent administered individually (or together) can be applied to the methods and compositions described herein. It will be further appreciated that a dosing schedule for each compound or agent administered individually (or together) in the various methods and compositions described herein can be defined by cycles of the dosing schedule, where such cycles are defined by the number of days of treatment, number of doses of each compound or agent individually (or together), the total dose of each compound or agent individually (or together), and the like. In some embodiments, a host animal, such as a human patient in need of treatment, can be administered each compound or agent administered individually (or together) for at least one cycle, for at least two cycles, for at least three cycles, for at least four cycles, and the like. Alternatively, in some embodiments, a host animal, such as a human patient in need of treatment, can be administered each compound or agent administered individually (or together) for from 1 to about 50 cycles, from 1 to about 25 cycles, from 1 to about 20 cycles, from 1 to about 10 cycles, and the like. It will be appreciate that, in some embodiments, a dosing schedule for each compound or agent administered individually (or together) in the various methods and compositions described herein can include a holiday period during which no compound or agent is administered, and such holiday period can be measured in days. In some embodiments, a dosing schedule for each compound or agent administered individually (or together) in the various methods and compositions described herein can be defined by a number of cycles as described herein, followed by a holiday period, followed by another number of cycles as described herein.

In some embodiments, an exemplary dosing schedule for each compound or agent individually in the various methods and compositions described herein can include administration of a single daily dose (QD) or divided dosage units (e.g., BID (twice daily), TID (three times daily), QID (four times daily)). In some embodiments, a dosing schedule for each compound or agent in the various methods and compositions described herein can be the same, such as all compounds or agents in the various methods and compositions described herein are administered QD, BID, or the like. In some embodiments, a dosing schedule for each compound or agent in the various methods and compositions described herein can be different from each other, such as one compound or agent in the various methods and compositions described herein is administered QD, and another compound or agent in the various methods and compositions described herein is administered BID. In some embodiments, a dosing schedule for each compound or agent in the various methods and compositions described herein can vary within a cycle, such as one compound or agent in the various methods and compositions described herein administered QD for a set number of days (e.g. QD for 1 day, 2 days, 3 days, 4 days, etc) followed by BID for a set number of days (e.g. BID for 1 day, 2 days, 3 days, 4 days, etc). In some embodiments, a dosing schedule for each compound or agent in the various methods and compositions described herein can be the same or different within a cycle, such as one compound or agent in the various methods and compositions described herein administered QD for a set number of days (e.g. QD for 1 day, 2 days, 3 days, 4 days, etc) followed by BID for a set number of days (e.g. BID for 1 day, 2 days, 3 days, 4 days, etc) to match the length of the cycle, and another compound or agent administered BID for a set number of days to match the length of the cycle.

In some embodiments, the compound that inhibits FAK, SRC, and JAK2, in particular Compound 1, and a MEK inhibitor such as trametinib are administered at the same time. In some embodiments, the compound that inhibits FAK, SRC, and JAK2, in particular Compound 1, and a MEK inhibitor such as trametinib are individually formulated, and administered at the same time. In some embodiments, the compound that inhibits FAK, SRC, and JAK2, in particular Compound 1, and trametinib are individually formulated, and administered in sequence. In some embodiments, the sequential administration of the compound that inhibits FAK, SRC, and JAK2, in particular Compound 1, and a MEK inhibitor such as trametinib can be accomplished with the compound that inhibits FAK, SRC and JAK2, in particular Compound 1, administered first (e.g. in the morning), and trametinib administered second (e.g. in the afternoon or evening). In some embodiments, the sequential administration of the compound that inhibits FAK, SRC, and JAK2, in particular Compound 1, and a MEK inhibitor such as trametinib can be accomplished with trametinib administered first (e.g. in the morning), and the compound that inhibits FAK, SRC, and JAK2, in particular Compound 1, administered second (e.g. in the afternoon or evening).

In some embodiments, an exemplary dosing schedule for each compound or agent individually in the various methods and compositions described herein can include administration of a compound that inhibits FAK, SRC, and JAK2, in particular Compound 1, at a dose level of from about 100 mg to about 300 mg QD for at least one day followed by a dose level of from about 100 mg to about 300 mg BID and trametinib at a dose level of from about 0.5 mg to about 2.5 mg QD. In some embodiments, the administration of a compound that inhibits FAK, SRC, and JAK2, in particular Compound 1, and trametinib on the dose schedule described above can be given for from 1 to about 20 cycles, where each cycle is from about 5 to about 20 days. In some embodiments, the administration of a compound that inhibits FAK, SRC, and JAK2, in particular Compound 1, and trametinib on the dose schedule described above can be given for a set number of days, such as from about 20 to about 200 days, perpetually, or until treatment is stopped by a treating physician.

EXAMPLES

Chemicals and Reagents

Compound 1 was prepared according to the methods described in WO2015/112806, see specifically Example 90 as described therein. WO2015/112806 is incorporated herein by reference for the preparation of Compounds 1.

Trametinib was purchased from MedChemExpress. Drugs were prepared in dimethyl sulfoxide (DMSO) at a concentration of 10-100 mmol/L stock solutions and stored at −20° C. Further dilutions were made in culture medium to final concentration before use. Phospho-STAT3 (Tyr705), phospho-AKT (Ser473), phospho-ERK1/2 (Thr202/Tyr204), phospho-FAK (Tyr576/577), STAT3, FAK, SRC, AKT, ERK, PARP, cleaved caspase-3, tubulin, and actin were purchased from Cell Signaling Technology (Beverly, Mass.).

Cell Lines

Human NSCLC cell lines H358, H23, H2122, H1373 and H1792, harboring KRAS G12C mutation, were purchased from the American Type Culture Collection (ATCC). Human NSCLC cell line H441 with KRAS G12V mutation and H460 with KRAS Q61H mutation were also purchased from ATCC. The cell lines described above were maintained in RPMI (Roswell Park Memorial Institute medium) 1640 supplemented with 1% penicillin/streptomycin/glutamine (Gibco) and 10% fetal bovine serum (FBS) (Gibco) in 5% $CO_2$, 37° C. cell culture incubator. The human CRC cell line HCT-116 with KRAS G13D was purchased from ATCC and maintained in DMEM supplemented with 1% penicillin/streptomycin/and 10% FBS (Gibco) in 5% $CO_2$, 37° C. cell culture incubator. The human pancreatic cell line PSN1 with KRAS G12R was purchased from ATCC and maintained in RPMI 1640 supplemented with 1% penicillin/streptomycin/ and 10% FBS (Gibco) in 5% $CO_2$, 37° C. cell culture incubator. All cell lines were routinely evaluated for *Mycoplasma* contamination.

Subcutaneous Xenograft Models in Immune Compromised Mice

Female athymic nude mice (5-8 weeks of age) were obtained from Charles River Laboratory and were housed in Innovive IVC disposable cages on HEPA filtered ventilated racks with ad libitum access to rodent chow and water. About five million cells in 100 µL serum-free medium supplemented with 50% matrigel (Corning, Inc) were implanted subcutaneously in the right flank region of the mouse. Tumor size and body weight were measured on designated days.

Tumor size was measured with an electronic caliper and tumor volume was calculated as the product of length*width$^2$*0.5. Mice were randomized by tumor size into treatment groups when tumor volume reached about 200 mm$^3$. Compound 1 was administered orally twice a day at determined doses and trametinib was administered orally once a day at determined doses.

Tumor Processing and Immunoblotting for In Vivo Pharmacodynamic Studies

Mice bearing xenograft tumors were humanely euthanized and tumors were resected and snap frozen in liquid nitrogen and stored at −80° C. Frozen tumor samples were processed at 4° C. in RIPA buffer to extract proteins. Protein concentration of the lysate was determined by Rapid Gold BCA Protein Assay (Life Technologies, Inc.) and lysate were diluted to ensure the same protein concentration across samples. SDS loading samples were prepared by adding one volume of 4× LDS Sample Buffer (Life Technologies, Inc.) to three volumes of diluted protein lysate. Tumor SDS protein samples were processed by SDS-PAGE and immunoblotted appropriate primary antibodies, followed by detection using HRP conjugated secondary antibodies. The signals from immunoblot were detected by C-DiGit Blot Scanner from LI-COR using the Image Studio Digit software (LI-COR).

Example 1: NSCLC Cell Viability Assay

One to two thousand cells per well were seeded in 96 or 384 well white plate, and then treated with indicated compounds for 72-120 hours (37° C., 5% $CO_2$). Cell proliferation was measured using CellTiter-Glo luciferase-based ATP detection assay (Promega) following the manufactures's protocol. $IC_{50}$ determinations were performed using GraphPad Prism software (GraphPad, Inc., San Diego, Calif.).

Results showing cell viability % of the MEK1/2 inhibitor (trametinib), Compound 1, and the combination of the MEK1/2 inhibitor (trametinib) with Compound 1 (1 μM) in mutant KRAS NSCLC cell lines are shown in FIG. 1a-1x. The $IC_{50}$ values are summarized in Table 1. Although Calu-1, COR-L23, HCC1588, LCLC-97TM1, LU2512, NCI-H1155, NCI-H1373, NCI-H1573, SK-LU-1, and SW1573 NSCLC cell line endogenously expresses KRAS mutations, the MEK inhibitor trametinib demonstrated weak-to-no detectable inhibition of the cell proliferation. We investigated the synergistic effect of Compound 1 (1 μM) in combination with trametinib on cell proliferation in NSCLC cell lines with a range of KRAS mutations. Compound 1 alone had only weak inhibition activity in most of the tested NSCLC cell line with $IC_{50}$ ranges from 0.82 to 5 μM. A strong synergy was observed with the combination of trametinib and Compound 1. Compound 1 at 1 μM concentration shifted trametinib's $IC_{50}$ from 100 nM to 3 nM against H358 cell proliferation. The combination shifted the trametinib $IC_{50}$ to single digit $IC_{50}$ values in 18 of 24 mutant KRAS NSCLC cell lines tested which encompassed the following KRAS mutations: G12C, G12D, G12S, G12V, G13D, Q61K, and Q61H.

TABLE 1

| Cell lines | Compound 1 ($IC_{50}$ μM) | Trametinib ($IC_{50}$ μM) | Trametinib + 1 μM Compound 1 ($IC_{50}$ μM) | KRAS Mutation |
|---|---|---|---|---|
| A-427 | 0.83 | 0.06 | <0.001 | G12D |
| A549 | 1.36 | 0.055 | <0.001 | G12S |
| Calu-1 | 2.3 | >10 | 0.01 | G12C |
| Calu-6 | 1.47 | 0.012 | 0.001 | Q61K |
| COR-L23 | 2.2 | 0.164 | 0.001 | G12V |
| DV-90 | 7.27 | 0.014 | 0.004 | G13D |
| HCC1588 | 0.82 | >10 | <0.001 | G12D |
| LCLC-97TM1 | 0.93 | 0.344 | <0.001 | G12V |
| LU2512 | 2.5 | 2.529 | 0.252 | G12C |
| NCI-H1155 | NA | >10 | 10 | Q61H |
| NCI-H1373 | 4.2 | >10 | 0.007 | G12C |
| NCI-H1573 | NA | >10 | 0.129 | G12A |
| NCI-H1792 | 1.32 | 0.051 | <0.001 | G12C |
| NCI-H1944 | 2.62 | >10 | 0.005 | G13D |
| NCI-H2009 | 2.28 | >10 | 0.019 | G12A |
| NCI-H2122 | 1.16 | 0.01 | <0.001 | G12C |
| NCI-H23 | 3.42 | 0.063 | 0.002 | G12C |
| NCI-H358 | 2.5 | 0.1 | 0.003 | G12C |
| NCI-H441 | 5.21 | >10 | 0.001 | G12V |
| NCI-H460 | 1.22 | 0.07 | <0.001 | Q61H |
| NCI-H727 | 4.53 | 0.003 | <0.001 | G12V |
| SK-LU-1 | 0.95 | >10 | <0.001 | G12D |
| SW1573 | 2.59 | >10 | 3.701 | G12C |
| SW900 | 2.08 | 0.074 | 0.005 | G12V |

Example 2. Apoptosis Assays

Figure 1B:
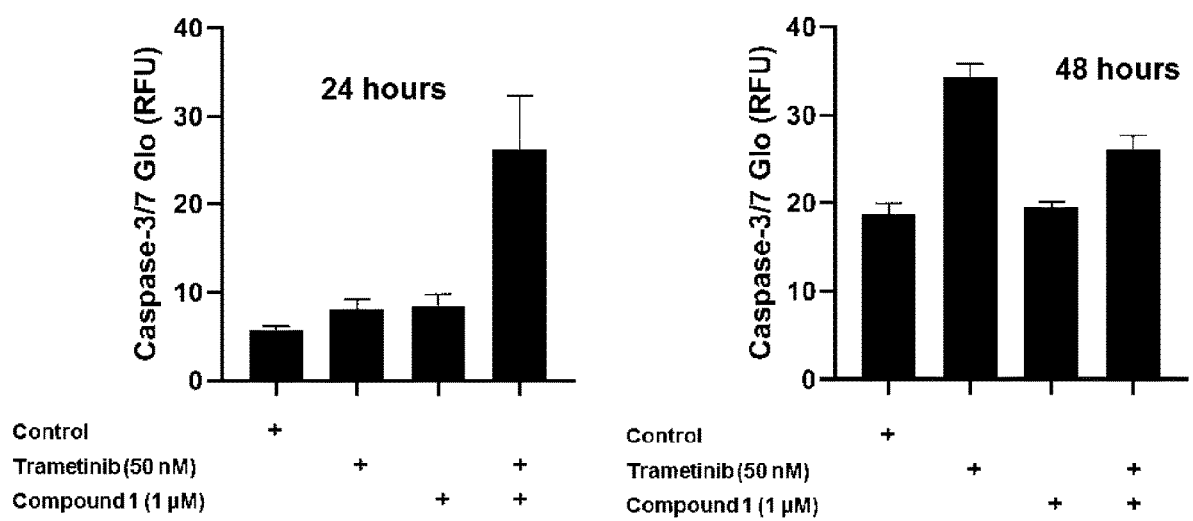
FIG. 1b shows the level of caspase-3/7 activated by Compound 1 (1 μM), trametinib (50 nM) and Compound 1 (1 μM)+trametinib (50 nM) at 24 hr and 48 hr timepoints in Calu-6 cells with KRAS Q61K mutation.
Figure 1C:
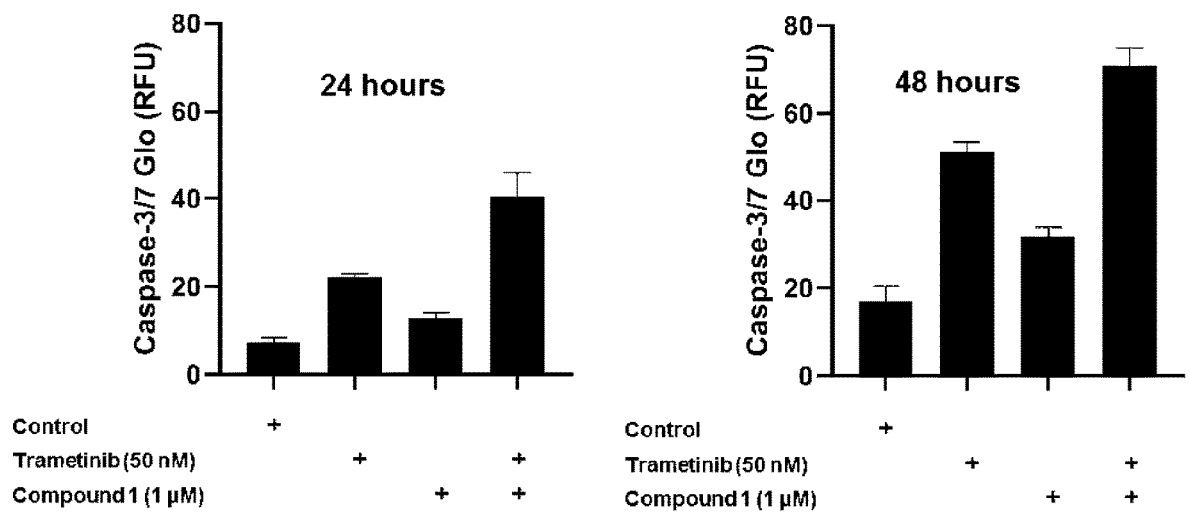
FIG. 1c shows the level of caspase-3/7 activated by Compound 1 (1 μM), trametinib (50 nM) and Compound 1 (1 μM)+trametinib (50 nM) at 24 hr and 48 hr timepoints in NCI-H2122 cells with KRAS G12C mutation.
Figure 1D:
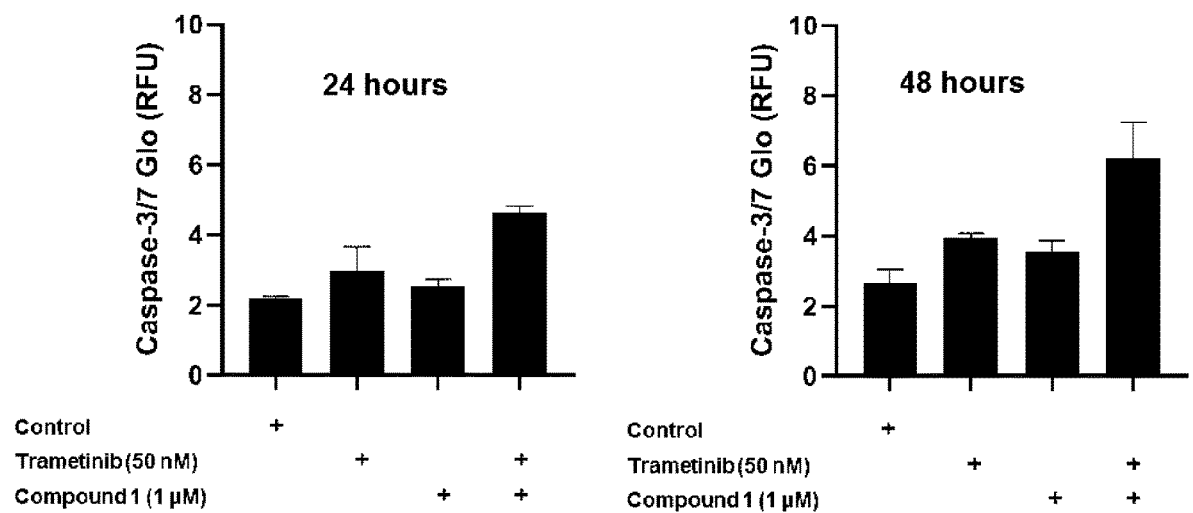
FIG. 1d shows the level of caspase-3/7 activated by Compound 1 (1 μM), trametinib (50 nM) and Compound 1 (1 μM)+trametinib (50 nM) at 24 hr and 48 hr timepoints in NCI-H441 cells with KRAS G12V mutation.

Two thousand cells per well were seeded in 384 well white plate, and then treated with compounds for 24 or 48 hours (37° C., 5% $CO_2$). Cell caspase-3/7 activity, a major hallmark of apoptosis, was measured using Caspase-Glo® 3/7 detection assay (Promega) following the manufactures's protocol. Results showed the increase of caspase-3/7 activity with 24 and 48 hour treatments of trametinib (50 nM), Compound 1 (1 μM), and the combination of trametinib (50 nM) with Compound 1 (1 μM) in NSCLC cell lines harboring a KRAS G12C mutation (H358, H2122), a KRAS Q61H mutation (Calu-6) and KRAS G12V mutation (H441) are shown in FIG. 1a-1d. Compound 1 alone causes modest increases in caspase-3/7 activity in NCI-H358, NCI-H2122 NSCLC cell lines after 48 hours of treatment (FIG. 1a, 1c). trametinib alone increased caspase-3/7 activity with H358, Calu-6, H2122 NSCLC cell lines after 48 hours of treatment (FIG. 1a-1c). The combination of Compound 1 with trametinib caused significantly more caspase-3/7 activation compared to trametinib treatment alone for NSCLC cells with all tested mutant KRAS cell lines at both 24 and 48 hour timepoints (FIG. 1a 1d).

Cleaved PARP and cleaved caspase-3 were evaluated as biomarkers of apoptosis. Half a million cells per well were seeded in 24 well plate for 24 hrs, and then treated with compounds for 4, 24 or 48 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1x Halt protease and phosphatase inhibitors (Thermo Scientific). Protein lysates (approximately 20 μg) was resolved on 4-12% Bolt Bis-Tris precasted gels with MES running buffer (Life Technologies), transferred to nitrocellulose membranes using Trans-Blot Turbo Transfer System (Bio-Rad) and detected with antibodies targeting PARP, Cleaved caspase-3, tubulin and actin (Cell Signaling Technology). Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences). Results in the NCI-H358 and NCI-H2122 KRAS G12C NSCLC cell lines demonstrate significant increases in cleaved PARP and cleaved caspase-3 after both 24 hour and 48 hour treatments with the combination of trametinib (100 nM) and Compound 1 (1 μM). Treatment with trametinib alone (100 nM) or Compound 1 alone (1 μM) resulted in small increases in cleaved PARP and cleaved caspase-3 Protein. Results in H2122 KRAS G12C NSCLC Demonstrated a Significant Increase in Cleaved PARP 24 hour treatment with Compound 1 (1 μM).

Example 3. Immunoblotting for Cellular Kinase Phosphorylation Assays

Half a million cells per well were seeded in 24 well plate for 24 hrs, and then treated with compounds for 4, 24 or 48 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1x Halt protease and phosphatase inhibitors (Thermo Scientific). Protein lysates (approximately 20 μg) was resolved on 4-12% Bolt Bis-Tris precasted gels with IVIES running buffer (Life Technologies), transferred to nitrocellulose membranes using Trans-Blot Turbo Transfer System (Bio-Rad) and detected with antibodies targeting phosphorylated STAT3, FAK, SRC, AKT, ERK, (Cell Signaling Technology), total STAT3, FAK, SRC, AKT, and ERK, (Cell Signaling Technology) Antibodies were typically incubated overnight at 4° C. with gentle shake, followed by washes and incubation with the appropriate HRP-conjugated secondary antibodies. Membranes were incubated with chemiluminescent substrate for 5 min at room temperature (SuperSignal West Femto, Thermo Scientific). The chemiluminescent images were acquired with a C-DiGit Imaging System (LI-COR Biosciences).

Results in Calu-6 KRAS Q61K NSCLC show that Compound 1 alone (1 µM) suppresses protein levels of phospho-AKT (pAKT), phospho-FAK (pFAK), phospho-SRC (pSRC), phospho-STAT3 (pSTAT3) at 4, 24 and 48 h time points. Trametinib treatment (50 µM) potently inhibited pERK but did not suppress pAKT, pFAK, pSRC, or pSTAT3 protein levels at any time point. The combination of Compound 1 (1 µM) and trametinib (50 µM) potently suppresses pERK, pAKT, pFAK, pSRC, and pSTAT3 protein levels. The combination of suppression of these signaling nodes supports the significantly increased activation of apoptosis observed with the combination treatment.

Further immunoblotting experiments showed that 1 µM Compound 1 suppressed the induction of phosphorylated AKT by 50 nM trametinib in Calu-6 cells harboring a KRAS Q61K mutation.

Additionally, 1 µM Compound 1 more effectively suppressed trametinib-induced phosphoAKT protein level compared to dasatinib (SRC inhibitor), defactinib (FAK inhibitor), or ruxolitinib (JAK1/2 inhibitor) in Calu-6 cells harboring a KRAS Q61K mutation.

Further, Compound 1 demonstrated a dose-dependent response from 0 to 3000 nM concentration for the inhibition of phosphorylation of AKT, ERK, FAK, STAT3 in NCI-H358 cells harboring a KRAS G12C mutation.

Figure 2A:
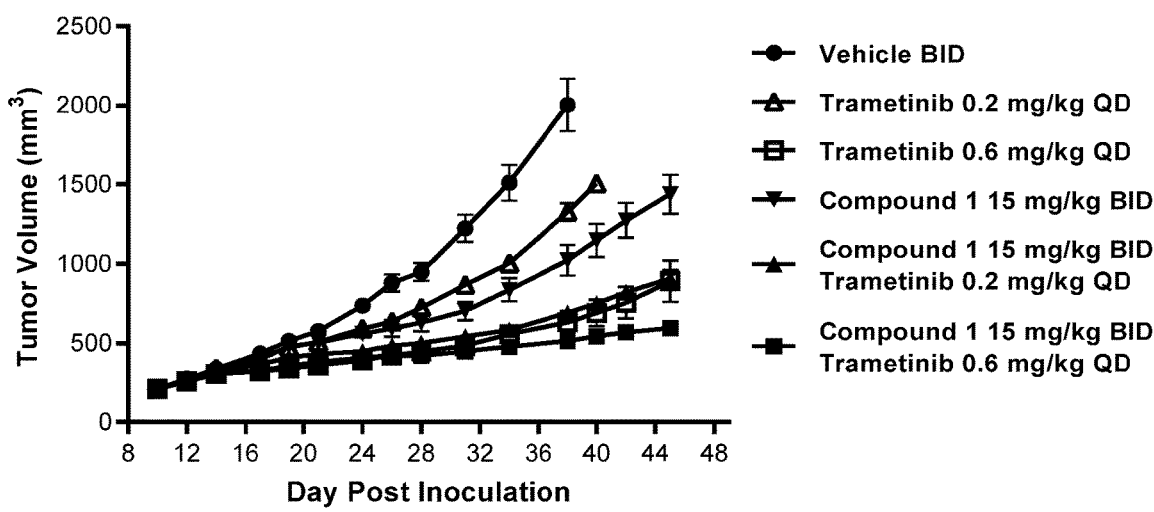
FIG. 2a is a chart showing the antitumor effect of Compound 1 in combination with trametinib in Calu-6 cell-derived xenograft tumors harboring the $KRAS^{Q61K}$ mutation in athymic nude mice. (●) Control; (▼) Compound 1 (15 mg/kg BID); (Δ) Trametinib (0.2 mg/kg QD); (▲) Compound 1 (15 mg/kg BID) plus Trametinib (0.2 mg/kg QD); (□) Trametinib (0.6 mg/kg QD); (■) Compound 1 (15 mg/kg BID) plus Trametinib (0.6 mg/kg QD).
Figure 2B:
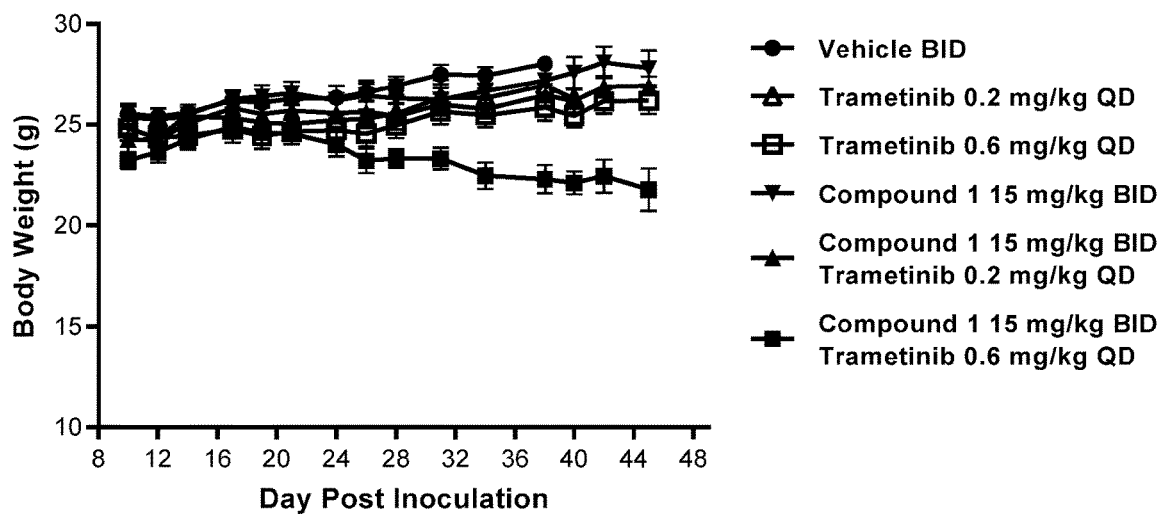
Figure 3:
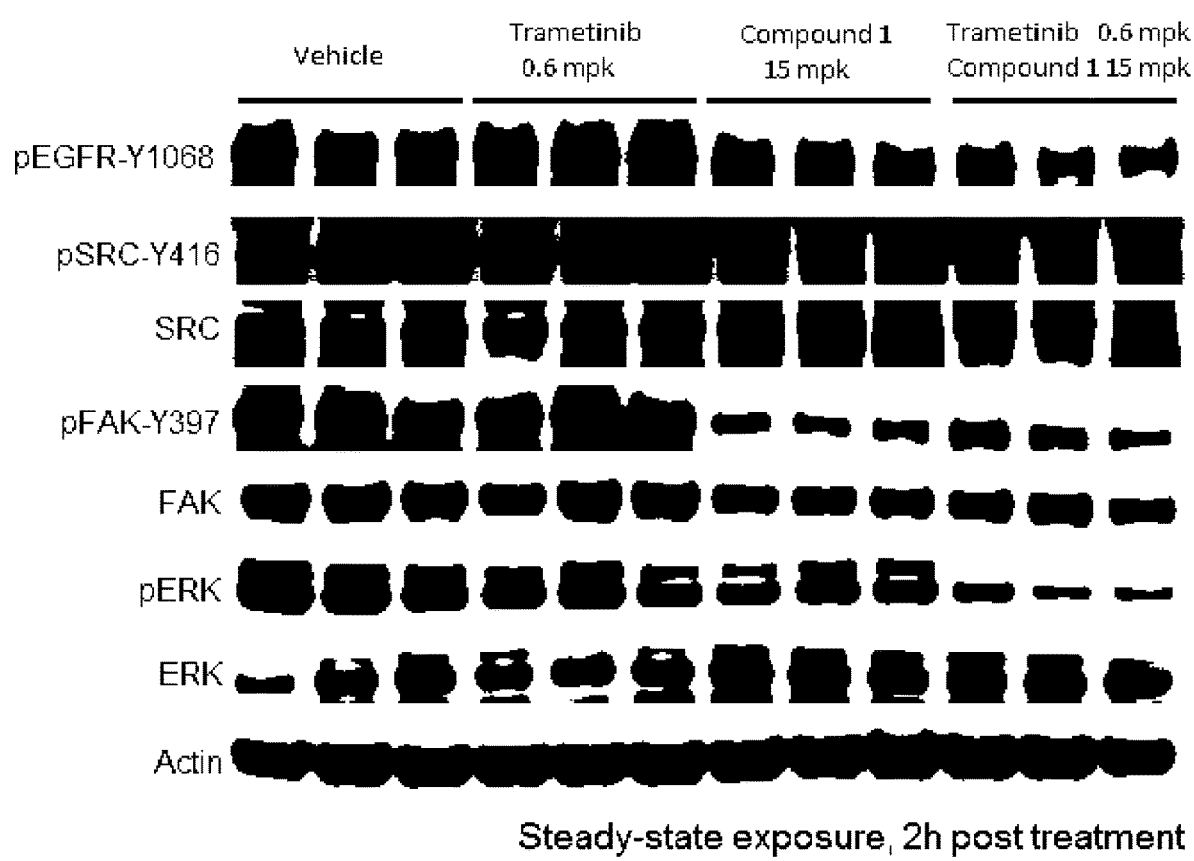
FIG. 3 shows pharmacodynamic modulation of phosphor-EGFR, phosphor-SRC, phosphor-FAK, and phosphoERK following treatment with the MEK1/2 inhibitor trametinib (0.6 mg/kg QD), Compound 1 (15 mg/kg BID), and trametinib (0.6 mg/kg QD) in the presence of Compound 1 (15 mg/kg BID) in Calu-6 cell-derived xenograft tumors harboring the $KRAS^{Q61K}$ mutation. mpk: mg/kg.

Example 4. Efficacy and Pharmacodynamic Modulation in Mouse Tumor Xenograft Models Effect of Compound 1 in Combination with Trametinib in Calu-6 Cell-Derived Xenograft Tumors Calu-6 cells harboring a KRAS Q61K mutation. Athymic nude mice bearing Calu-6 cell-derived tumors were randomized to six groups and treated with vehicle BID, Compound 1 BID at 15 mg/kg, trametinib QD at 0.2 mg/kg, Compound 1 BID at 15 mg/kg in combination with trametinib QD at 0.2 mg/kg, trametinib QD at 0.6 mg/kg, and Compound 1 BID at 15 mg/kg in combination with trametinib QD at 0.6 mg/kg, respectively. The tumor volume (TMV) vs time data are shown as mean±sem in FIG. 2a. At the data cut off on day 38 when the vehicle treated group was euthanized, treatment with Compound 1 in combination with trametinib at 0.2 mg/kg dose level significantly reduced tumor volume compared to the treatment with Compound 1 only or the treatment with trametinib (0.2 mg/kg) only ($p<0.05$, post hoc Dunnett's multiple comparison test following two-way ANOVA with six groups on day 31, 34, and 38). At the data cut off on day 45, comparing the data from groups treated with Compound 1 BID at 15 mg/kg, trametinib QD at 0.6 mg/kg, and Compound 1 BID at 15 mg/kg in combination with trametinib QD at 0.6 mg/kg revealed that the treatment with Compound 1 in combination with trametinib at 0.6 mg/kg dose level significantly reduced tumor volume compared to the treatment with Compound 1 only or the treatment with trametinib (0.6 mg/kg) only ($p<0.05$, post hoc Dunnett's multiple comparison test following two-way ANOVA with three groups on day 42 and 45). Body weight of the mice were measured during treatment and are shown as mean±sem in FIG. 2b. Although the body weight change over time in the group mice treated with Compound 1 in combination with trametinib at 0.6 mg/kg dose level was significantly different from other groups, the body weights at the end of treatment were not significantly different from those at the baseline before treatment started ($p>0.1$, Wilcoxon matched-pairs signed rank test), with the mean body weight slightly reduced to about 94% of baseline level following 35 days of treatment.

Pharmacodynamic Effect of Compound 1 in Combination with Trametinib in Calu-6 Cell-Derived Xenograft Tumors To evaluate the pharmacodynamic effect of Compound 1 in combination with trametinib in Calu-6 cell-derived xenograft tumors, tumor lysate was prepared and analyzed by immunoblotting using antibodies against the candidate molecules selected from signaling pathways that can be potentially modified by Compound 1 and/or trametinib (FIG. 9). The inhibitory activities of Compound 1 against SRC and FAK were demonstrated by the reduction of phosphorylated SRC and FAK signals in tumors treated with Compound 1 at 15 mg/kg twice a day (BID) either as the single agent or in combination with trametinib at 0.6 mg/kg. In addition, Compound 1 in combination with trametinib reduced the phosphorylated ERK signal, a key pathway involved in cell proliferation and survival. Finally, phosphorylated EGFR appeared to be induced by treatment of trametinib. Compound 1 treatment either in combination with trametinib or as a single agent reduced the EGFR activity.

Example 5: CRC Cell Viability Assay

Two thousand cells per well were seeded in 96 or 384 well white plate, and then treated with indicated compounds for 72 hours (37° C., 5% $CO_2$). Cell proliferation was measured using CellTiter-Glo luciferase-based ATP detection assay (Promega) following the manufacture's protocol. $IC_{50}$ determinations were performed using GraphPad Prism software (GraphPad, Inc., San Diego, Calif.).

Results showing cell viability % of the MEK1/2 inhibitor (trametinib), Compound 1, and the combination of the MEK1/2 inhibitor (trametinib) with Compound 1 (1 µM) in mutant KRAS colorectal cancer (CRC) cell lines were evaluated. The $IC_{50}$ values are summarized in Table 2.

TABLE 2

| CRC mutant KRAS cell lines | Compound 1 ($IC_{50}$ µM) | Trametinib ($IC_{50}$ µM) | Trametinib + Compound 1 (1 µM) ($IC_{50}$ µM) | KRAS mutation |
|---|---|---|---|---|
| DLD-1 | 1.37 | 1.39 | 0.119 | G13D |
| HCT-116 | 1.66 | 0.024 | <0.001 | G13D |
| HCT-15 | 1.66 | 1.81 | 0.063 | G13D |
| LoVo | 3.07 | 0.006 | 0.000 | G13D |
| LS1034 | 3.85 | 0.013 | 0.004 | A146T |
| LS123 | 3.06 | 10 | 0.053 | G12S |
| LS180 | 18.6 | >10 | 0.053 | G12D |
| LS513 | 2.22 | 0.006 | 0.002 | G12D |
| NCI-H716 | 0.667 | 0.459 | <0.001 | R97I |
| NCI-H747 | 1.94 | 0.011 | 0.001 | G13D |
| SK-CO-1 | 1.20 | 0.007 | <0.001 | G12V |

TABLE 2-continued

| CRC mutant KRAS cell lines | Compound 1 (IC$_{50}$ μM) | Trametinib (IC$_{50}$ μM) | Trametinib + Compound 1(1 μM) (IC$_{50}$ μM) | KRAS mutation |
|---|---|---|---|---|
| SNU-81 | >10 | 0.069 | 0.039 | A146T |
| SNU-C2A | 8.907 | 24.0 | 0.346 | G12A |
| SW1116 | 10.8 | 0.035 | 0.024 | G12A |
| SW480 | 2.87 | 0.013 | 0.001 | G12V |
| SW620 | 1.83 | 0.042 | <0.001 | G12V |
| SW837 | 4.18 | 0.016 | 0.004 | G12C |
| SW948 | 2.18 | 0.144 | 0.014 | Q61L |
| T84 | 5.31 | 0.547 | 0.078 | G13D |

Example 6: Pancreatic Cancer Cell Viability Assay

Two thousand cells per well were seeded in 96 or 384 well white plate, and then treated with indicated compounds for 72 hours (37° C., 5% $CO_2$). Cell proliferation was measured using CellTiter-Glo luciferase-based ATP detection assay (Promega) following the manufacturer's protocol. IC$_{50}$ determinations were performed using GraphPad Prism software (GraphPad, Inc., San Diego, Calif.).

Results showing cell viability % of the MEK1/2 inhibitor (trametinib), Compound 1, and the combination of the MEK1/2 inhibitor (trametinib) with Compound 1 (1 μM) in mutant KRAS pancreatic cancer cell lines were evaluated. The IC$_{50}$ values are summarized in Table 3.

TABLE 3

| Pancreatic Cancer KRAS Cell lines | Compound 1 IC50 (μM) | Trametinib IC50 (μM) | Trametinib + Compound 1 (1 μM) IC50 (μM) | KRAS mutation |
|---|---|---|---|---|
| ASPC-1 | 8.23 | 0.05 | 0.02 | G12D |
| Capan-1 | 1.04 | 0.03 | <0.001 | G12V |
| Capan-2 | 0.69 | 0.08 | <0.001 | G12V |
| CFPAC-1 | 2.38 | NA | 0.01 | G12V |
| HPAC | 1.06 | 0.03 | <0.001 | G12D |
| HPAF-II | 3.53 | 0.04 | 0.02 | G12D |
| HS766T | 2.49 | 0.01 | <0.001 | Q61H |
| HUP-T4 | 2.21 | NA | 0.05 | G12V |
| KP4 | 1.32 | NA | 0.06 | G12D |
| MIAPACA-2 | 1.13 | 0.02 | <0.001 | G12C |
| Panc 03.27 | 1.18 | 1.48 | 0.08 | G12V |
| Panc 05.04 | 1.02 | 0.02 | <0.001 | G12D |
| Panc 10.05 | 2.77 | 0.30 | 0.06 | G12D |
| Panc-1 | 5.28 | NA | >10 | G12V |
| SU.86.86 | 2.01 | NA | 6.65 | G12D |
| SW1990 | 6.37 | NA | 0.23 | G12D |

Example 7. Cell Proliferation Assays of Compound 1 in Combination with Trametinib in A-427, HCT-116 and PSN1 Cell Models Cell proliferation assays were performed in select cell models (A-427, HCT-116 and PSN1) in a combination dose matrix comprising a combination of trametinib and Compound 1 to determine synergy at other dose levels of Compound 1. One to two thousand cells per well were seeded in 96 well clear bottom black-walled 96 well microplates, and then treated with indicated compounds for 72-120 hours (37° C., 5% $CO_2$). Trametinib concentrations ranged from 10 to 1.5 nM titrated 3-fold across the plate and Compound 1 titrated from 3 μM to 37 nM titrated 3 fold down as indicated. Single agent efficacy from Trametinib and Compound 1 was also tested at dose ranges of 10 μM to 1.5 nM titrated 3-fold across for both compounds. Cell proliferation was measured using CellTiter-Glo luciferase-based ATP detection assay (Promega) following the manufacturer's protocol and read with a SYNERGY H1 multi-reader (BIOTEK). IC50 determinations were performed using GraphPad Prism software (GraphPad, Inc., San Diego, Calif.). Degree of synergy was determined with the full combination matrix using a BLISS additivity software (Bioinformatics, Volume 33, Issue 15, 1 Aug. 2017, Pages 2413-2415).

7A. Trametinib and Compound 1 Combination Cell Viability Assay for A-427 NSCLC

Trametinib treatment in combination with Compound 1 demonstrated a dose dependent benefit with addition of Compound 1 at different concentrations. Additional combinations at varying doses of both trametinib and Compound 1 revealed ranges of drug concentrations that may yield synergistic benefit. Synergy was assessed by BLISS independence analysis on the Synergyfinder website (Ianevski A, He L, Aittokallio T, Tang J. SynergyFinder: a web application for analyzing drug combination dose-response matrix data. Bioinformatics. 2017 Aug. 1; 33(15):2413-2415). Concentrations that yielded greatest synergy fell between 13.7 to 123 nM for trametinib and 37 to 333 nM for Compound 1 with an average calculated BLISS synergy score of 13.69.

TABLE 4

| Drug Combination | Synergy Score | Most Synergistic Area Score | Method |
|---|---|---|---|
| Compound 1 + Trametinib | 4.14 | 13.69 | Bliss |

7B. Trametinib and Compound 1 Combination Cell Viability Assay for HCT-116 CRC

Trametinib treatment in combination with Compound 1 demonstrated a dose dependent benefit with addition of Compound 1 at different concentrations. Additional combinations at varying doses of both trametinib and Compound 1 revealed ranges of drug concentrations that may yield synergistic benefit. Synergy was assessed by BLISS independence analysis on the Synergyfinder website. Concentrations that yielded greatest synergy fell between 4.6 to 41.2 nM for trametinib and 333 nM to 3 μM for Compound 1 with an average calculated BLISS synergy score of 14.02.

TABLE 5

| Drug Combination | Synergy Score | Most Synergistic Area Score | Method |
|---|---|---|---|
| Compound 1 + Trametinib | 4.51 | 14.02 | Bliss |

7C. Trametinib and Compound 1 Combination Cell Viability Assay for PSN1

Trametinib treatment in combination with Compound 1 demonstrated a dose dependent benefit with addition of Compound 1 at different concentrations. Additional combinations at varying doses of both trametinib and Compound 1 revealed ranges of drug concentrations that may yield synergistic benefit. Synergy was assessed by BLISS independence analysis on the Synergyfinder. Concentrations that yielded greatest synergy fell between 1.5 to 13.7 nM for trametinib and 111 nM to 1 µM for Compound 1 with an average calculated BLISS synergy score of 13.64.

TABLE 6

| Drug Combination | Synergy Score | Most Synergistic Area Score | Method |
| --- | --- | --- | --- |
| Compound 1 + Trametinib | 4.85 | 13.65 | Bliss |

Example 8. Immunoblotting for Cellular Kinase Phosphorylation (HCT-116)

Approximately 300 thousand cells per well were seeded in 6 well plate for 24 hrs, and then treated with compounds for 4, 24 or 48 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1× Halt protease and phosphatase inhibitors (Thermo Scientific). Protein lysates (approximately 20 µg) was resolved on 4-12% Bolt Bis-Tris precast gels with IVIES running buffer (Life Technologies), transferred to nitrocellulose membranes using Trans-Blot Turbo Transfer System (Bio-Rad) and detected with antibodies targeting phosphorylated STAT3, FAK, SRC, AKT, ERK, S6 (Cell Signaling Technology), total STAT3, FAK, SRC, AKT, and ERK, S6, and beta-Actin (Cell Signaling Technology) Antibodies were typically incubated overnight at 4° C. with gentle rocking, followed by washes and incubation with the appropriate HRP-conjugated secondary antibodies. Membranes were incubated with chemiluminescent substrate (Bio-Rad Clarity Western ECL) for 2 min at room temperature. The chemiluminescent images were acquired with an iBRIGHT FL1500 Imaging System (ThermoFisher). Results in HCT-116 KRAS G13D CRC show that Compound 1 alone suppresses protein levels of phospho-FAK (pFAK), phospho-SRC (pSRC), phospho-STAT3 (pSTAT3) at 4 and 24 h time points. Trametinib inhibited pERK at all timepoints and inhibited pSRC at 24h as a single agent. Single agent trametinib upregulated pSTAT3, however, this upregulation was repressed by addition of compound 1 as observed at 4 and 24h. Both trametinib and compound 1 inhibited phosphorylation of the S6 protein as single agents, however, combination treatment of the two compounds resulted in a more complete inhibition by 24h. The combination of suppression of these signaling nodes supports the significantly increased inhibition of cell proliferation observed with the combination treatment. Combination of Compound 1 with trametinib also results in greater PARP cleavage.

Example 9. Immunoblotting for Cellular Kinase Phosphorylation (PSN1)

Approximately half a million cells per well were seeded in 6 well plate for 24 hrs, and then treated with compounds for 4, 24 or 48 hours. Cells were collected after treatment and lysed in RIPA buffer (50 mM Tris, pH 7.4, 150 mM NaCl, 1% NP-40, 0.5% Deoxycholate, 0.1% SDS) supplemented with 10 mM EDTA, 1× Halt protease and phosphatase inhibitors (Thermo Scientific). Protein lysates (approximately 20 µg) was resolved on 4-12% Bolt Bis-Tris precast gels with IVIES running buffer (Life Technologies), transferred to nitrocellulose membranes using Trans-Blot Turbo Transfer System (Bio-Rad) and detected with antibodies targeting phosphorylated AKT, ERK, S6 (Cell Signaling Technology), total AKT, and ERK, S6, and beta-Actin (Cell Signaling Technology) Antibodies were typically incubated overnight at 4° C. with gentle rocking, followed by washes and incubation with the appropriate HRP-conjugated secondary antibodies. Membranes were incubated with chemiluminescent substrate (Bio-Rad Clarity Western ECL) for 2 min at room temperature. The chemiluminescent images were acquired with an iBRIGHT FL1500 Imaging System (ThermoFisher). Results in PSN1 KRAS G12R Pancreatic cancer cell line show that trametinib inhibited pERK as a single agent in and that combination with Compound 1 yielded similar results. Single agent Compound 1 at both 333 nM and 1 µM inhibited phosphorylation of AKT at S473. Furthermore, trametinib was able to inhibit phosphorylation of S6 at S235/S236 as a single agent and addition of Compound 1 enhanced phosphoS6 inhibition.

Figure 4A:
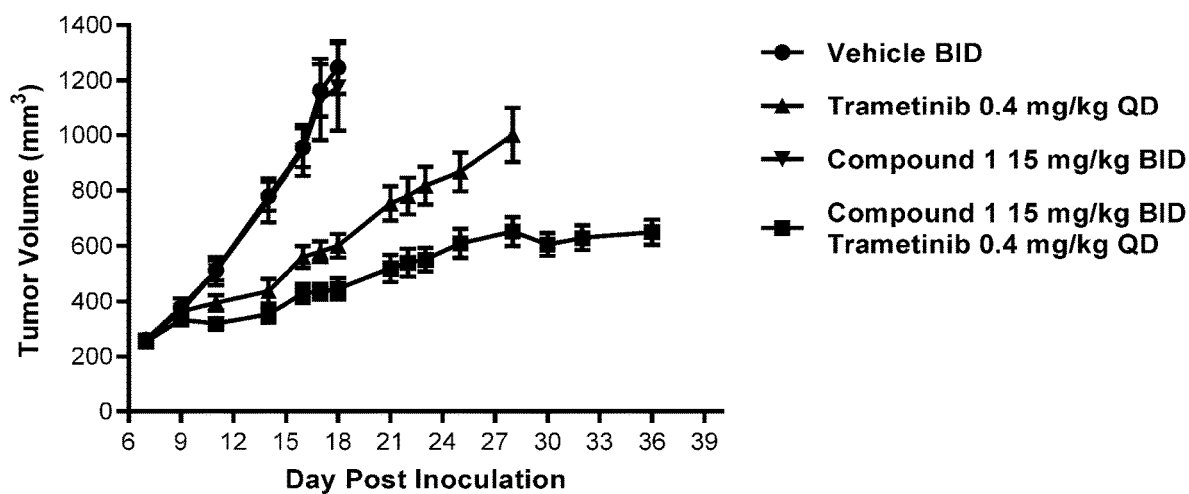
FIG. 4a is a chart showing the antitumor effect of Compound 1 in combination with trametinib in HCT-116 cell-derived xenograft tumors harboring the $KRAS^{G13D}$ mutation in SCID/Beige mice. (●) Control; (▼) Compound 1 (15 mg/kg BID); (▲) Trametinib (0.4 mg/kg QD); (■) Compound 1 (15 mg/kg BID) plus Trametinib (0.4 mg/kg QD).
Figure 4B:
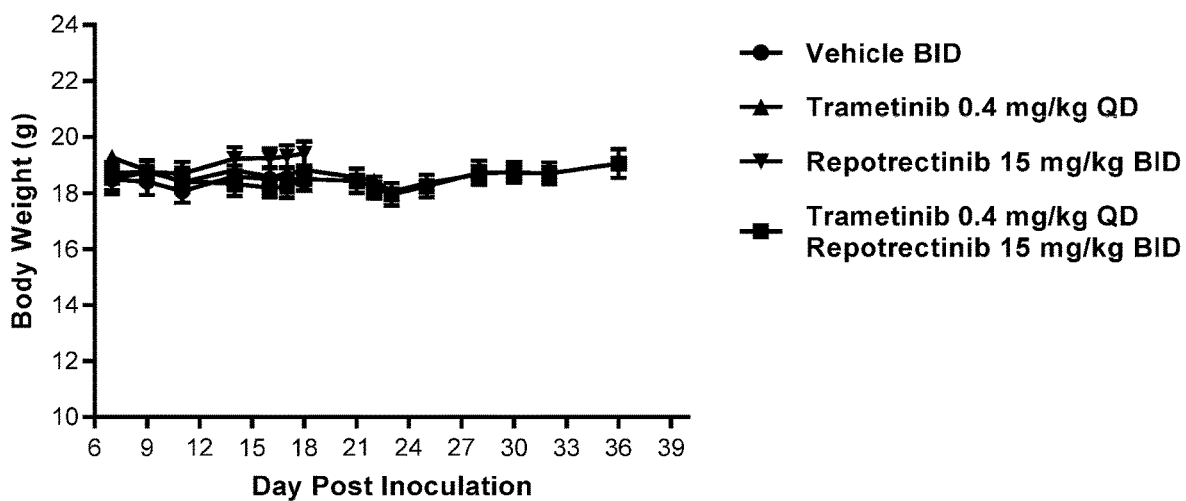

Example 10. Effect of Compound 1 in Combination with Trametinib in HCT-116 Cell-Derived Xenograft Tumor Model of CRC HCT-116 is a colon cancer cell line harboring a KRAS G13D mutation. SCID/Beige mice bearing HCT-116 cell-derived tumors were randomized to treatment groups, including groups treated with vehicle BID, Compound 1 BID at 15 mg/kg, trametinib QD at 0.4 mg/kg, Compound 1 BID at 15 mg/kg in combination with trametinib QD at 0.4 mg/kg. The tumor volume (TMV) vs time data are shown as mean±sem in FIG. 4a. At the data cutoff on day 18 when the vehicle treated group was euthanized, treatment with Compound 1 in combination with trametinib at 0.4 mg/kg dose level significantly reduced tumor volume compared to the treatment with Compound 1 only ($p<0.0001$, post hoc Dunnett's multiple comparison test following two-way ANOVA) or the treatment with trametinib (0.4 mg/kg) only ($p<0.001$, post hoc Dunnett's multiple comparison test following two-way ANOVA). Body weight of the mice were measured during treatment and are shown as mean±sem in FIG. 4b. At the data cutoff on day 18 when the vehicle treated group was euthanized, there is no statistically significant difference of body weight among treatment groups ($p=0.61$, two-way ANOVA).

Example 11. Pharmacodynamic Effect of Compound 1 in Combination with Trametinib in HCT-116 Cell-Derived Xenograft Tumors To evaluate the pharmacodynamic effect of Compound 1 in combination with trametinib in HCT-116 cell-derived xenograft tumors, tumor lysate was prepared and analyzed by immunoblotting using antibodies against the candidate molecules selected from signaling pathways that can be potentially modified by Compound 1 and/or trametinib from tumor samples collected at 2h or 9h post the last dose. The inhibitory activities of Compound 1 against SRC were demonstrated by the reduction of phosphorylated SRC signals in tumors treated with Compound 1 at 15 mg/kg twice a day (BID) either as the single agent or in combination with trametinib at 0.4 mg/kg at both time points, whereas reduction of phosphorylated SRC was not observed in the trametinib treatment group. In addition, trametinib treatment led to elevated phosphorylated FAK level, while Compound 1 in combination with trametinib attenuated this elevation at both time points. Compound 1 inhibited the phosphorylation of STAT3 at 2h but not 9h post the last dose. Finally, reduction of phosphorylated ERK signal was observed in groups treated with trametinib either as a single agent or in combination with Compound 1.

Figure 5A:
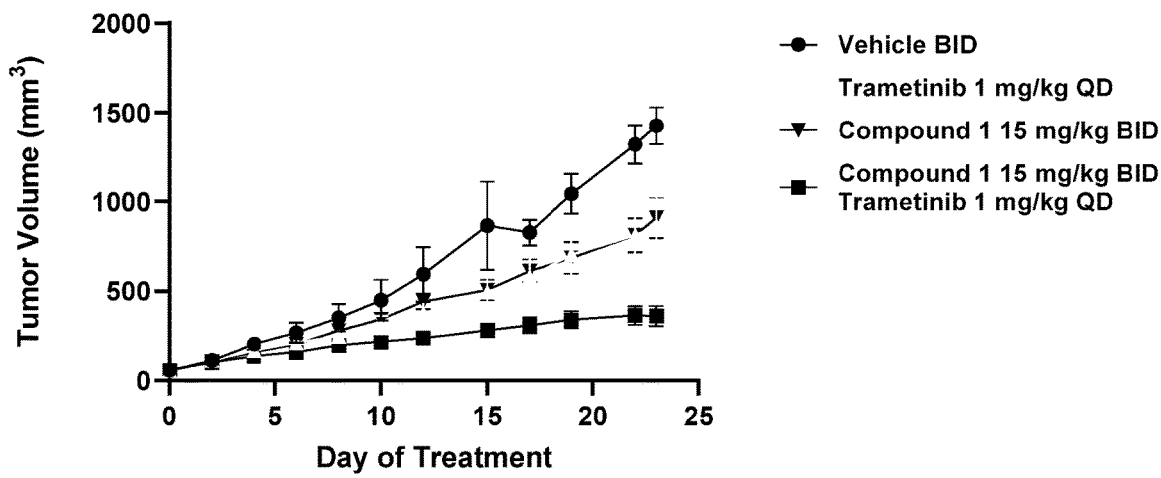
FIG. 5a is a chart showing the antitumor effect of Compound 1 in combination with trametinib in mLU6045 MuPrime mouse lung cancer model with $KRAS^{G12D/+}$; $p53^{-/-}$ mutations in C57BL/6 mice. (●) Control; (▼) Compound 1 (15 mg/kg BID); ( ) Trametinib (1 mg/kg QD); (■) Compound 1 (15 mg/kg BID) plus Trametinib (1 mg/kg QD).
Figure 5B:
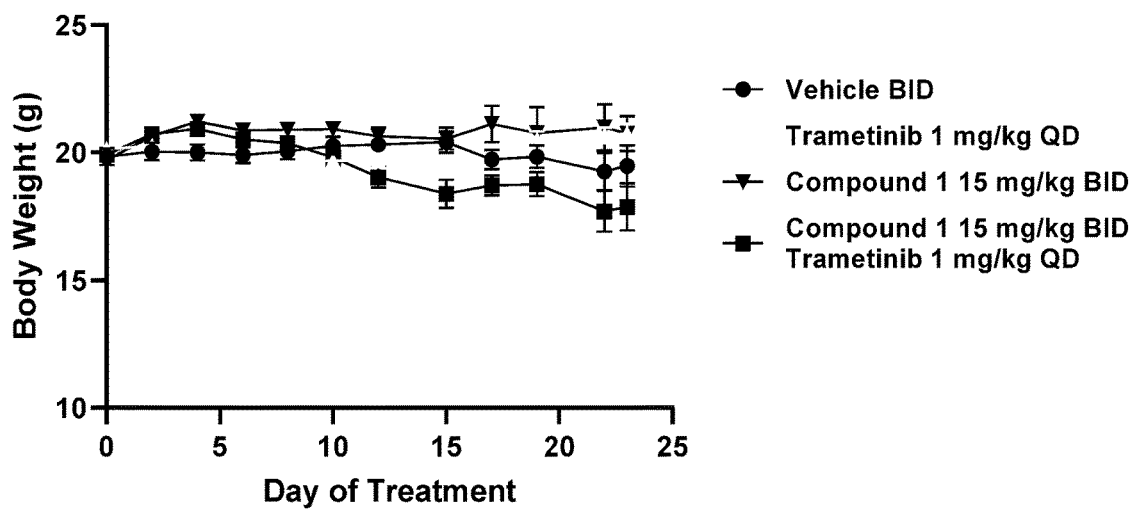

Example 12. Effect of Compound 1 in Combination with Trametinib in the Subcutaneous mLU6045 MuPrime Mouse Lung Cancer Model with $KRAS^{G12D/+}$; $p53^{-/-}$ Mutations The subcutaneous mLU6045 MuPrime lung cancer model is derived from mouse lung tumors induced by constitutive activate $KRAS^{G12D/+}$ heterozygous mutation and p53 homozygous null mutation in lung cells. It is worth noting that the drug effect was evaluated in C57BL/6 mice with an intact immune system in this study. The tumor volume vs time data are shown as mean±sem in FIG. 5a. Tumor volume in the group treated with Compound 1 in combination with trametinib was statistically significantly smaller than those in the group treated with vehicle (p<0.0001, mixed-effects model followed by Tukey's multiple comparison test) or Compound 1 only (p=0.0052, mixed-effects model followed by Tukey's multiple comparison test) and have a trend to be smaller than that in the group treated with trametinib only (p=0.0590, mixed-effects model followed by Tukey's multiple comparison test). Further analysis of data on the last day of study (day 23) showed that tumor volume of the group treated with Compound 1 in combination with trametinib was statistically significantly smaller than that of the vehicle treated group (p<0.0001, two-stage linear step-up procedure of Benjamini, Krieger and Yekutieli following Kruskal-Wallis test), or that of the Compound 1 treated group (p=0.0123, two-stage linear step-up procedure of Benjamini, Krieger and Yekutieli following Kruskal-Wallis test), or that of the trametinib treated group (p=0.0188, two-stage linear step-up procedure of Benjamini, Krieger and Yekutieli following Kruskal-Wallis test). These results suggest a promising combination effect of Compound 1 and trametinib on anti-tumor activity in this mouse lung cancer model harboring the $KRAS^{G12D/+}$; $p53^{-/-}$ mutations with an intact immune system. The body weight vs time data are shown as mean±sem in FIG. 5b. Although slight and gradual body weight loss was observed in the group of mice treated with Compound 1 in combination with trametinib and one mouse was found dead on day 22, body weight of the group treated with Compound 1 in combination with trametinib was not statistically different from that of the group treated with vehicle (p=0.2231, group effect of the mixed-effect model).

Example 13: Cell Viability Assays Testing Compound 1 in Combination with Trametinib, SHP099/TNO155, LY3214996, RO5126766/CH5126766, or Selumetinib in Patient Derived Lung Organoid and Spheroid Models Human patient derived tumor cells obtained from patient biopsies were maintained and expanded in xenograft mice hosts. Subsequently, patient derived tumors were harvested at appropriate tumor size and dissociated with dipase enzyme to smaller organoids ranging between 20 to 100 micrometer in size. Processed tumor organoids were combined with Matrigel, plated onto 384 well plates and treated with compounds at indicated final drug concentrations as single agent and in combination with select concentrations of Compound 1. Organoids were cultured for 5 days at 37° C. with 5% $CO_2$. On day 5, cell viability was indirectly measured with 3D CTG (Cell Titer Glo) luciferase-based ATP detection assay (Promega) following manufacture's protocol and luminescence is read with an Envision multi-reader.

In parallel, ex vivo 3D Spheroids are isolated from patient derived xenograft (PDX) tumors maintained in mice: tumors are harvested at appropriate tumor size and dissociated with collagenase at 37° C. for up to 30 to 60 mins. Spheroid cell isolates are counted and combined with methylcellulose (final concentration of 0.65%). Approximately 15,000 tumor cell isolates in 90 ul of suspension growth medium are seeded per well in 96-well plates. On the next day after seeding, cells are treated with compounds at indicated final drug concentrations as single agent and in combination with select concentrations of Compound 1. Compound treated tumor cell isolates were cultured for 6 days at 37° C. with 5% $CO_2$ during which time, isolates are allowed to form anchorage independent tumor clusters called spheroids. On day 7, cell viability of spheroids was indirectly measured with 3D CTG (Cell Titer Glo) luciferase-based ATP detection assay (Promega) following manufacture's protocol and luminescence is read with an Envision multi-reader. $IC_{50}$ and area under the curve (AUC) values were calculated using GraphPad Prism software (GraphPad, Inc., San Diego, Calif.).

Results showing cell viability % of the MAPK pathway inhibitors, Compound 1, and the combination of the various inhibitors with Compound 1 (1 μM) in patient derived mutant KRAS lung organoid or spheroid models are summarized in Table 7.

TABLE 7

| Patient Derived Organoid model | Test compounds | single agent IC50 (nM) | combination with 1 uM Compound 1 IC50 (nM) | single agent AUC | combination with 1 uM Compound 1 AUC |
|---|---|---|---|---|---|
| LU5178B KRAS G12D | Trametinib | 94 | 3 | 199 | 74 |
| | Selumetinib | >10000 | 23 | 676 | 312 |
| | LY3214996 (ERKi) | >10000 | 812 | 725 | 389 |

TABLE 7-continued

| Patient Derived Organoid model | Test compounds | single agent IC50 (nM) | combination with 1 uM Compound 1 IC50 (nM) | single agent AUC | combination with 1 uM Compound 1 AUC |
|---|---|---|---|---|---|
| | RO5126766 (RAF/MEKi) | 1387 | 27 | 401 | 172 |
| | TNO155 (SHP099) | >100000 | 4221 | 7699 | 3823 |
| | Repotrectinib | 8699 | | 634 | |
| LU5162B KRAS G12D | Trametinib | >10000 | <1.5 | 598 | 334 |
| | Selumetinib | >10000 | 1 | 824 | 336 |
| | LY3214996 (ERKi) | >10000 | <1.5 | 758 | 345 |
| | RO5126766 (RAF/MEKi) | 3370 | 1 | 486 | 249 |
| | TNO155 (SHP099) | >100000 | 2 | 7699 | 2769 |
| | Repotrectinib | 898 | | 292 | |
| LU0876ex KRAS G12D | Trametinib | 11 | <1.5 | 29.4 | 20.5 |
| | Selumetinib | 198 | <1.5 | 318 | 176 |
| | LY3214996 (ERKi) | 353 | 23 | 206 | 135 |
| | RO5126766 (RAF/MEKi) | 162 | <1.5 | 214 | 113 |
| | TNO155 (SHP099) | 2743 | <1.5 | 3778 | 1733 |
| | Repotrectinib | 879 | | 243 | |
| LU11548ex KRAS G12V | Trametinib | 24 | 5 | 165 | 103 |
| | Selumetinib | 2221 | 297 | 445 | 303 |
| | LY3214996 (ERKi) | 788 | 238 | 326 | 201 |
| | RO5126766 (RAF/MEKi) | 1212 | 122 | 361 | 277 |
| | TNO155 (SHP099) | >100000 | 62624 | 8003 | 5834 |
| | Repotrectinib | 3166 | | 445 | |
| LU6419ex KRAS G12V | Trametinib | 22 | 5 | 230 | 127 |
| | Selumetinib | 5502 | 2283 | 576 | 497 |
| | LY3214996 (ERKi) | 9752 | 1987 | 659 | 408 |
| | RO5126766 (RAF/MEKi) | 1651 | 744 | 437 | 352 |
| | TNO155 (SHP099) | 62863 | 57950 | 7499 | 6403 |
| | Repotrectinib | >10000 | | 712 | |

Example 14. Cell Viability Assays Testing Compound 1 in Combination with Trametinib, RO5126766/C115126766, or Mirdametinib in Patient Derived Pancreatic Cancer Organoid Models Human patient derived tumor cells obtained from patient biopsies were maintained and expanded in xenograft mice hosts. Subsequently, patient derived tumors were harvested at appropriate tumor size and dissociated with dipase enzyme to smaller organoids ranging between 20 to 100 micrometer in size. Processed tumor organoids were combined with Matrigel, plated onto 384 well plates and treated with compounds at indicated final drug concentrations as single agent and in combination with select concentrations of Compound 1. Organoids were cultured for 5 days at 37° C. with 5% $CO_2$. On day 5, cell viability was indirectly measured with 3D CTG (Cell Titer Glo) luciferase-based ATP detection assay (Promega) following manufacture's protocol and luminescence is read with an Envision multi-reader. $IC_{50}$ and area under the curve (AUC) values were calculated using GraphPad Prism software (GraphPad, Inc., San Diego, Calif.).

Results showing cell viability % of the various MAPK pathway inhibitors, Compound 1, and the combination of the various inhibitors with Compound 1 (1 μM or 0.5 μM as indicated) in patient derived mutant KRAS lung organoid or spheroid models are summarized in Tables 8 and 9.

TABLE 8

| Pancreatic Cancer Organoid | Test compounds | single agent IC50 (nM) | combination with 1 uM Compound 1 IC50 (nM) | single agent Viability AUC | combination with 1 uM Compound 1 Viability AUC |
|---|---|---|---|---|---|
| PA13004B KRAS-G12R | Trametinib | 23 | <1.5 | 390 | 121 |
| | RO5126766 (RAF/MEKi) | >10000 | <1.5 | 592 | 213 |
| | Repotrectinib | 544 | | 204 | |

TABLE 8-continued

| Pancreatic Cancer Organoid | Test compounds | single agent IC50 (nM) | combination with 1 uM Compound 1 IC50 (nM) | single agent Viability AUC | combination with 1 uM Compound 1 Viability AUC |
|---|---|---|---|---|---|
| PA20066B KRAS-G12V | Trametinib | 4 | <1.5 | 203 | 72 |
| | RO5126766 (RAF/MEKi) | 61 | <1.5 | 365 | 163 |
| | Repotrectinib | 636 | | 198 | |
| PA20067B KRAS-G12V | Trametinib | 8 | <1.5 | 366 | 154 |
| | RO5126766 (RAF/MEKi) | >10000 | <1.5 | 531 | 300 |
| | Repotrectinib | 881 | | 269 | |
| PA20076B KRAS-G12D | Trametinib | 4 | <1.5 | 263 | 123 |
| | RO5126766 (RAF/MEKi) | >10000 | <1.5 | 508 | 221 |
| | Repotrectinib | 733 | | 205 | |
| PA20077B KRAS-G12D | Trametinib | 6 | 6 | 229 | 68 |
| | RO5126766 (RAF/MEKi) | >10000 | 373 | 577 | 402 |
| | Repotrectinib | 5005 | | 581 | |

TABLE 9

| Pancreatic Cancer Organoid | Test compounds | single agent IC50 (nM) | combination with 0.5 uM Compound 1 IC50 (nM) | single agent Viability AUC | combination with 0.5 uM Compound 1 Viability AUC |
|---|---|---|---|---|---|
| PA20074B KRAS-G12R | Trametinib | 8 | 1 | 448 | 238 |
| | Mirdametinib | 446 | 9 | 448 | 284 |
| | RO5126766 (RAF/MEKi) | 1527 | 32 | 481 | 369 |
| | Repotrectinib | 873 | | 342 | |
| PA20068B KRAS-G12V | Trametinib | 16 | 2 | 259 | 187 |
| | Mirdametinib | 575 | 53 | 326 | 217 |
| | RO5126766 (RAF/MEKi) | 1443 | 140 | 458 | 315 |
| | Repotrectinib | 1356 | | 373 | |
| PA20069B KRAS-G12D | Trametinib | 3 | 1 | 201 | 115 |
| | Mirdametinib | 60 | 30 | 237 | 162 |
| | RO5126766 (RAF/MEKi) | 286 | 60 | 352 | 254 |
| | Repotrectinib | 1443 | | 391 | |

The invention claimed is:

1. A method of treating cancer in a patient in need of such treatment, the method comprising administering to the patient a therapeutically effective amount of a compound that inhibits FAK, SRC, and JAK2 having structure

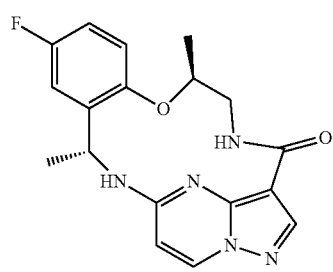 [SMILES: C[C@H]1CNC(=O)c2cnn3ccc(nc23)N[C@H](C)c2cc(F)ccc2O1]

in combination with a therapeutically effective amount of a MEK inhibitor, wherein the MEK inhibitor is trametinib, selumetinib, LY3214996, RO5126766, TNO155 (SHP099), or mirdametinib, or a pharmaceutically acceptable salt thereof.

2. The method of claim 1, wherein at least one genetically altered oncogenic gene has been previously identified in the patient, wherein the at least one genetically altered oncogenic gene is a genetically altered KRAS, a genetically altered NRAS, a genetically altered HRAS, a genetically altered BRAF, a genetically altered MEK, and/or a genetically altered PI3K.

3. The method of claim 2, wherein the genetically altered KRAS comprises at least one mutation selected from the group consisting of G12C, G12V, G12D, G12A, G13C, G12S, D12R, D12F, G13D, G13V, G13R, G13E, Q61H, Q61E, Q61L, and Q61R; or selected from the group consisting of G12D, G13D, and Q61H; or KRAS comprises at least one mutation that is not G12A, G12C, G12S, G12V, and Q61K.

4. The method of claim 1, wherein the cancer is colorectal cancer or pancreatic cancer.

5. The method of claim 1, wherein the compound that inhibits FAK, SRC, and JAK2 is administered in an amount of from about 40 mg to about 200 mg.

6. The method of claim 1, wherein the MEK inhibitor is administered in an amount of from about 0.5 mg to about 2.5 mg.

7. The method of claim 1, wherein the MEK inhibitor is trametinib, or a pharmaceutically acceptable salt thereof.

8. The method of claim 1, wherein the compound that inhibits FAK, SRC and JAK2 is administered in an amount of about 40 mg, about 80 mg, about 120 mg, or about 160 mg by once a day or twice a day.

9. The method of claim 1, wherein the MEK inhibitor is administered in an amount of about 1 mg or about 2 mg.

10. The method of claim 1, wherein the compound that inhibits FAK, SRC and JAK2 is administered on a schedule of at least one dose of about 40 mg, about 80 mg QD, about 120 mg QD, or about 160 mg QD, followed by at least one dose of about 40 mg BID, about 80 mg BID, about 120 mg BID, or about 160 mg BID.

11. The method of claim 1, wherein the MEK inhibitor is administered in at least one dose of about 1 mg QD, or about 2 mg QD.

12. The method of claim 1, wherein the compound that inhibits FAK, SRC and JAK2 is administered at the same time as the MEK inhibitor.

13. The method of claim 1, wherein the compound that inhibits FAK, SRC and JAK2 is administered prior to the MEK inhibitor.

14. The method of claim 1, wherein the compound that inhibits FAK, SRC and JAK2 is administered after the MEK inhibitor.

15. The method of claim 1, wherein the patient has not received a prior treatment.

16. The method of claim 1, wherein the patient has received at least one prior treatment of one or more chemotherapeutic agents or immunotherapies.

17. The method of claim 1, wherein the patient has received at least one prior treatment of one or more chemotherapeutic agents or immunotherapies, and has developed an acquired resistance to the treatment, and/or developed bypass resistance to the treatment.

* * * * *